US011756160B2

(12) United States Patent
Park et al.

(10) Patent No.: US 11,756,160 B2
(45) Date of Patent: Sep. 12, 2023

(54) ML-BASED METHODS FOR PSEUDO-CT AND HR MR IMAGE ESTIMATION

(71) Applicants: Chunjoo (Justin) Park, St. Louis, MO (US); Sasa Mutic, St. Louis, MO (US); Hao Zhang, St. Louis, MO (US); Olga Green, St. Louis, MO (US)

(72) Inventors: Chunjoo (Justin) Park, St. Louis, MO (US); Sasa Mutic, St. Louis, MO (US); Hao Zhang, St. Louis, MO (US); Olga Green, St. Louis, MO (US)

(73) Assignee: Washington University, St. Louis, MO (US)

( * ) Notice: Subject to any disclaimer, the term of this patent is extended or adjusted under 35 U.S.C. 154(b) by 107 days.

(21) Appl. No.: 16/525,562

(22) Filed: Jul. 29, 2019

(65) Prior Publication Data
US 2020/0034948 A1   Jan. 30, 2020

Related U.S. Application Data

(60) Provisional application No. 62/818,993, filed on Mar. 15, 2019, provisional application No. 62/711,023, filed on Jul. 27, 2018.

(51) Int. Cl.
*G06T 3/40*     (2006.01)
*G06T 5/00*     (2006.01)
(Continued)

(52) U.S. Cl.
CPC .......... *G06T 3/4053* (2013.01); *A61B 6/5258* (2013.01); *A61N 5/1039* (2013.01);
(Continued)

(58) Field of Classification Search
CPC .......... A61N 2005/1055; A61N 5/1039; A61N 5/1049; A61N 5/1067; G06N 20/10;
(Continued)

(56) References Cited

U.S. PATENT DOCUMENTS 10,032,256 B1 * 7/2018 Anaya .................... G06T 5/002
2011/0268328 A1 * 11/2011 Bar-Aviv ................ G06T 5/002
                                                         382/128

(Continued)

FOREIGN PATENT DOCUMENTS

WO    WO2018048507    3/2018

OTHER PUBLICATIONS

Chen et al., "DeepLab: Semantic Image Segmentation with Deep Convolutional Nets, Atrous Convolution, and Fully Connected", ArXiv. 2017:1-14.
(Continued)

*Primary Examiner* — Pinalben Patel

(57) ABSTRACT

The present disclosure describes a computer-implemented method of transforming a low-resolution MR image to a high-resolution MR image using a deep CNN-based MRI SR network and a computer-implemented method of transforming an MR image to a pseudo-CT (sCT) image using a deep CNN-based sCT network. The present disclosure further describes a MR image-guided radiation treatment system that includes a computing device to implement the MRI SR and CT networks and to produce a radiation plan based in the resulting high resolution MR images and sCT images.

6 Claims, 44 Drawing Sheets
(33 of 44 Drawing Sheet(s) Filed in Color)

(51) Int. Cl.
*G06N 3/08* (2023.01)
*G06N 3/04* (2023.01)
*G06F 17/18* (2006.01)
*A61B 6/00* (2006.01)
*A61N 5/10* (2006.01)
*G06N 20/20* (2019.01)
*G06N 3/045* (2023.01)

(52) U.S. Cl.
CPC .............. *G06F 17/18* (2013.01); *G06N 3/045* (2023.01); *G06N 3/08* (2013.01); *G06N 20/20* (2019.01); *G06T 5/002* (2013.01); *G06T 2207/10088* (2013.01)

(58) Field of Classification Search
CPC ........ G06N 20/20; G06N 5/003; G06N 3/088; G06N 7/005; G06N 3/0472; G06N 3/0481; G06N 5/025; G06N 3/08; G06N 3/082; G06N 3/0454; A61B 6/032; A61B 6/5247; A61B 6/5258; G06T 3/4053; G06T 5/002; G06T 2207/10088; G06F 17/18
See application file for complete search history.

(56) References Cited

U.S. PATENT DOCUMENTS

| | | | |
|---|---|---|---|
| 2013/0266198 A1* | 10/2013 | Pereira | G06T 7/0012 382/131 |
| 2016/0247263 A1* | 8/2016 | Mailhe | G06T 5/10 |
| 2017/0072222 A1 | 3/2017 | Siversson | |
| 2017/0337682 A1* | 11/2017 | Liao | G06T 7/30 |
| 2018/0099152 A1* | 4/2018 | Nioutsikou | G06T 7/0014 |
| 2018/0357537 A1* | 12/2018 | Munkberg | G06N 3/063 |

OTHER PUBLICATIONS

Chen et al., Rethinking atrous convolution for semantic image segmentation, ArXiv. 2017:1-14.
Chen et al., "Encoder-decoder with atrous separable convolution for semantic image segmentation", ArXiv. 2018;:1-12.
Donoho, D. L., "Compressed sensing," *IEEE Transactions on information theory*, vol. 52, No. 4, pp. 1289-1306, 2006.
Fu et al., Male pelvic synthetic CT generation from T1-weighted MRI using 2D and 3D convolutional neural networks. ArXiv. 2018:1-13.
Goodfellow et al., "Generative Adversarial Nets," *Advances in Neural Information Processing Systems*, pp. 2672-2680, 2014.
Han X. MR-based synthetic CT generation using a deep convolutional neural network method. *Med Phys*. 2017;44(4):1408-1419.
Isola, et al., "Image-to-image translation with conditional adversarial networks," *Computer Vision and Pattern Recognition*, 2017.
Kingma et al., "Adam: A method for stochastic optimization", ArXiv. 2017:1-15.
Maspero et al., "Fast synthetic CT generation with deep learning for general pelvis MR-only radiotherapy", ArXiv. 2018:1-14.
Ronneberger et al., "U-net: Convolutional networks for biomedical image segmentation," ArXiv. 2015: 1-8.
Srivastava et al., Dropout: A simple way to prevent neural networks from overfitting, *J Mach Learn Res*. 2014(15):1929-1958.
Yang et al., "Pseudo CT estimation from MRI using patch-based random forest". Proc. Of SPIE 2017(10133):101332Q-1-101332Q-8.
Zhu et al., "Unpaired image-to-image translation using cycle consistent adversarial networks", ArXiv. 2018:1-18.

* cited by examiner

Step 1: De-noising Auto-Encoder
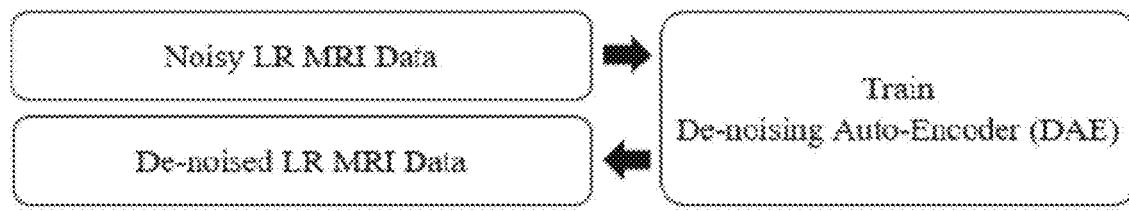
Step 2: Down-Sampling Network
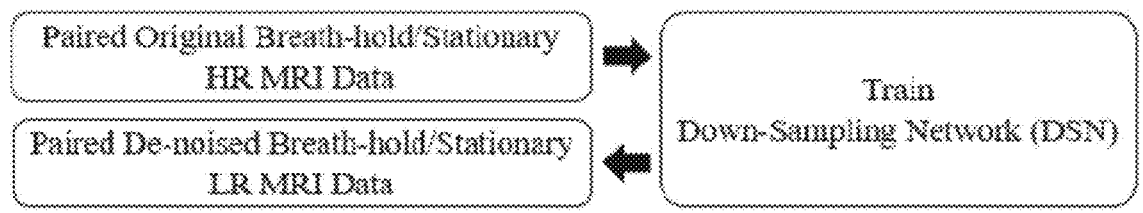
Step 3: Proposed Super-Resolution Generative Model
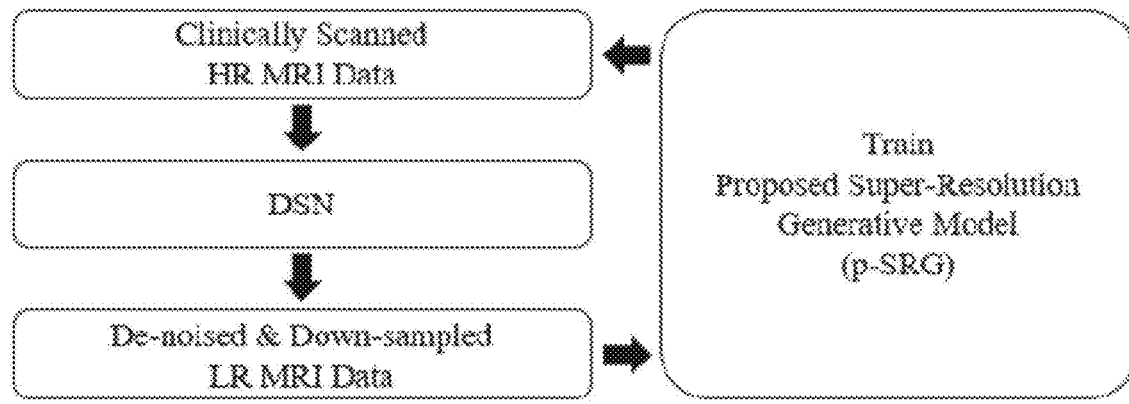
FIG. 7B

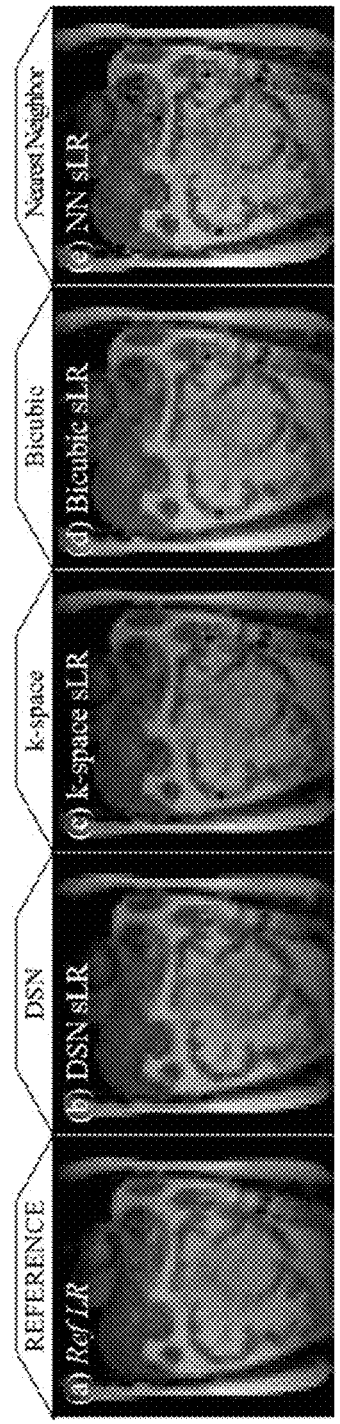
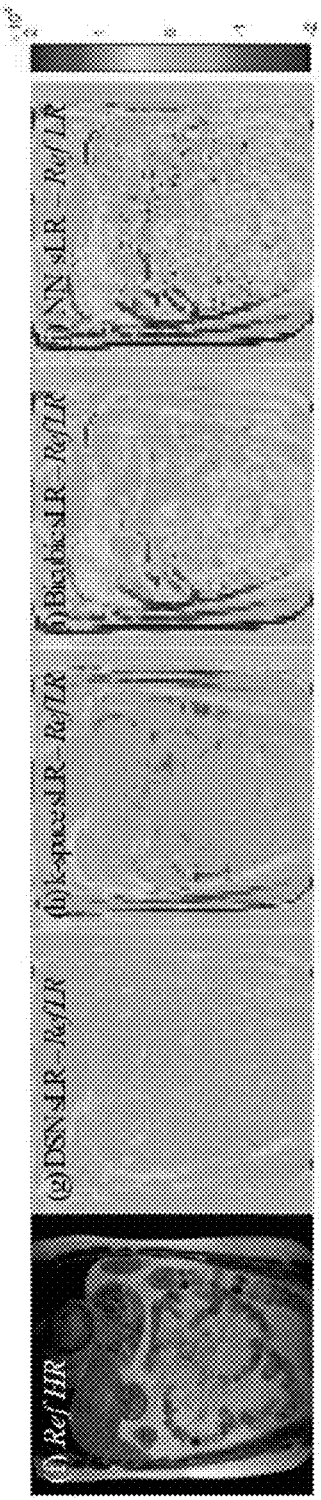
FIG. 35A  FIG. 35B  FIG. 35C  FIG. 35D  FIG. 35E
FIG. 35F  FIG. 35G  FIG. 35H  FIG. 35I  FIG. 35J

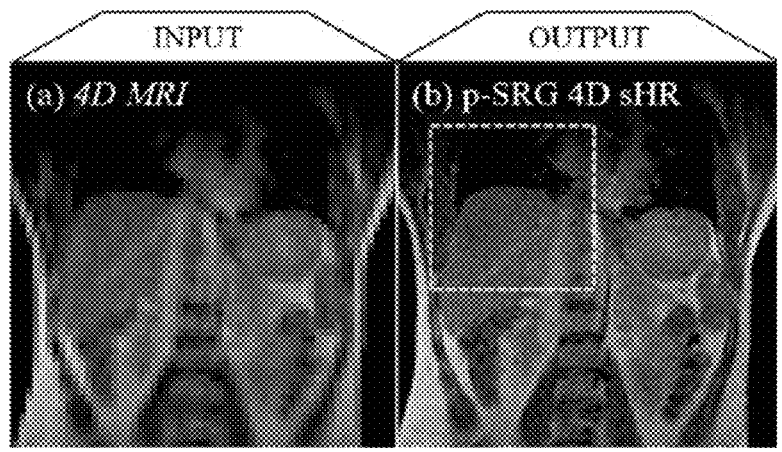
FIG. 40A  FIG. 40B
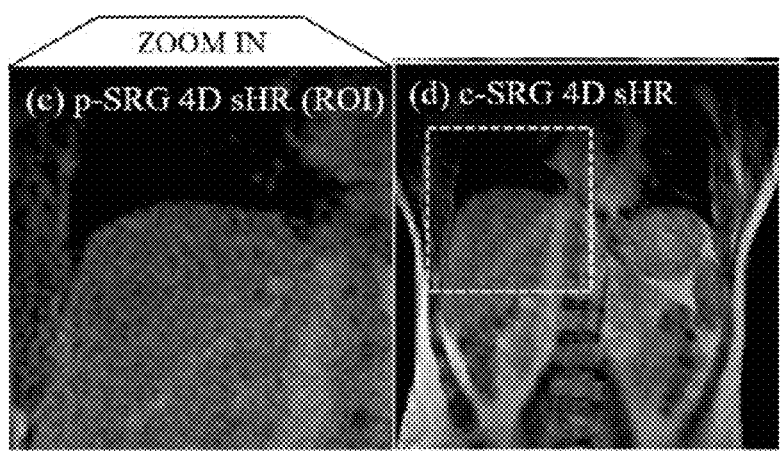
FIG. 40C  FIG. 40D
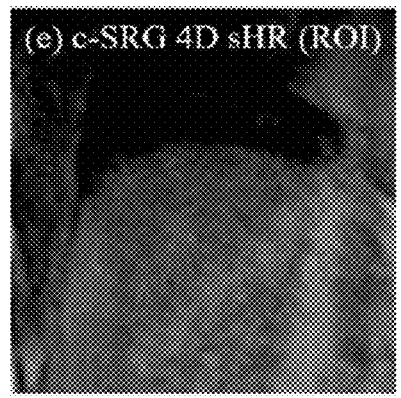
FIG. 40E

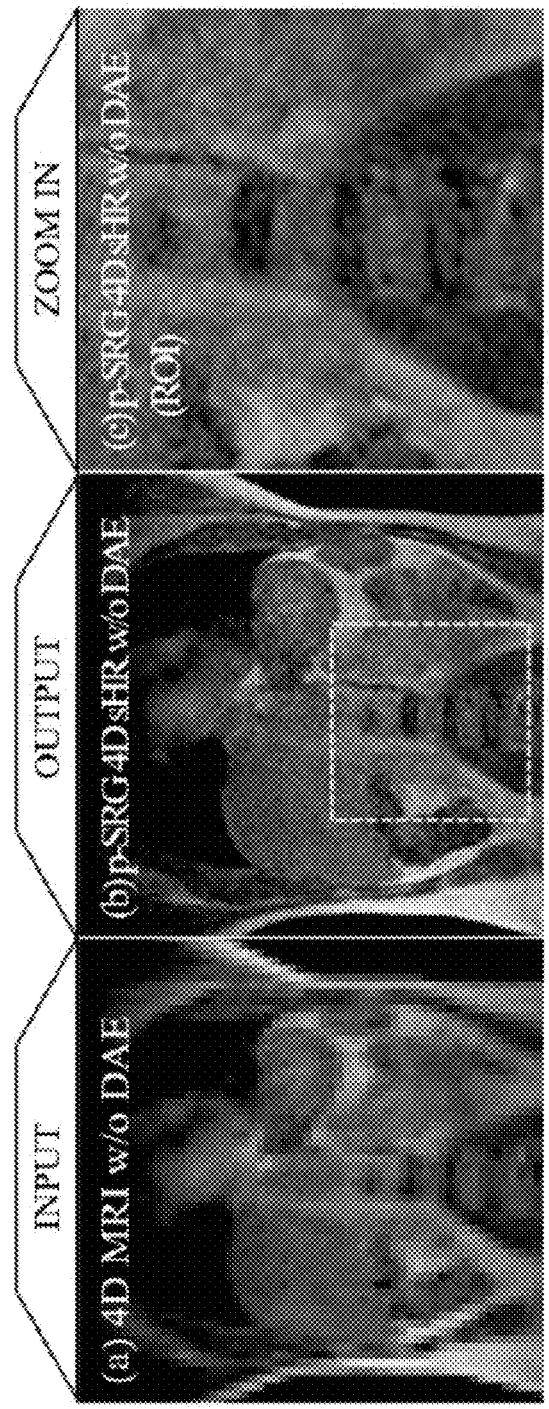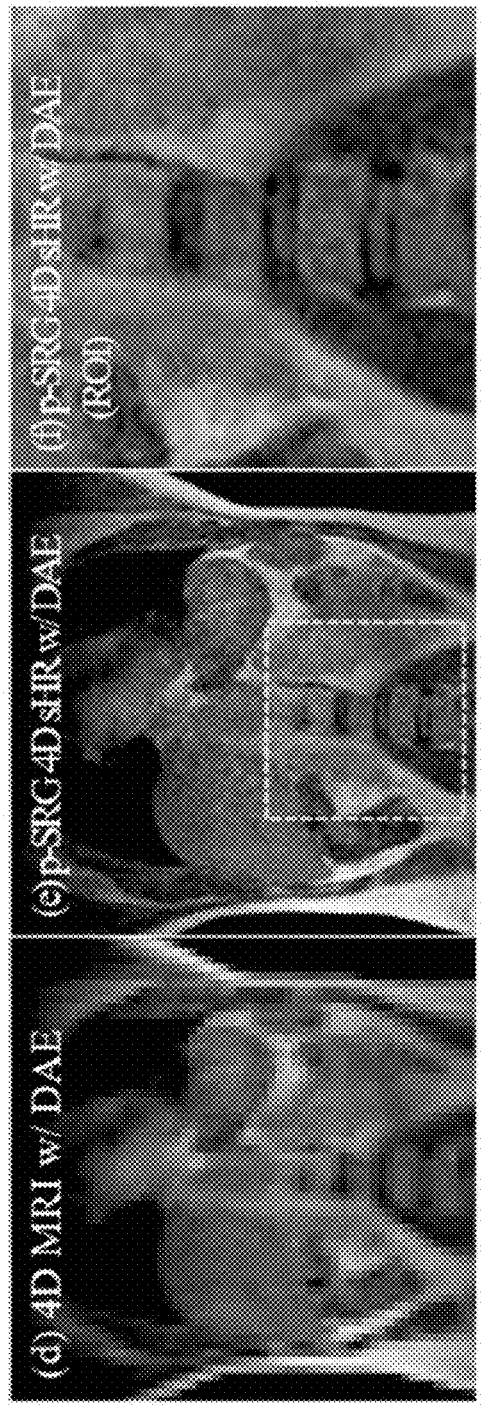

ML-BASED METHODS FOR PSEUDO-CT AND HR MR IMAGE ESTIMATION

CROSS-REFERENCE TO RELATED APPLICATIONS

This application claims the benefit of U.S. Provisional Application No. 62/711,023 filed Jul. 27, 2018 the contents of which are incorporated by reference in its entirety. This application further claims the benefit of U.S. Provisional Application No. 62/818,993 filed Mar. 17, 2019, the contents of which are incorporated by reference in its entirety.

STATEMENT REGARDING FEDERALLY SPONSORED RESEARCH OR DEVELOPMENT

Not applicable.

BACKGROUND

MR image guided radiation therapy (MR-IGRT) exploits MRI's superior soft tissue contrast and real-time tracking and delineation of the tumor and organs at risk (OARs) during the course of treatment. Such unique features have enabled enhanced radiation treatment planning methods such as online adaptive radiation therapy (ART), in which a treatment plan for a patient is re-optimized according to anatomical or positional changes in OARs on a daily basis, significantly improving the accuracy of radiation dose delivery and a substantial reduction in the irradiated volume of normal tissue. Online ART facilitates local dose escalation and the reduction of normal tissue toxicities through real-time, risk-adaptive, and high precision radiotherapy.

Despite the superior features of MRI compared to other image guiding modalities (e.g. CT or cone beam CT), MRI faces the persistent problem of limited spatial resolution. High spatial resolution in MRI comes at the expense of longer scanning time, reduced field of view (FOV), and reduced signal to noise ratio (SNR). In MR-IGRT, the resolution of the MR image fundamentally determines the setup uncertainty, target delineation, and tracking accuracy of radiation therapy. Therefore, the development of methods to minimize the scanning time while maximizing the spatial resolution of MRI would have a significant impact on MR-IGRT quality. Reducing the scan time while maintaining sufficient spatial resolution is crucial during breath-hold MRI scans for patients with moving targets (e.g. lung or liver). The patient must maintain breath-hold at the peak inhale/exhale phase for the duration of the MRI scanning period (17-24 secs), which is often not feasible. Another example is 4D-MRI, where there is a growing interest to replace real-time cine 2D planar imaging for online tumor tracking. 4D-MRI uses fast 3D cine MRI sequences with parallel imaging and echo sharing techniques to minimize the scanning and reconstruction time, and increase temporal resolution. However, limitations in current hardware and software make it challenging to acquire high resolution scans, and such characteristics of 4D-MRI are the critical factors limiting its implementation during MR-IGRT.

To resolve such a persistent problem in MRI, an image post-processing technique known as super resolution (SR) may be utilized to significantly improve the spatial resolution of MRI without changing hardware or scanning components. The aim of SR reconstruction is to reconstruct high resolution (HR) images from a single or a set of low resolution (LR) images to improve the visibility of, or recover, image details. Typically, SR MR image reconstruction is achieved by one of three methods.

Interpolation-based techniques assume that points/regions in an LR image can be expanded into corresponding points/regions in the SR reconstruction using polynomial or interpolation functions with some smoothness priors, which may not be valid in inhomogeneous regions. Moreover, the actual LR sampled points represent a non-ideal sampling where the sampled points represent the intermediate value of the underlying HR points that exist within the LR points. Hence, SR through interpolation typically results in a blurred version of the corresponding HR reference images.

Reconstruction approaches, based upon image down sampling and a degradation model, solve an ill-posed inverse recovery problem from LR to HR images. Typically, reconstruction-based SR methods solve an optimization problem incorporating two terms: a fidelity term, which penalizes the difference between a degraded SR image and an observed LR image, and a regularization term, which promotes sparsity and inherent characteristics of recovering the SR signal (e.g. edge gradient). However, the performance of these reconstruction-based SR methods becomes suboptimal especially in the high frequency region when the input data becomes too sparse or the model becomes even slightly inaccurate. Such drawbacks limit the effectiveness of these methods to small magnification factors that are less than 4.

Machine learning techniques, particularly deep learning (DL)-based SR approaches, have recently attracted considerable attention for achieving state-of-the-art performance in SR for natural images. In contrast to the former approaches, the DL-based method does not require the construction of a transformation model, but instead learns the direct mapping based on information from previously scanned datasets. Among these approaches, the convolutional neural network (CNN) is typically used on account of its simple network structure and high accuracy.

However, existing DL-based methods have three major limitations. First, since MRIs have relatively lower image quality and more complex tissue structures than natural images, it is more challenging to restore high frequency information. The optimization of the conventional method employs the minimization of a pixel-wise difference (e.g. mean squared error between SR images and ground truth HR images), that is often limited when attempting to capture high texture detail. Further, obtaining sufficient training data, that in this case are perfectly matched pairs of LR and HR images, typically poses a challenge. Although HR MRIs from patients previously scanned in the clinic are abundant, the corresponding LR images are typically not available. Current approaches include preparing the training dataset from abundant HR images utilizing a simple translation model such as bicubic interpolation or k-space down sampling. However, these approaches do not reflect real LR scans that are directly generated from MRI scanners, as properties of the signal (e.g. sampling bandwidth or noise) are often not feasible to model with a simple down-sampling method. The third limitation is the performance of SR reconstruction in the presence of noise within the LR MR signals. In general, the SR network cannot distinguish noise from useful features and hence the noise is amplified in the generated HR images, degrading the resulting image quality. Intuitively, this issue can be resolved by de-noising the LR images prior to feeding them into the network. However, conventional image e-noising techniques (e.g. non-local means filter) can be time consuming, limiting their use in a real-time imaging framework.

Further, achieving an MRI-only RT workflow requires the creation of a substitute or synthetic CT (sCT) image set that provides the electron density information necessary for dose calculations based on predicted HU values. A number of previous approaches at creating these sCTs fall generally into several categories.

In an atlas-based approach, pairs of co-registered MRI and CT scans from a patient database are used to create MRI and CT atlases that constitute a typical anatomy as represented by each imaging modality. Determining the deformation between a patient's MRI scan and the MRI atlas allows for the creation of a sCT scan by applying this deformation to the CT atlas. Atlas-based approaches can involve an average atlas for MRI and CT scans composed of the entire database or a multi-atlas in which CT numbers are assigned based on a weighted average of values from multiple deformed CT atlases. Such approaches can quickly become computationally intense as the number of deformations and atlas complexity increases. Additionally, atlas-based approaches struggle in cases where the incoming patient's anatomy differs from that represented by the atlas due to missing tissues, air cavities, or surgical implants.

Voxel-based approaches involve the assignment of CT numbers through a number of methods, including segmentation with standard or specialized MRI sequences, statistical methods, and learning-based approaches. The simplest and most widely used voxel-based approaches use MRI voxel intensities from standard sequences to segment general tissue classes (air, fat, soft tissue, etc.) that are then bulk-assigned corresponding CT numbers. While voxel-based approaches perform better than atlas-based approaches in the case of atypical anatomy, the ambiguity between regions of bone and air due to a lack of signal in both regions can present a challenge.

More recently, deep learning-based approaches using convolutional neural networks (CNNs) have been proposed to solve the problem of sCT generation for sites in the head and pelvis. Model architectures that have been proposed include pre-trained U-Net architectures, 2D and 3D U-Nets, and generative adversarial network (GAN) architectures. However, these DL approaches face challenges similar to the challenges described above with respect to DL-based approaches to super-resolution MRI reconstructions: limited availability of training data, the relatively low resolution of typical MR images, and the effects of noise within the MR data on the pseudo-CT images.

FIELD OF THE INVENTION

The present disclosure generally relates to CT or MR image estimation techniques and methods.

SUMMARY OF THE INVENTION

In one aspect, a method of transforming low-resolution MR signals to produce a corresponding high-resolution MR image using deep learning models is disclosed. In another aspect, a method of transforming MR signals into a pseudo-CT image using deep learning models is disclosed. Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

The figures described below illustrate various aspects of the disclosure.

FIG. 7B is a block diagram illustrating a training framework for training the models of the cascaded deep learning models used to generate high-resolution MR images in accordance with an aspect of the disclosure.

FIG. 26A is an input MR image, FIG. 26B is an sCT image generated by the aspp48 model (RMSE=17.7 HU), FIG. 26C is a true CT image, and FIG. 26D is a difference map between FIG. 26C and FIG. 26B. Similarly, FIG. 26E is an input MR image, FIG. 26F is an sCT image generated by the pix48 (RMSE=27.3 HU) model for the same slice as FIG. 26B, FIG. 26G is a true CT image, and FIG. 26H is a difference map between FIG. 26G and FIG. 26F. Values in the difference maps are in units of HU.

FIG. 35A is a ground-truth low resolution (LR) image acquired from a physical scan.

FIG. 35B is a DSN-generated synthetic LR (sLR) image.

FIG. 35C is a k-space down-sampled image.

FIG. 35D is a bicubic down-sampled image.

FIG. 35E is a nearest neighbor down-sampled image.

FIG. 35F is a ground-truth high-resolution (HR) image acquired from a physical scan.

FIG. 35G is a difference map image (DSN LR of FIG. 35B-Ref LR of FIG. 35A).

FIG. 35H is a difference map image (k-space LR of FIG. 35C-Ref LR of FIG. 35A).

FIG. 35I is a difference map image (Bicubic LR of FIG. 35D-Ref LR of FIG. 35A).

FIG. 35J is a difference map image (Nearest neighbor LR of FIG. 35E-Ref LR of FIG. 35A).

FIG. 40A is a low resolution (LR) axial image obtained from a free breathing 4D-MRI scan physical scan (0.5 sec/vol, 64×64 pixels, 6.0 mm×6.0 mm per pixel) used as input for an SR reconstruction in accordance with one aspect of the disclosure.

FIG. 40B is an image output (256×256 pixels, 1.5 mm×1.5 mm per pixel) from an SRG process in accordance with an aspect of the disclosure.

FIG. 40C is an enlarged image of the area bounded by a superimposed rectangle within the image of FIG. 37B.

FIG. 40D is an image output (256×256 pixels, 1.5 mm×1.5 mm per pixel) from a conventional SRG process FIG. 40E is an enlarged image of the area bounded by a superimposed rectangle within the image of FIG. 37D.

FIG. 42A is an uncorrected (without DAE) low resolution (LR) free-breathing 4D-MRI coronal image obtained from a physical scan (0.5 sec/vol, 64×64 pixels, 6.0 mm×6.0 mm per pixel) used as input for an SR reconstruction in accordance with one aspect of the disclosure.

FIG. 42B is an image output obtained from an SRG process in accordance with an aspect of the disclosure, using the noisy input of FIG. 42A.

FIG. 42C is an enlarged image of the area bounded by a superimposed rectangle within the image of FIG. 42B.

FIG. 42D is a denoised LR free-breathing 4D-MRI coronal image obtained by applying DAE to the noisy LR image of FIG. 42A.

FIG. 42E is an image output obtained from an SRG process in accordance with an aspect of the disclosure, using the de-noised input of FIG. 42D.

FIG. 42F is an enlarged image of the area bounded by a superimposed rectangle within the image of FIG. 42E.

Those of skill in the art will understand that the drawings, described below, are for illustrative purposes only. The drawings are not intended to limit the scope of the present teachings in any way.

DETAILED DESCRIPTION OF THE INVENTION

In various aspects, deep learning-based methods for transforming low resolution MR signals obtained using conventional MR scanning sequences into high resolution MR images, referred to herein as super resolution MR images (SR MRI) are disclosed. In various other aspects, deep learning-based methods for transforming MR images into pseudo CT (p-CT) images are disclosed. All disclosed methods make use of DL models with Generative Adversarial Network (GAN) architectures with additional enhancement to reduce the amount of training data required and to enhance the robustness and processing speed of the DL models. The methods described herein may be incorporated into an MR image-guided radiation therapy (MR-IGRT) workflow that eliminates the need for CT imaging.

I. Super Resolution MRI (MRI SR) DL Framework, Models, and Methods

Deep learning (DL)-based super resolution (SR) reconstruction for magnetic resonance imaging (MRI) has recently been receiving attention due to the significant improvement in spatial resolution compared to conventional SR techniques. Challenges hindering the widespread implementation of these approaches remain, however. Low-resolution (LR) MRIs captured in the clinic exhibit complex tissue structures obfuscated by noise that are difficult for a simple DL framework to handle. Moreover, training a robust network for a SR task requires abundant, perfectly matched pairs of LR and high-resolution (HR) images that are often unavailable or difficult to collect. In various aspects, a novel SR technique for MRI based on the concept of cascaded DL that allows for the reconstruction of high-quality SR images in the presence of insufficient training data, an unknown translation model, and noise is disclosed herein.

In various aspects, a robust MRI SR reconstruction method is provided that includes a cascaded deep learning (DL) framework that overcomes the limitations of previous methods in an efficient and practical manner. In various aspects, the MRI SR DL framework includes a deep Convolutional Neural Network (CNN)-based de-noising autoencoder (DAE) configured to remove noise from low-resolution MR signals obtained for a subject. In various other aspects, the DL framework further includes a deep generative adversarial network (GAN)-based MRI SR network that provides detail preserving HR MRI for the final output.

Figure 8:
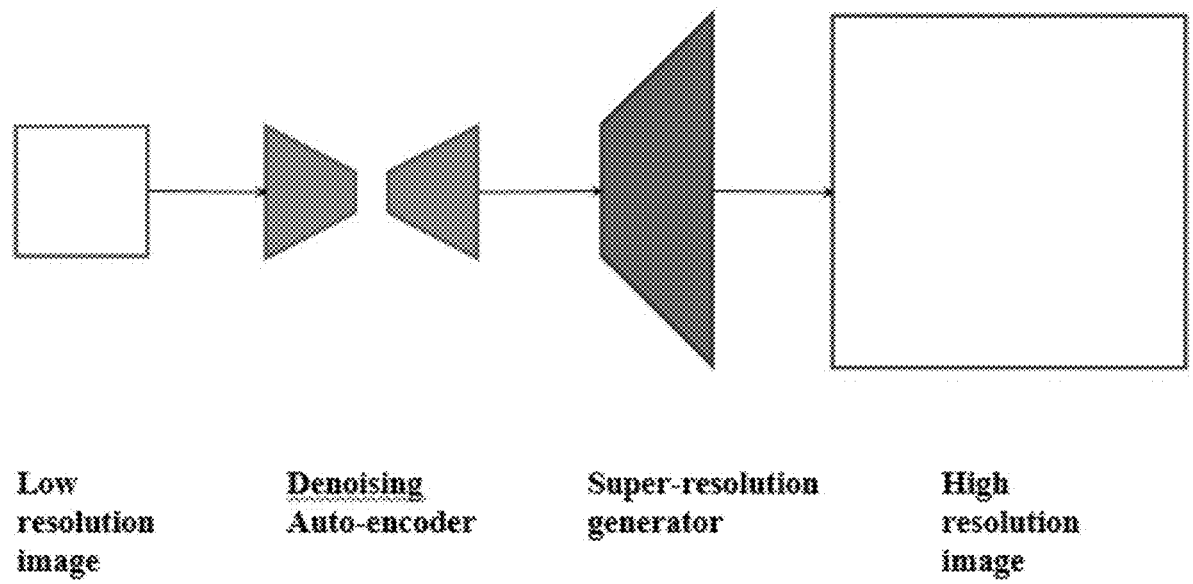
FIG. 8 is a schematic diagram illustrating the inferring framework of the 4DMR super-resolution convolutional network for transforming LR MR images to HR MR images.

The MRI SR framework, shown illustrated in FIG. 8, is an arrangement of feed-forward convolutional neural nets that include a denoising autoencoder (DAE) and a super-resolution generative model (SRG). The DAE serves as an image preprocessing tool to remove the inevitable noise from the raw low-resolution MR signal inputs and the SRG generates the final super resolution image from the denoised LR MR signal inputs. The training processes for the DAE and SRG models of the MRI SR network are separated, as disclosed below.

Figure 7A:
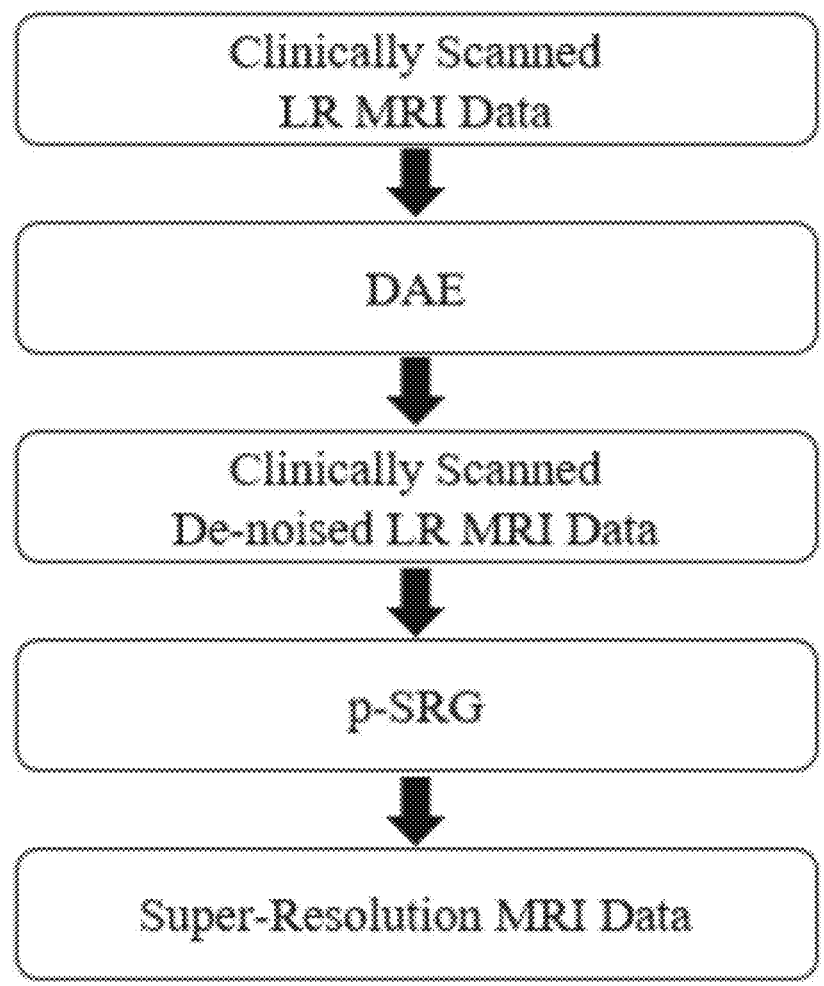
FIG. 7A is a block diagram illustrating a method of producing high-resolution MR images using a cascaded deep learning method in accordance with an aspect of the disclosure.

As illustrated in FIG. 7A, the MRI SR models transform low resolution MR images obtained using conventional MR scanners and scanning sequences to high resolution MR images. Low resolution (LR) MR images are denoised using the DAB, which has been previously trained as described below, to produce denoised LR MR images. The denoised LR MR images are transformed into high resolution (HR) MR images using the super-resolution generator, also previously trained as described below.

In one aspect, the MRI SR network is trained in separate stages. In various aspects, de-noised LR MRIs are paired with HR MRIs to train a CNN-based down-sampling network (DSN) to derive an unknown translation model between the LR and HR images. The DSN is designed to have a small and simple network structure that can be sufficiently trained even with a limited amount of paired LR/HR images acquired from physical phantoms and/or volunteers. In various other aspects, the trained DSN is applied to abundant HR MRI scans to generate perfectly matched pairs of LR and HR images for training a deep generative adversarial network (GAN)-based MRI SR network that provides detail-preserving HR MRI as the final output.

Detailed descriptions of the DAE and super-resolution generator, including model architectures and model training methods, are described in additional detail below.

a) MRI SR Model b) In this study, the translation model between LR and HR MRIs was formulated as the following equation:

$$L\hat{R}_k = T_s(HR_k) + \eta_k \qquad \text{Eq. (1)}$$

where $HR_k$ are the desired HR MRIs to be recovered from the given set of observed LR MRIs, $\{L\hat{R}_k\}$ k=1, . . . , K, $T_s$ describes the down-sampling operator that decreases the resolution by a factor of s, and $\eta_k$ is the additive noise.

For under-sampled k-space measurements, the system of Eq. (1) is underdetermined and hence the inversion process is ill-defined. Therefore, the goal of the SR problem is to recover a FIR image given its down-sampled version such that:

$$\min_{HR_k} E[HR_k, L\hat{R}_k] \qquad \text{Eq. (2)}$$

where $E[\cdot]$ is the energy function that represents the optimization objectives.

Reconstruction-based methods model this energy function as a convex optimization problem to find a plausible HR solution while balancing regularization and/or a priori terms simultaneously, as is the case in total variation reconstruction. On the other hand, DL-based methods construct the energy function on the basis of mean absolute error (MAE) that is the measure of data fidelity between generated SR images from the trained neural network and the corresponding FIR images. The DL-based method uses a parametric CNN model to learn the non-linear mapping function that minimizes the Manhattan norm between SR images reconstructed from LR images $L\hat{R}_k$ and the corresponding ground truth HR images $HR_k$.

However, as described above, there are two unknown variables: the down-sampling operator $T_s$ and the noise $\eta_k$ shown in Eq. (1), that are both ill-posed inverse problems.

To design a robust MRI SR model with the clinical LR MRI scan as an input, it is necessary to estimate and subtract these unknown terms considering they directly relate to the quality of the training data. To overcome this problem, a novel splitting technique, referred to herein as cascaded deep learning (DL) is used in various aspects.

In one aspect, the cascaded DL algorithm splits the MRI SR reconstruction network process into three stages: 1) construction of an image denoising autoencoder (DAE) model to subtract noise $\eta_k$ from a noisy LR image input, 2) construction of a down-sampling network (DSN) to model the unknown down-sampling operator $T_s$ from a subset of paired de-noised LR and HR MRI data, and 3) construction of a SR generative (SRG) model using numerous pairs of HR and LR MRIs generated from the estimated $T_s$. Mathematically, the proposed cascaded DL model is formulated as including the steps of solving Eq. (3), Eq. (4), and Eq. (5), given by:

$$\min_\theta \left\{ \sum_q \left\| DAE(L\hat{R}_q; \theta) - \mu_q \right\|_2^2 \right\} \qquad \text{Eq. (3)}$$

where $DAE(L\hat{R}_q)$ is the denoising autoencoder network with input LR MRI data, $\mu_q$ are de-noised LR images from $L\hat{R}_q$ using a non-local means filter, $DAE(L\hat{R}_q; \theta)$ is a CNN parameterized by θ, q=1 . . . Q is the subset of training data from total number of training sets k=1 . . . K that had physical scans of LR MRI data acquired from physical phantoms and/or volunteers.

$$\min_\rho \left\{ \sum_p \left\| DSN(HR_p; \rho) - DAE(L\hat{R}_p) \right\|_1 \right\} \qquad \text{Eq. (4)}$$

where $DSN(HR_p)$ is the down-sampling network with input HR MRI data that are equivalent to the first term of Eq. (1), p=1 . . . P is the subset of training data from the total number of training sets k=1 . . . K that had close pairs of LR and HR images acquired from physical phantoms and/or volunteers, and $DSN(HR_p; \rho)$ is a CNN parameterized by ρ, and $$\min_\vartheta E[SRG(DSN(HR_k); \vartheta), HR_k] \qquad \text{Eq. (5)}$$

where $SRG(DSN(HR_k))$ is the SR generative model with input $DSN(HR_k)$, $E[\cdot]$ is the GAN energy loss function described in additional detail below, and $SRG(DSN(HR_k); \upsilon)$ is a GAN parameterized by υ.

c) Denoising Autoencoder (DAE)

Figure 9:
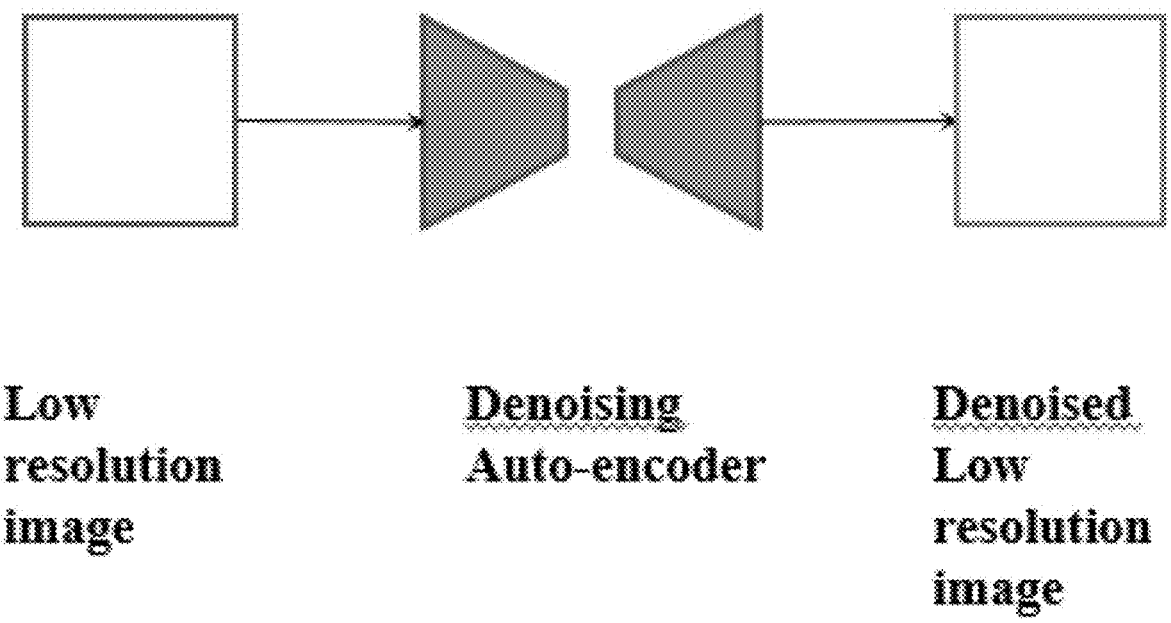
FIG. 9 is a schematic diagram illustrating the DAE training framework of the 4DMR super-resolution convolutional network

Without being limited to any particular theory, the performance of the MRI SR reconstruction method is noticeably impaired by noises or artifacts in the low resolution images that are magnified through the network along with other features of the image, especially for CINE (4D) MR images. Thus, preprocessing the low resolution MR images enhances the effectiveness of the MRI SR reconstruction framework. However, many established image denoising algorithms are potentially time-consuming and hence could not be good candidates for a real-time system. In various aspects, another neural network, a denoising autoencoder (DAE), illustrated in FIG. 9, is included in the MRI SR network that is configured to learn a mapping from noisy LR MR images to corresponding denoised MR images through pairs of training data.

Specifically, if a noise-free image is denoted as x and a corrupted image of x as x̃, the DAE is trained to minimize the reconstruction error of $\|g_{\theta_g}(f_{\theta_f}(\tilde{x}))-x\|$, where $f_{\theta_f}$ and $g_{\theta_g}$ denote the encoding and decoding network parameterized by $\theta_f$ and $\theta_g$, respectively. In various aspects, since the noise-free image x is usually unavailable, an appropriate denoising algorithm is selected to denoise the corrupted image x̃ and treat the denoised image as x. Due to the limitations of data, patches of images to train the DAE instead of the entire images in some aspects.

Figure 31:
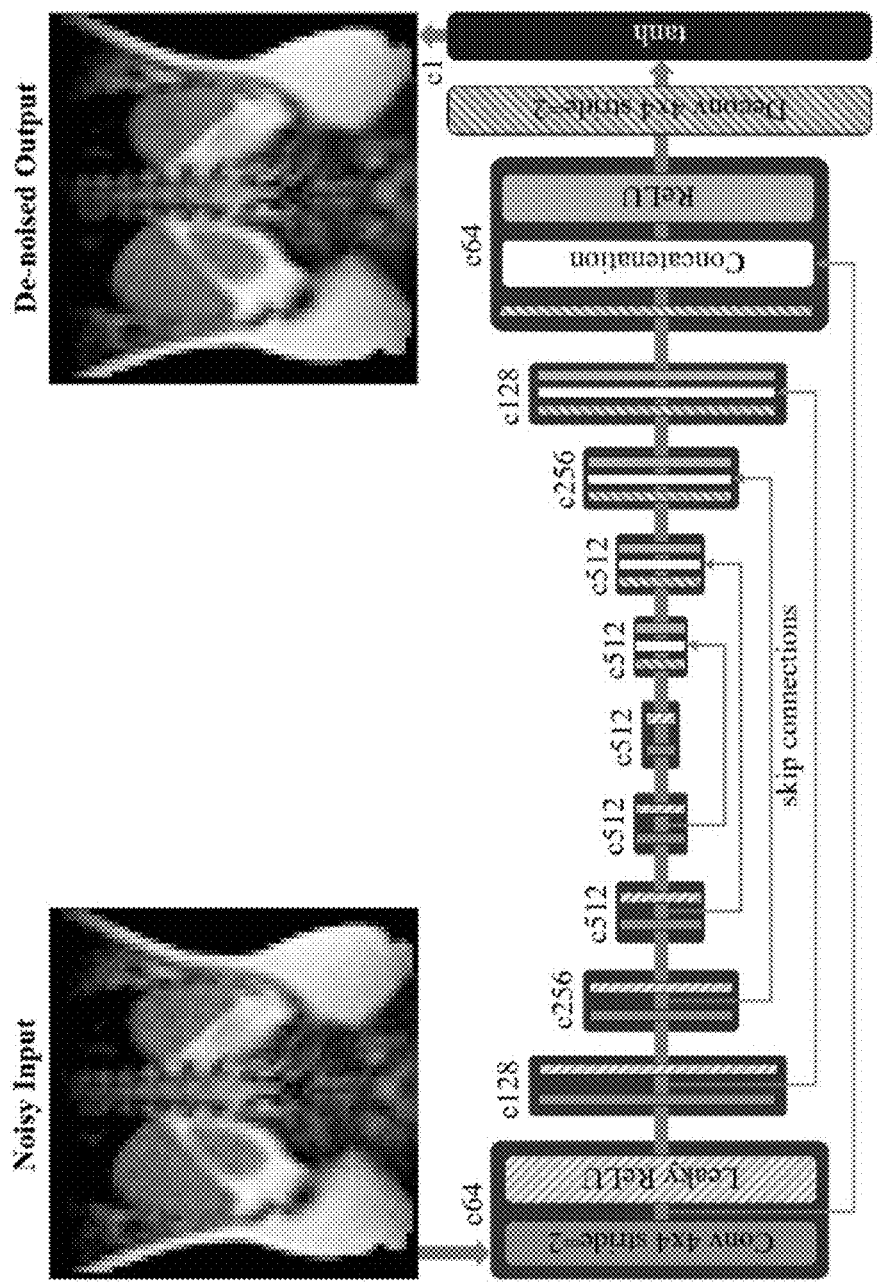
FIG. 31 is a block diagram illustrating the architecture of a denoising autoencoder network (DAE) in accordance within an aspect of the disclosure.

The network structure of the DAE in one aspect is shown in FIG. 31. In various aspects, the basic framework of the DAE comprises an encoder that maps a noisy input image to some hidden representation and a decoder that maps this hidden representation back to the reconstructed version of the de-noised input image. The parameters of the DAE were learned to minimize the construction error measured by the loss function defined in Eq. (3).

Referring again to FIG. 31, the CNN-based DAE is implemented using a cascade of convolutional filters paired with nonlinear activation functions. The network comprises six convolutional layers (encoders) with 4×4 filters and six de-convolutional layers (decoders) with 4×4 filters. Each layer comprises a single convolutional/deconvolutional filter with stride 2. The input images (64×64 pixels) were convolved with successive filters until feature reduction is performed to extract 1×512 features at the deepest layer. These features were processed with subsequent deconvolutional filters to recover the original dimensions of the input images. At the end of each convolutional and deconvolutional layer, leaky and standard rectified linear unit (ReLU) nonlinear activation functions of the form Leaky ReLU(x) =max(0.2x, x) and ReLU(x)=max(0, x) respectively were used to ensure that the output of a layer is a nonlinear representation of the input.

In various aspects, the DAE is trained with pairs of noisy and de-noised LR MRIs that were preprocessed using a noise filter including, but not limited to, a non-local means filter (NLM), which is a popular and efficient image processing technique for de-noising MRIs.

d) Super-Resolution Generator

Recently, numerous convolutional neural network based methods have been developed to tackle the image super-resolution problem and achieved state-of-art results in terms of PSNR (peak-signal-to-noise-ratio). However, high frequency details of the high resolution images were missing from the generated images. One existing method, SRGAN solved this problem by introducing generative adversarial nets (GAN) to the conventional CNN based image super-resolution model.

GAN is a framework for generative model estimation which comprises two models: a generative model G parametrized by $\theta_G$, which generates samples in the data distribution $p_{data}$ from a sample in a latent space $p_z$, and a discriminative model $\theta_D$ that distinguishes whether a given sample is drawn from the data distribution or generated from G with certain probability. The generative model G and the discriminative model D are trained simultaneously in an adversarial manner by solving the minmax problem:

$$\min_{\theta_G}\max_{\theta_D}\{\mathbb{E}_{x\sim P_{data}}\log D_{\theta_D}(x)+\mathbb{E}_{z\sim p_z}\log(1-D_{\theta_D}(G_{\theta_G}(z)))\} \quad \text{Eqn: (1A)}$$

such that if an equilibrium is achieved during training, $G(z)\sim p_{data}$ and D outputs a probability of 0.5 for generations of G, i.e. D is not able to tell the difference between the generated data and the true samples.

In various aspects, the super-resolution generator model of the MRI SR network is developed by training a convolutional neural net G that generates high-resolution images from corresponding low-resolution images by simultaneously training another convolutional net based model D which serves as a binary classifier and helps to train G such that the high-resolution MR images generated from G are essentially indistinguishable from images drawn from the true distribution of high resolution images.

The cost function of the generator G comes from two sources. The first loss represents the reconstruction error (content loss) between the generated image and the ground truth image. In one aspect, mean absolute error (MAE) is selected as the metric for the content loss as it has demonstrated better performance compared with the conventional Frobenius norm. The second loss represents adversarial loss which comes from the discriminator D, which drives the generated image to pursue more high frequency details making it closer to the real images. Note that for better graduation behavior, log–D(G($I_l$)) is used instead of log(1–D(G($I_l$))), where $I_l \sim p_{lr}$ and $I_h \sim p_{hr}$ are low/high resolution images from training dataset. In various aspects, the combined cost function of the generator G and the discriminator D is represented as:

$$l_{loss} = l_{mae} + \lambda l_{adversarial} \quad \text{Eqn. (2A)}$$
$$= \|G(I_l) - I_h\|_1^2 + \lambda \log(-D(G(I_l)))$$

In one aspect, the optimization problem to be solved for the super-resolution MR network is:

$$\min_{\theta_G}\max_{\theta_D} \mathbb{E}_{I_l, I_h \sim plr, hr} \{\log(-D_{\theta_D}(G_{\theta_G}(I_l))) + \|G(I_l) - I_h\|\} + \quad \text{Eq. (3A)}$$
$$\mathbb{E}_{I_h \sim phr} \log D_{\theta_D}(x)$$

In various aspects, Eq. (3A) is then solved by alternatively updating D and G in each sub-problem while fixing the other parameter:

$$\theta_G^k = \arg\min_{\theta_G} \mathbb{E}_{I_l, I_h \sim plr, hr} \{\log(-D_{\theta_D^{k-1}}(G_{\theta_G}(I_l))) + \lambda\|G(I_l) - I_h\|\} \quad \text{Eq. (4A)}$$
$$\theta_D^k = \arg\min_{\theta_D} \mathbb{E}_{I_l, I_h \sim plr, hr} \{\log(-D_{\theta_D}(G_{\theta_G^k}(I_l))) + \log(D(I_h))\}$$

Figure 14:
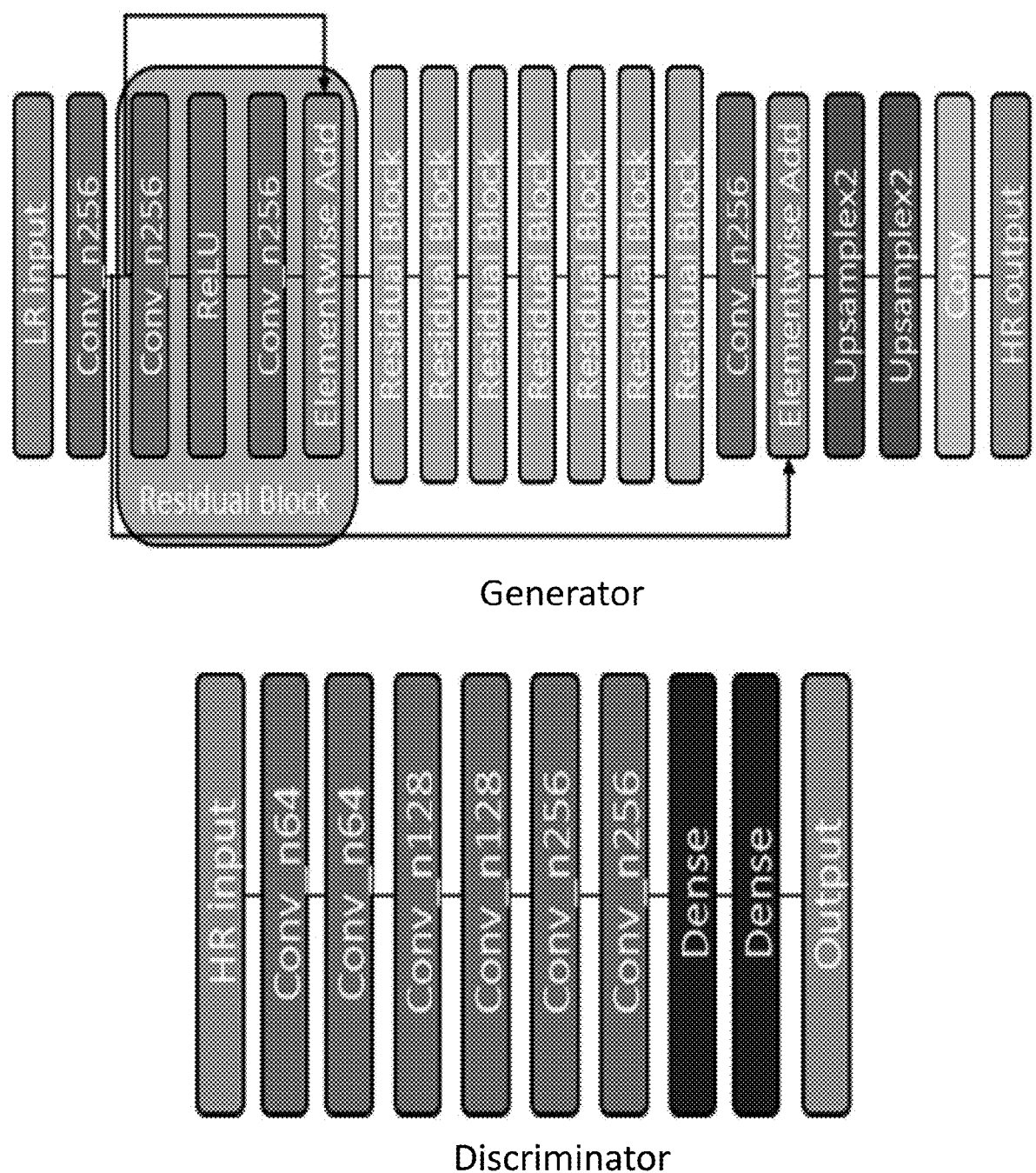
FIG. 14 contains block diagrams representing the network structures of the components of a super-resolution generative (SRG) model based on the generative adversarial network (GAN) framework in accordance within an aspect of the disclosure.
Figure 15:
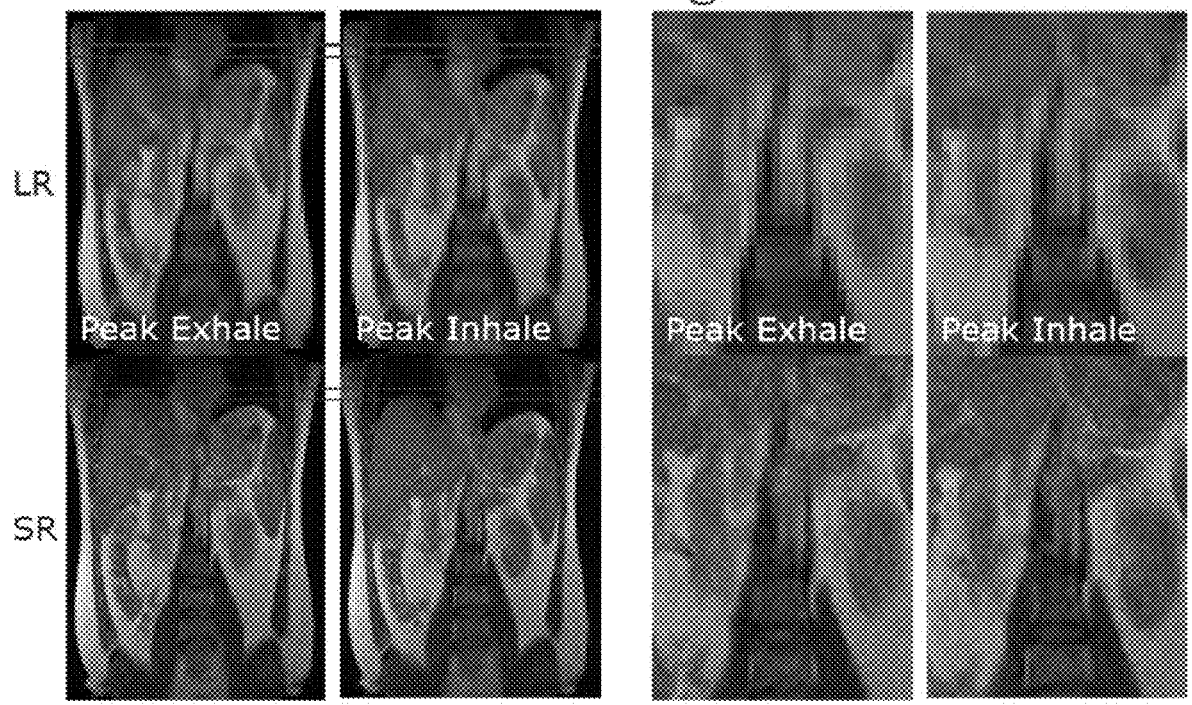
FIG. 15 is a series of images showing LR free-breathing MR images used as input images (top row) and corresponding HR MR images produced using a super-resolution generative (SRG) model based on the generative adversarial network (GAN) framework in accordance within an aspect of the disclosure (left) and using an existing MRI SR method (right).
Figure 16:
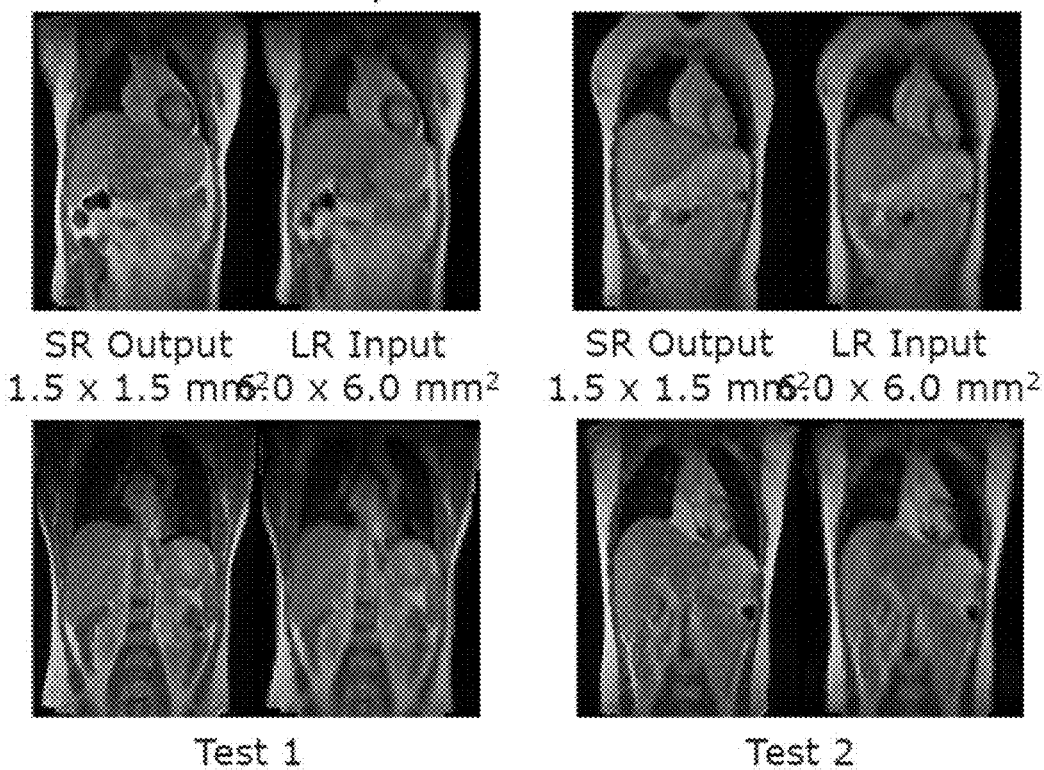
FIG. 16 is a series of images showing LR free-breathing MR images used as input images and corresponding HR MR images produced using a super-resolution generative (SRG) model based on the generative adversarial network (GAN) framework in accordance within an aspect of the disclosure.
Figure 32:
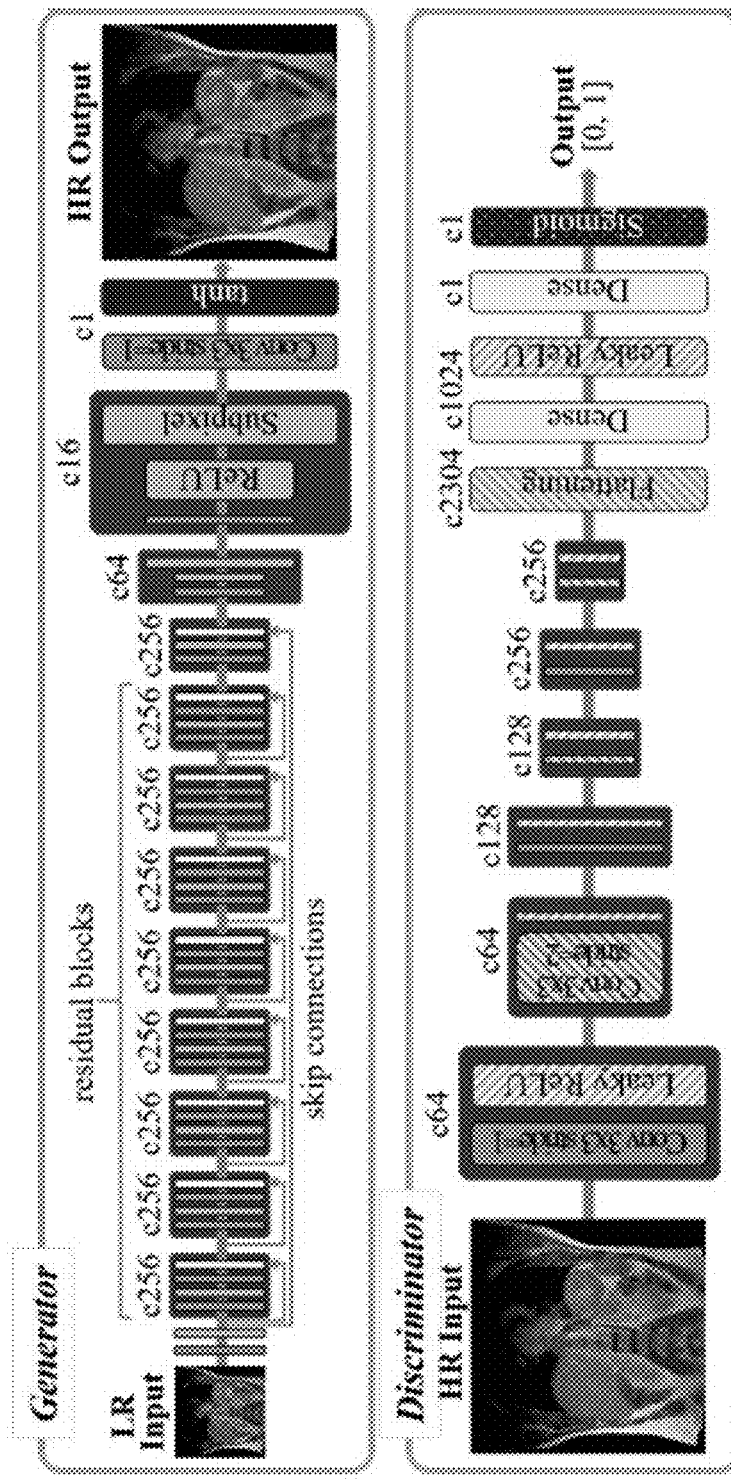
FIG. 32 contains block diagrams representing the network structures of the components of a super-resolution generative (SRG) model based on the generative adversarial network (GAN) framework in accordance within an aspect of the disclosure.

The network structure of the GAN-based SRG model in one aspect is illustrated in FIGS. 14 and 32. The generator includes a total of 12 layers including eight residual blocks, two up-sampling layers, and two output layers. Each of the residual blocks includes two 3×3 convolutional filters separated by a ReLU activation with an elementwise sum operator attached at the end of the layer. The output block includes a 3×3 convolutional filter, ReLU activation, and a subpixel operator. The subpixel operator aggregates the feature maps from LR space and builds the SR image in a single step. The discriminator includes 3×3 convolution layers and two 1D dense layers separated by a Leaky ReLU activation. In order to convert 2D residual features into 1D, a flattening operator is attached at the exit of the convolution layer.

Figure 10:
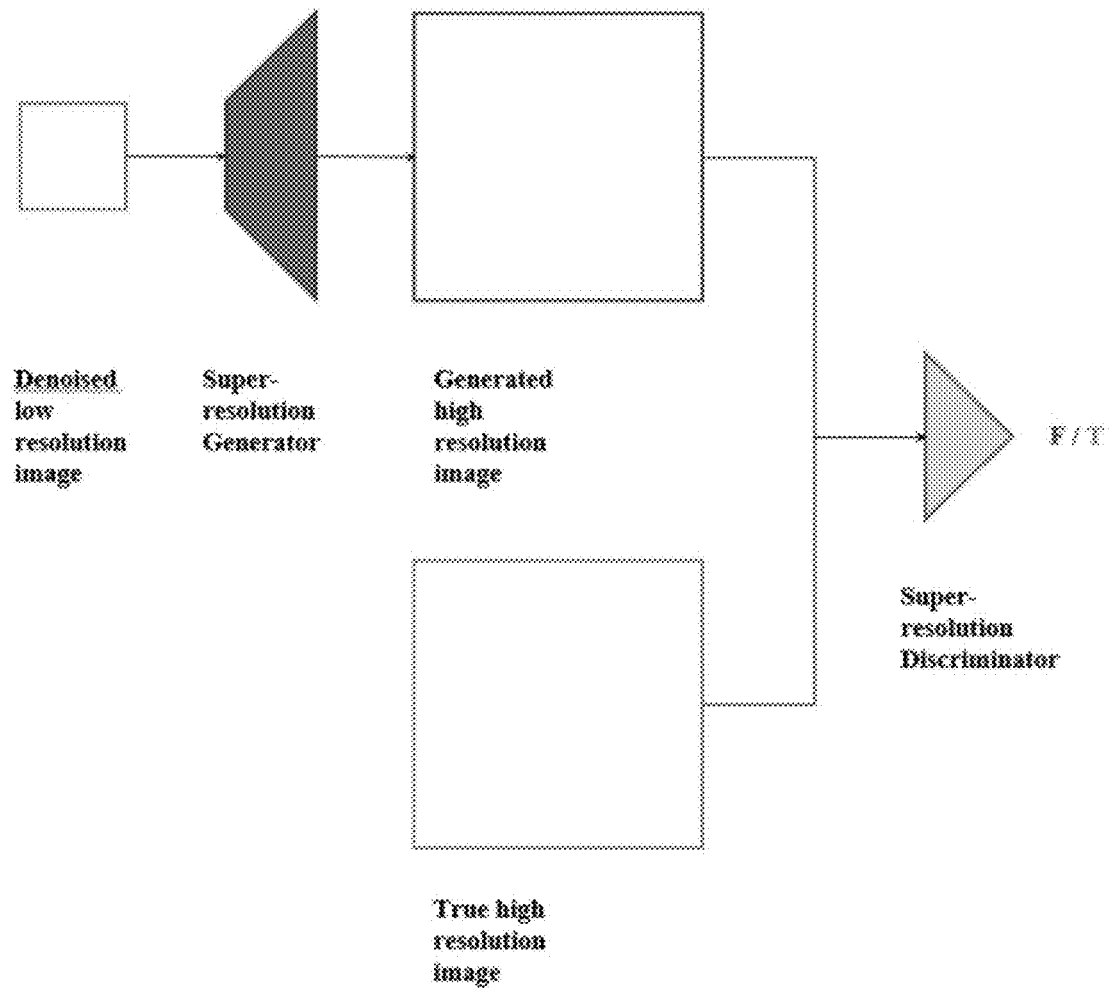
FIG. 10 is a schematic diagram illustrating the training framework of the 4DMR super-resolution convolutional network

In various aspects, the SRG model is trained to map reference LR MR images to reference HR images. Specifically, an HR image is constructed iteratively to best explain the given data set of LR images by minimizing the differences between the given HR images and the generated HR version of LR images fed into the network through the front end DAE (see FIG. 10). In various aspects, the SRG model is trained using LR/HR MR image pairs obtained using any method known in the art without limitation. However, as disclosed below, at least some of the existing methods of obtaining LR/HR MR image pairs used in network training do not realistically represent a LR MRI image as reconstructed from LR MR signals. In one aspect, a CNN-based method of transforming HR MR images into LR MR images using a down-sampling network (DSN) is used to obtain sufficient LR/HR MR image pairs for training the SRG model. A detailed description of the architecture and training methods for the DSN are described below.

e) Down-Sampling Network (DSN)

Existing deep-learning derived image super-resolution methods makes use of training data consisting of paired LR and HR MRI images to train the DL networks to transform LR MR images to HR MR images. In at least some cases, the training data is prepared by simulating LR MR images based on a known down-sampling method such as bicubic down-sampling as applied to HR MR image. However, without being limited to any particular theory, existing downsampling methods are not thought to fully represent the differences between LR and HR MRI images, because existing downsampling methods apply a transformation uniformly across a HR MRI image to produce the LR MRI image without accounting for any of the processes unique to the reconstruction of LR signals directly to produce a LR MR image. Ideally, this limitation could be addressed by obtaining matched LR/HR MR images clinically by imaging the same subjects using LR and HR MRI scanners, but it is infeasible to acquire sufficient numbers of training pairs in this manner.

In various aspects, the MRI SR method framed the task of producing HR MR images from LR MR images as a blind super-resolution problem. In one aspect, a downsampling neural network (DSN) is provided to transform HR MR images to corresponding LR MR images for use in training the MR SR network as described above. In this aspect, the size of the DSN is considerably smaller than the corresponding size of the SRG neural net described above, and therefore is trained with limited data, such as a small amount of paired low/high resolution MR images. In this aspect, the trained DSN is used to generate low resolution MR images from one or more clinical data sets which contain abundant high resolution MR images to form a full training set suitable for training the SRG network as described above.

As described above, the DSN infers LR MRIs from corresponding, abundant scans of clinical HR MRIs in order to maximize the number of training image pairs available to train the complex structured SRG network. Since the training data sets for the DSN require a perfect pairing of LR and HR MRIs that are limited in number, the DSN network in various aspects is designed to be simple while ensuring that the resulting inferred LR MR images reflect true LR scans acquired directly from LR MR scanners.

Figure 33:
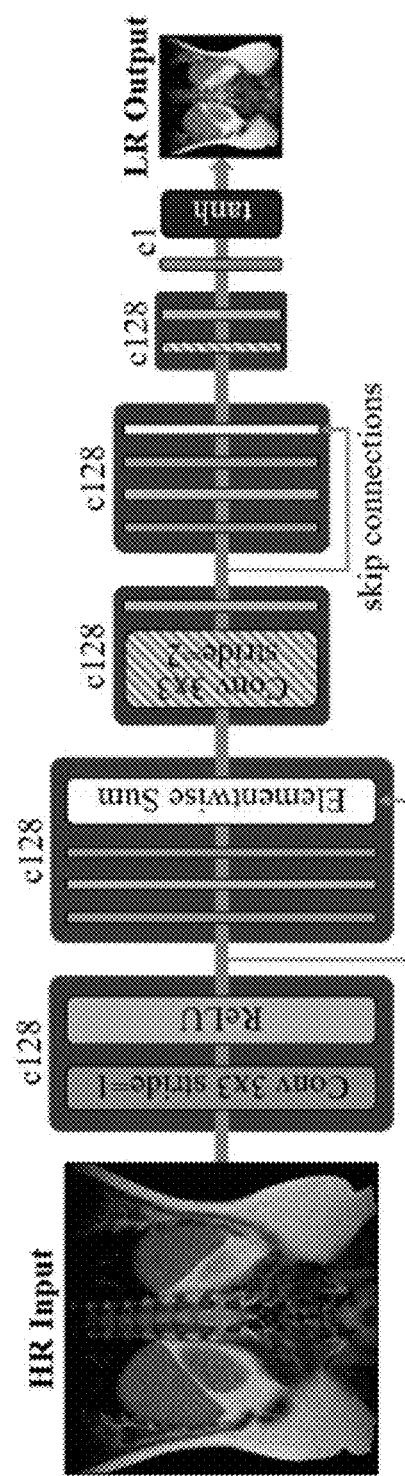
FIG. 33 contains block diagrams representing the network structures of the components of a down-sampling network (DSN) model in accordance within an aspect of the disclosure.

An overview of the structure of the DSN in one aspect is presented in FIG. 33. The DSN is a simple, single encoder that includes two down-sampling layers, two residual blocks, and an output layer. The down-sampling layer includes a single 3×3 convolutional filter of stride 2 followed by a ReLU activation. In each down-sampling layer, the dimensions of the output features are reduced by half of the original size. The residual block includes two 3×3 convolutional filters separated by a ReLU activation and followed by an elementwise sum operator that integrates the extracted features from the preceding down-sampling layer.

Training data for the DSN was collected from serial LR and HR scans of a phantom and volunteers acquired in a single breath-hold, resulting ultimately in 480 data pairs. Since the performance of the SRG model is highly dependent on the robustness of the DSN, we manually selected the data pairs to be used by rejecting or repetitively scanning the volunteers until the HR and LR scans were perfectly paired. The HR training data sets were cropped to a size of 192×192 pixels (1.5 mm×1.5 mm per pixel) with the corresponding output LR size of 48×48 pixels (6.0 mm×6.0 mm). Uncropped HR MRIs of 256×256 pixels (1.5×1.5 mm) and the corresponding LR images of 64×64 pixels (6.0×6.0 mm) were used in the testing and inferencing steps. The optimization of parameters during training was performed using the gradient descent method described above with the learning rate starting at 0.0002. The MAE L1 loss function defined in Eq. (4) was selected as the energy function to minimize at each epoch. The model was trained over 200 epochs using the GPU and 5-fold cross-validation was performed to test and demonstrate the robustness of the DSN.

After the DAE was trained from physically scanned LR MRI data, closely paired LR and HR MRIs that were acquired in a phantom and/or volunteers were selected to train the down-sampler. Manual down-sampling approaches that derived LR images from clinical HR MRIs were not capable of generating the realistic LR images that were directly reconstructed from the MRI system. Therefore, a CNN-based DSN characterized by a relatively small size and simple structure to learn the actual down-sampling process using a limited amount of paired LR and HR images acquired from a phantom or volunteers was used. In this manner, the large set of training data required to sufficiently train the SRG model was be prepared by applying the trained DSN to abundant clinical HR MRI scans.

II. Super Resolution MRI (MRI SR) DL Framework, Models, and Methods

Computed tomography (CT) and MRI images are widely used in medical applications either individually or in combination to noninvasively allow physicians to infer causes of abnormal function due to disease. CT and MRI are complementary techniques, each with their own strengths and weaknesses. CT offers accurate representation of patient geometry, is superior in visualization of bony anatomy, and CT values can be directly converted to electron density for radiation dose calculation. MRI is free of ionizing radiation and offers superior soft tissue contrast that allows more accurate structure delineation. It is therefore desirable to have a method that can derive CT-equivalent information from MRI images and vice versa, for the purpose of dose calculation, bony structure delineation, and soft tissue visualization.

In recent years, the exciting advances in machine learning has shown that deep Convolutional Neural Network (CNN) can accurately estimate synthetic CT images from MRI images. In previous studies, Mean Absolute Error (MAE) has been employed as a loss function in the network such that the network is trained to minimize differences between MR images and corresponding CT images. However, the drawback of using bare CNN is that it will generate blurry results due to the minimizing of MAE and will force the network to average plausible results.

Recently, Generative Adversarial Network (GAN) was introduced and has shown that the high frequency features of images can be restored much more efficiently compared to other CNN based methods. The GAN introduced the adversarial loss that comes from the discriminator that will drive the generated image to "look like" (according to the CNN) the real images rendering their shape and to have high frequency details.

As described in the present disclosure, a GAN based technique was developed to estimate CT images from corresponding MRI data and estimate MRI from a set of CT images.

In one aspect, the GAN-based algorithm can comprise the following steps:

(I) Training of Mapping Network:
  a. (i) Gather matched CT and MRI data sets of previously scanned patients. This data set should be acquired on the same/nearby days so that images were obtained with reproducible setup position.
  b. (ii) Perform Multi-modality Image Registration of two datasets. This registration enhances the performance/image quality of outcome since it is challenging to acquire perfectly matched datasets between CT and MR due to organ motion/shift during the scans.
  c. (iii) Train the GAN using two registered pairs.
(II) Mapping:
  a. (i) Acquire CT/MRI scan of a new patient.
  b. (ii) Insert the data into the trained network to generate CT→MRI I MRI→CT mapping.

One aspect of the present disclosure provides a method of generating a CT image from an MRI-based image or vice-versa using a deep convolutional generative adversarial network (DCGAN) model and vice-versa.

Another aspect of the present disclosure provides for the DCGAM model may be trained to map MRI-generated images from one state, such as T1-weighted, to another state, such as T2, and vice versa.

It is believed that the present gold standard for radiation therapy requires CT scans to calculate dosage (based on electron density) and MRI scans to visualize soft tissues. However, CT scans are harmful due to ionizing radiation, and the ability to completely eliminate CT is unique and highly desirable.

In addition, CT images are acquired only during the planning stage and are used repeatedly for electron density mapping on daily scanned MRI images. Since there may be daily changes in anatomy or patient positioning, this affects accuracy of dosage and targeting.

As described herein, is a machine learning based model that provides accurate estimation of corresponding images from one set of images, which eliminates the need for performing both MR and CT or multiple imaging sequences. The neural network (GAN) first learns the mapping between MR and CT images using a set of data that contains both MR and CT for the same patients where images can be registered. Once the GAN is trained it can generate CT from MRI images or vice versa. In addition, the GAN can be trained to register MR scans from different sequences and generate alternate images using a single set of images (see e.g., FIG. 4).

As described herein, the present disclosure provides for the development a method to provide accurate estimation of corresponding CT images from a set of MRI scans and vice versa. Currently in the clinic, there are often situations whereby both CT and MRI scans are required for accurate diagnosis as well as tumor localization during the course of radiation therapy. However, both images are not always readily available due to the fact that CT uses ionizing radiation which is harmful with frequent use and MRI has limited availability & accessibility in the clinic.

In various aspects, a machine learning (ML) based, deep convolutional generative adversarial network (DCGAN) model is provided that provides accurate mapping of MRI images from a set of CT scans and vice versa. In some aspects, the DCGAN model incorporates an atrous spatial pyramid pooling (ASPP) method, as described in additional detail below. With the use of the newly developed technology, the disclosed methods can provide (i) real-time mapping of CT images from a set of MRI scans; (ii) real-time mapping of MRI images from a set of CT scans; (iii) real-time mapping of MRI images of one state to another (e.g., T1 weighted to T2).

It is believed that the disclosed methods can increase the diagnostic capability in the field of Radiology as well as the therapeutic accuracy and workflow efficiency of MR-guided radiotherapy devices in Radiation Oncology.

The methods of the present disclosure do not require multiple imaging scans.

The methods described herein can use datasets (with both CT and MR) to train networks.

The methods described herein can use different datasets for different anatomical regions.

As described herein, the CT/MR images can be imaged in similar positions and close together in time.

a) Model and Loss Formulation

In various aspects, the task of sCT generation from MR images is viewed using the following formulation of a forward problem:

$$g = T(m) \qquad \text{Eq. (1B)}$$

where m is the input MR image data, T is the transformation operator that defines the mapping from MR to CT images, and g is the observable output of generated CT data.

Considering the one-to-many or many-to-one nature of mapping that arises due to similar MRI signal intensities in regions of bone and air, for example, determining the form of the operator T is non-trivial. The task is ill-posed and the goal in applying deep learning to the problem is to estimate a suitable operator $T_e$ such that a generic cost function C is minimized between the synthetic output $s = T_e(m)$ and the ground truth CT g:

$$\min_s C[s, g] \qquad \text{Eq. (2B)}$$

The GAN frameworks disclosed herein consist of two components, each of which is discussed in more detail below: 1) a generative model G that generates a sample in the data distribution $p_{data}$ in which true CT image data resides from a sample in a latent space and 2) a discriminator D that distinguishes whether a given sample is drawn from the data distribution or generated by G with a certain probability. The generator G and discriminator D undergo training in alternating minimization steps of their respective loss functions. In these frameworks, the generic cost minimization presented in Eq. 2B is the driving force of learning during the training process of the generator G. The discussion of the specific form of C[·] relies on the definition of sigmoid cross entropy loss:

$$L = \vec{z} * -\log(S(\vec{x})) + (1 - \vec{z}) * -\log(1 - S(\vec{x})) \quad \text{Eq. (3B)}$$

$$\text{with } S(\vec{x}) = \frac{1}{1 + \exp(-\vec{x})} \text{ simplifies}$$

$$\text{to} = \vec{x} - \vec{x} * \vec{z} + \log(1 + \exp(-\vec{x})),$$

where the elements of $\vec{x}$ are the true or predicted image logits computed by the discriminator D and $\vec{z}$ are the labels corresponding to true (1) or predicted (0).

The generative models discussed in the later sections share the same loss function $g_{loss}$ defined by:

$$g_{loss} = L_{adv} + 100 * l_{mae} \quad \text{Eq. (4B)}$$

ere the adversarial loss $L_{adv}$ is the sigmoid cross entropy loss (Eq. 3B) with predicted image logits $\vec{x}$ and labels $\vec{z} = \vec{1}$, a ones vector, and the mean absolute error (MAE) loss $l_{mae}$ is simply the mean of the absolute difference of the predicted images $I_{pred}$ and true images $I_{true}$:

$$l_{mae} = \text{mean}(|I_{pred} - I_{true}|) \quad \text{Eq. (5B)}$$

With this formulation, the complete loss function $g_{loss}$ penalizes predictions that are not computed as true data distributions by D through the adversarial loss term $L_{adv}$ and attempts to ensure pixel-wise agreement between predicted and true images with the MAE loss term $l_{mae}$. It should be noted that each term is reduced in dimensions by computing the mean before summing in Eq. 4B to yield a single value. The expressions herein are been simplified for brevity.

The aim of the discriminator D in the GAN framework differs from that of G, resulting in a loss function given by:

$$d_{loss} = L_{pred} + L_{true} \quad \text{Eq. (6B)}$$

where predicted loss $L_{pred}$ and true loss $L_{true}$ are each the sigmoid cross entropy loss (Eq. 3B) with predicted image or true image logits $\vec{x}$ computed by D and labels $\vec{z} = \vec{0}$ or $\vec{1}$, respectively. The formulation of $L_{pred}$ and $L_{true}$ in $d_{loss}$ differ from that of $L_{adv}$ in $g_{loss}$ (Eq. 4B) in that the labels corresponding to predicted image logits in $L_{adv}$ are unity, as G strives to produce sCT outputs that are evaluated as true CT images by D.

In various aspects, training G and D involves alternating minimization steps of each loss function, during which the parameters that define operations within each model are optimized. In one aspect, optimization for G is performed using the Adam gradient-based stochastic optimization algorithm with an initial learning rate of 0.0002, $\beta_1 = 0.7$, $\beta_2 = 0.999$, and $\hat{\epsilon} = 10^{-8}$. In another aspect, for optimizing D, TensorFlow's gradient descent optimizer is used with an initial learning rate of 0.00002. In each case, the learning rates decayed according to a staircase exponential function every 100000 steps with a base decay rate of 0.95 in an aspect.

b) Network Architectures

Figure 11:
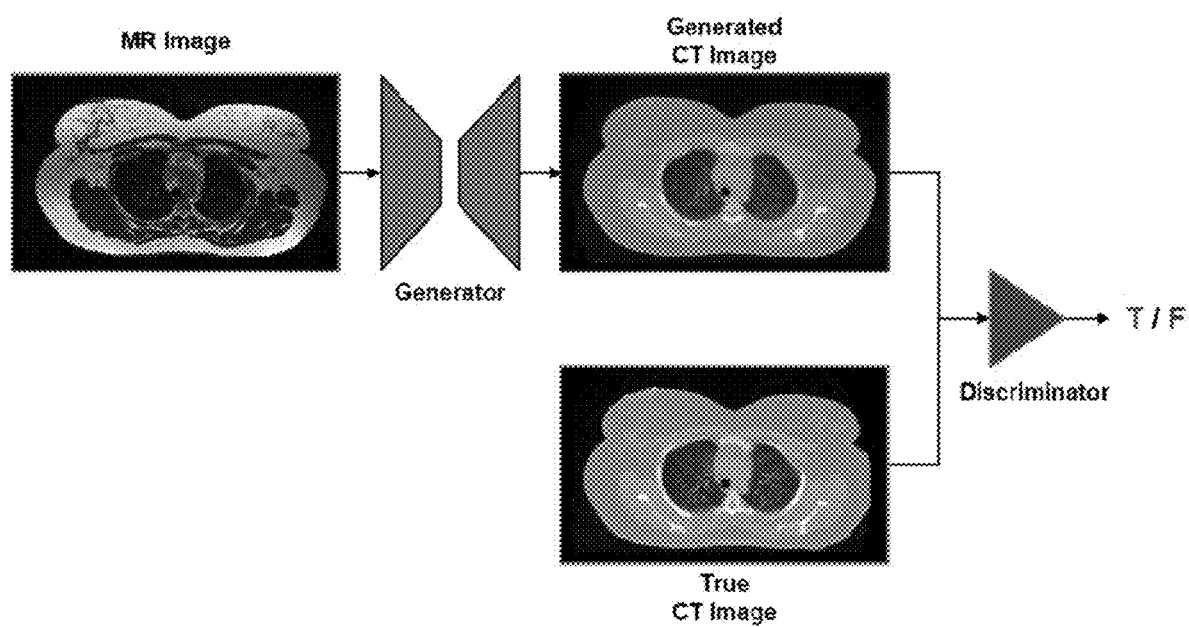
FIG. 11 is a schematic diagram illustrating the U-Net GAN framework comprises two CNNs: a generator and a discriminator. The generator produces a sCT image given an MR image input, which is then fed into the discriminator. The discriminator distinguishes between generated CT images and true CT images, reinforcing the training of the generator.

As described above, the GAN framework consists of two adversarial convolutional neural networks (CNNs). As illustrated schematically in FIGS. 4 and 11, the GAN framework for transforming MR images into pseudo-CT images includes two competing CNNs, a generative model G and a discriminator D, that are trained iteratively to improve the capabilities of each network. G in the GAN framework learns the mapping between MR and CT images, producing sCT outputs given an MR image input. The discriminator D then distinguishes whether a given CT image is drawn from the set of true CT images or is the product of G.

Figure 1:
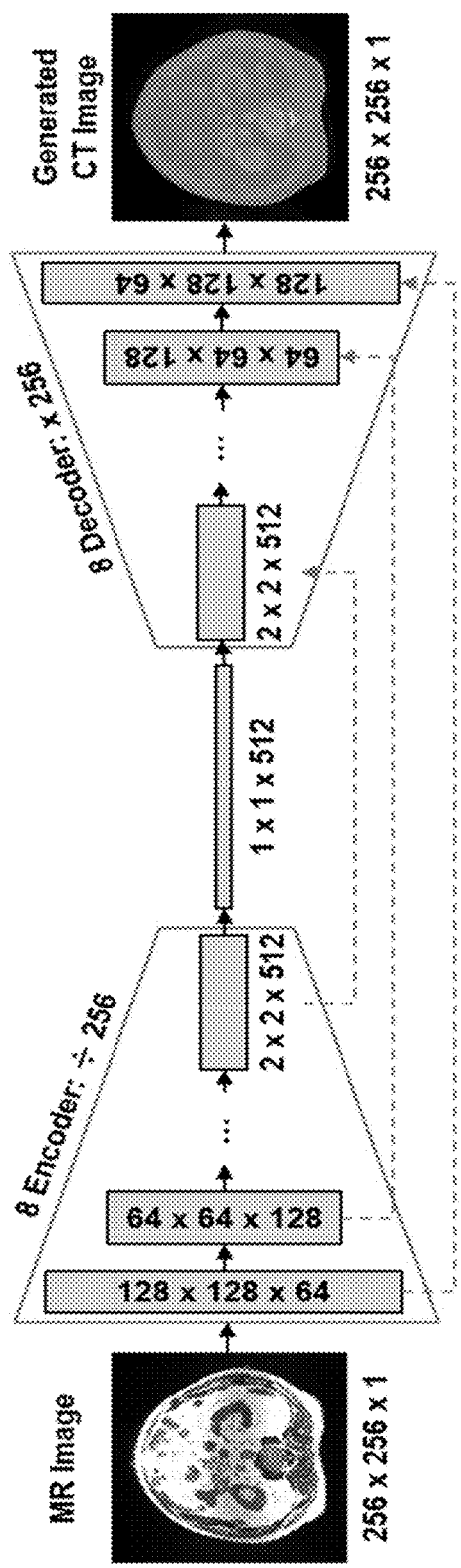
FIG. 1 is a block diagram showing the generative network G in the U-Net GAN framework consisting of a U-Net architecture of 8 stacked encoders/decoders in accordance with one aspect of the disclosure. Skip connections between corresponding layers (grey lines) allow for the transfer of shared structural features. The physical dimensions of the input are reduced 256 times as the image becomes represented by an increasing number of feature maps.
Figure 2:
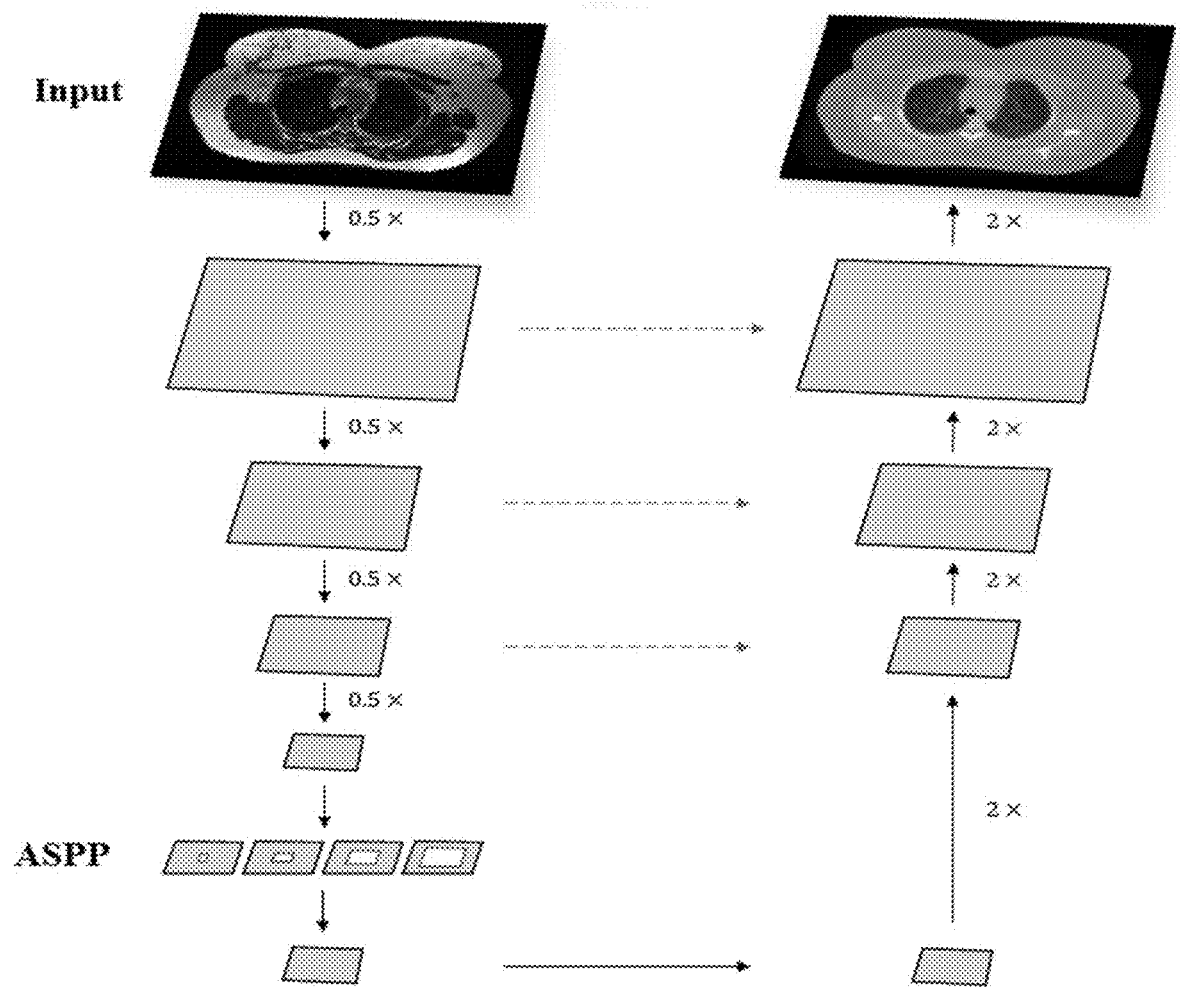
FIG. 2 is a schematic diagram of a modified U-Net+ASPP generator architecture that maintains the skip connections between corresponding layers in the encoder/decoder stack in accordance with one aspect of the disclosure. The application of ASPP eliminates the last four layers of the encoder and the first four layers of the decoder, simplifying the network while yielding richer structural information. At the ASPP stage, 3×3 convolutional filters are applied at increasing rates to capture contextual information with larger fields of view surrounding the pixel of interest. The physical dimensions of the input image are reduced by 16 times rather than 256 times, allowing for more flexibility in training the network.
Figure 3:
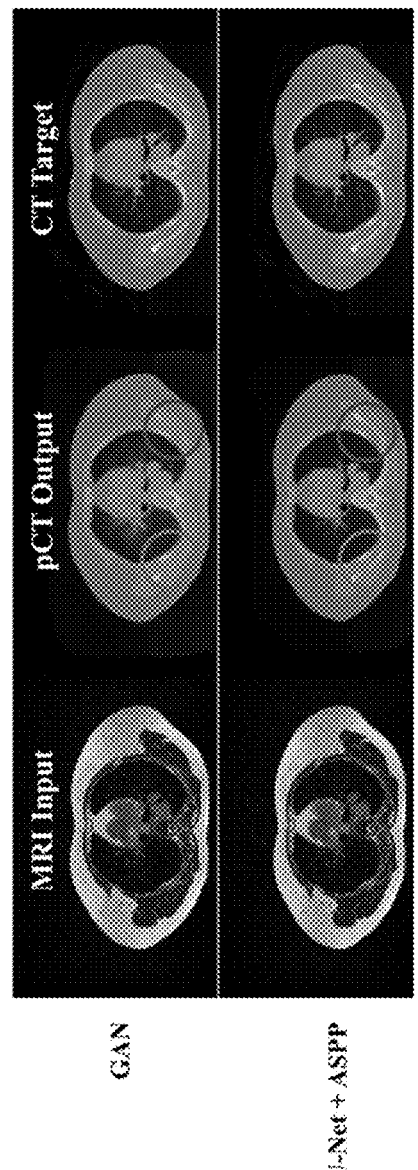
FIG. 3 contains a series of images showing an input MR (left), generated sCT (center), and true CT (right) images shown at one slice for a test patient for both the U-Net GAN framework (top) and the U-Net+ASPP architecture (bottom).
Figure 20:
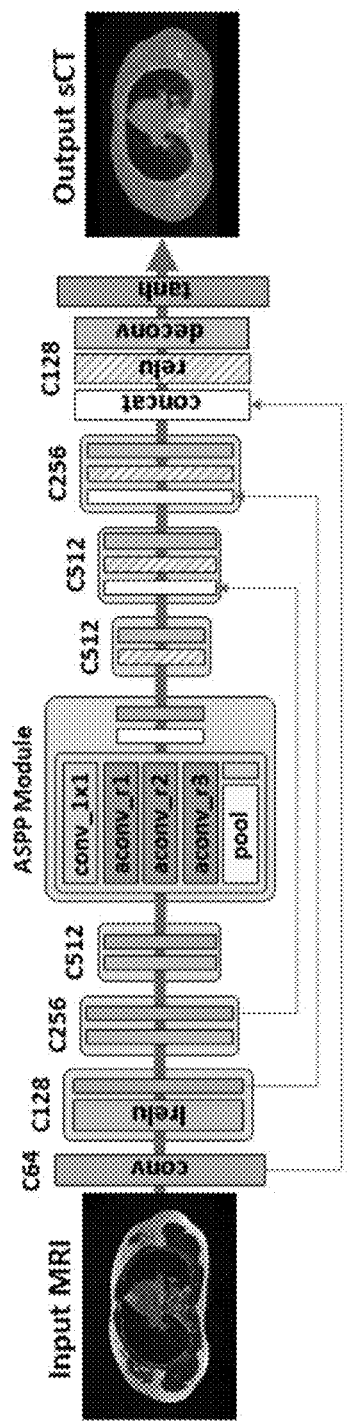
FIG. 20 is a schematic diagram illustrating aspp architecture in accordance with one aspect of the disclosure. Like in the U-Net pix framework, the input MR image is encoded as richer feature maps as it travels through the encoder side of the network. The ASPP module then applies five convolution operations in parallel before concatenation and another convolution. The decoder layers then recover spatial information as they up-sample the resulting feature maps and reconstruct the output sCT image.

In various aspects, the generative model G is provided in at least two forms: a conventional U-Net architecture implemented in a pix2pix framework referred to herein as "pix" (see FIGS. 1 and 17), and a deep spatial pyramid convolutional framework, referred to herein as "aspp" (see FIGS. 2 and 20). In various aspects, the discriminator D, the second half of the GAN framework, is of the same form in both implementations (see FIG. 21), as described in additional detail below.

i) Stacked Encoder-Decoder U-Net Generator—pix

Figure 17:
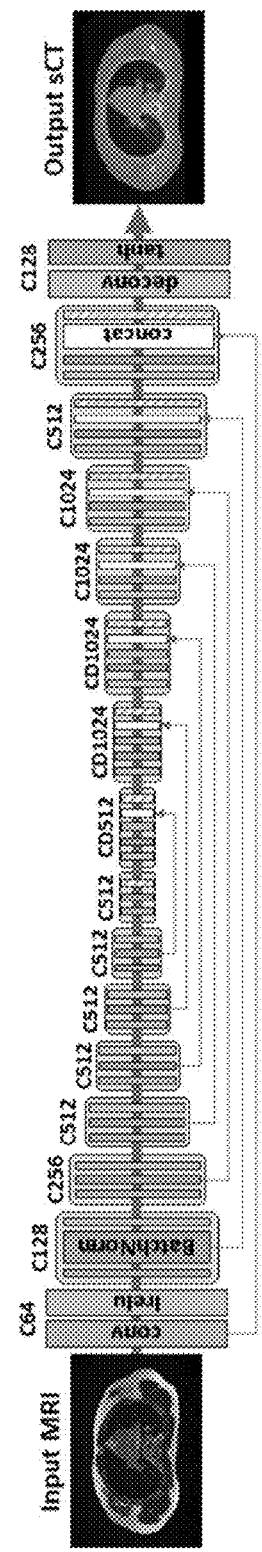
FIG. 17 is a schematic diagram illustrating the U-Net based pix architecture for transforming LR M images to sCT images. The input MR image is encoded sequentially as a feature map of reduced spatial dimension and increased depth as it travels through the encoder layers on the left side of the network. The process is reversed as the decoder layers recover spatial information and reconstruct the output sCT image. Skip connections between corresponding encoder/decoder layers, represented as grey lines at bottom here, allow shared structural features to move across the network efficiently.

In various aspects, the generative model G has a pix architecture, as illustrated in FIGS. 1 and 17, is a stacked encoder-decoder U-Net structure. In one aspect, the architecture of the encoder portion of the generative model G is characterized as C64-C128-C256-C512-C512-C512-C512-C512, and the decoder portion of the generative model G is characterized as CD512-CD1024-CD1024-C1021-C1024-C512-C256-C128, where Ck denotes a convolution-BatchNorm-ReLU layer with k convolutional filters with the exception of the first layer in the encoder in which batch normalization is not performed. In this aspect, the ReLUs on the encoder side of the network are leaky with a slope of 0.2. CDk denotes a convolution-BatchNorm-Dropout-ReLU layer with a dropout rate of 50%. The final layer in the decoder applies a convolution to map to the desired number of output channels (one here), followed by a hyperbolic tangent function. Each convolution is a 4×4 filter applied with a stride of 2. At each layer on the encoder side of the network, convolutions downsample by a factor of 2. On the decoder side, convolutions upsample by a factor of 2. Skip connections that share activations from a layer in the encoder with a corresponding layer in the decoder allow for the transfer of shared, underlying structural features like prominent edges from the input MRI to the generated sCT.

In total the pix architecture described above consists of 54,408,832 trainable parameters. These parameters, which include the weights and biases of the convolutional filters applied at each layer of the encoder and decoder, are updated at every training step according to the Adam stochastic optimization algorithm described above.

ii) Atrous Spatial Pyramid Pooling Generator: aspp

Figure 12:
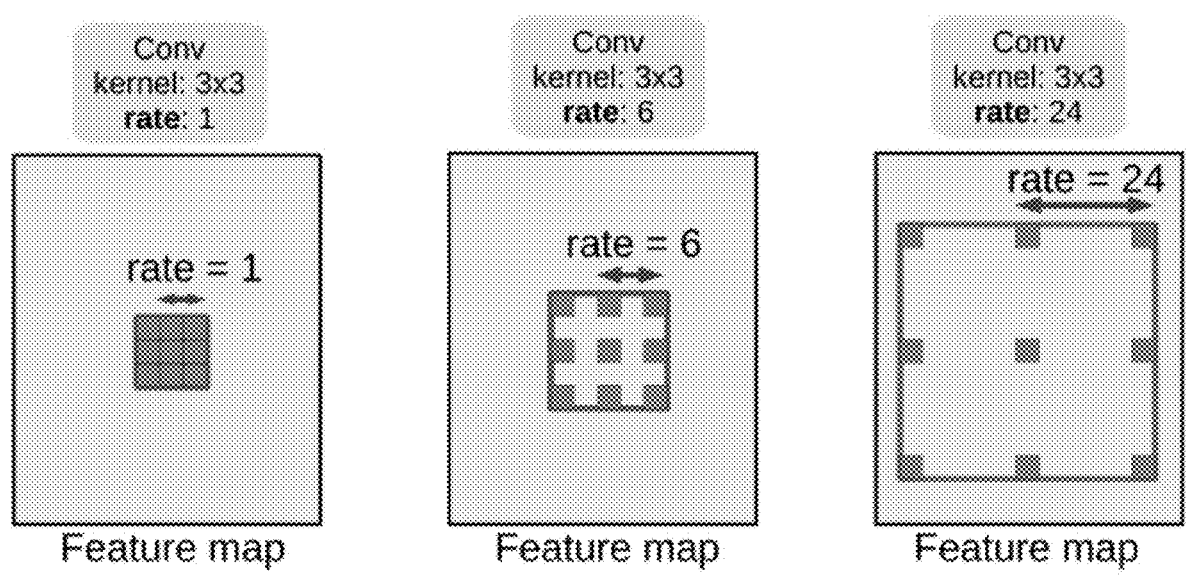
FIG. 12 is a schematic diagram illustrating atrous convolution with a 3×3 kernel and increasing rate. Increasing the rate widens the field of view, capturing context at a larger scale than standard convolution (rate=1).
Figure 18:
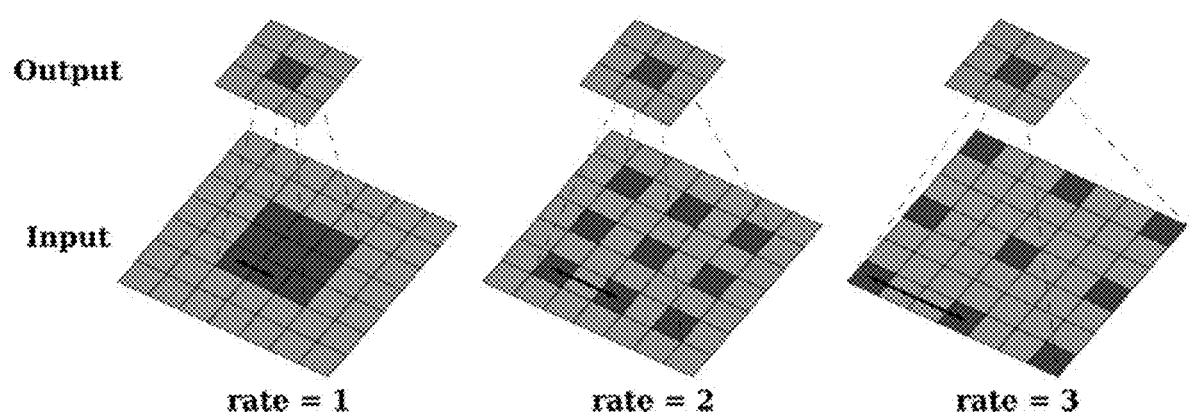
FIG. 18 is a schematic diagram illustrating atrous convolution applied to an input feature map with a 3×3 kernel and increasing rate. Increasing the rate widens the field of view without changing the size of the kernel, capturing context at a larger scale than standard convolution (rate=1).

In another aspect, the U-Net encoder-decoder architecture is modified using an Atrous Spatial Pyramid Pooling (ASPP) method, as illustrated in FIGS. 2 and 20. The ASPP method employs atrous or dilated convolution, shown illustrated in FIGS. 12 and 18, to encode multi-scale contextual information. Pixels included in the atrous convolution kernel are spaced away from the central pixel based on the rate of convolution, where larger rates correspond to a larger field of view for the convolution kernel without changing the size of the kernel.

Figure 13:
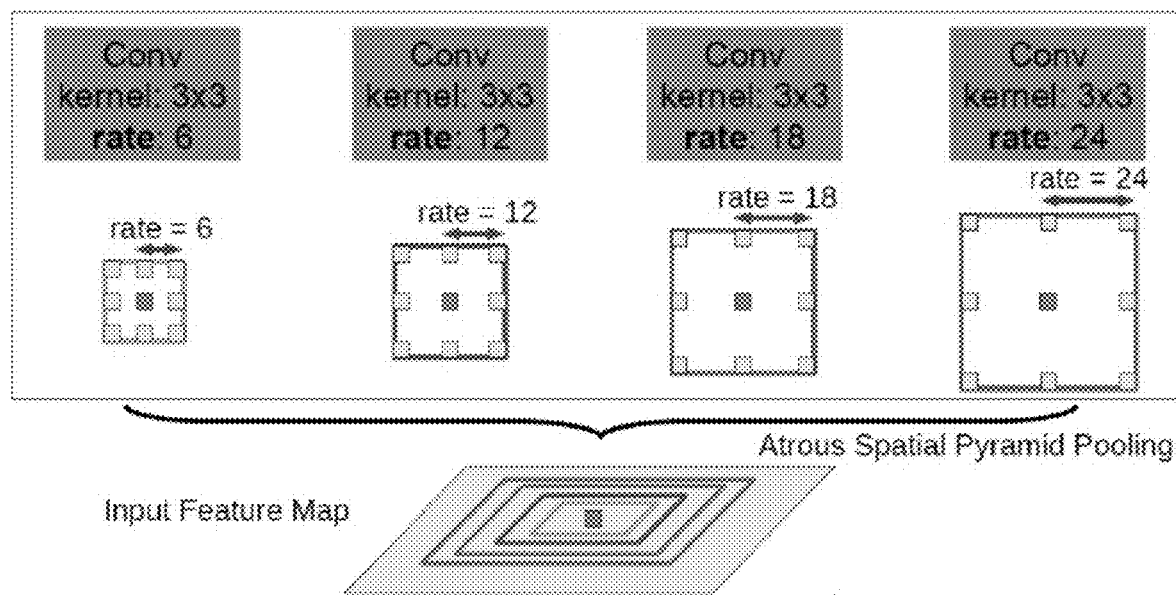
FIG. 13 is a schematic diagram illustrating the Atrous Spatial Pyramid Pooling (ASPP). Parallel convolutional filters of increasing rate capture contextual features at fields of view of increasing size, shown in different colors.
Figure 19:
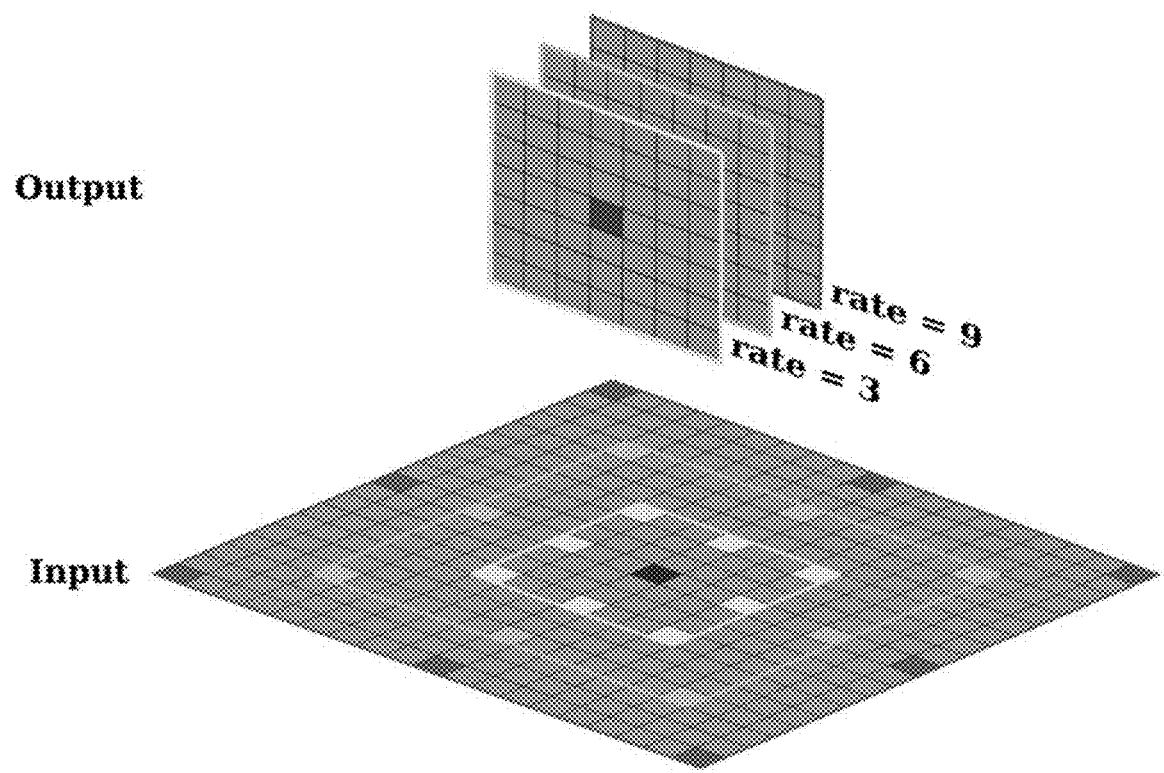
FIG. 19 is a schematic diagram illustrating the U-Net+ Atrous Spatial Pyramid Pooling (aspp architecture). Atrous convolution filters of increasing rate, shown in different colors, are applied in parallel to the input feature map. The resulting output feature maps that capture contextual features at fields of view of increasing size are concatenated together. For simplicity, output feature maps are not necessarily to scale and padding for convolution is not shown.

Without being limited to any particular theory, by performing atrous convolution at multiple rates in parallel, multi-scale features can be exploited to characterize a single pixel. As illustrated in FIGS. 13 and 19, an ASPP module in one aspect extracts contextual features from multiple fields of view, allowing the encoder to capture rich multi-scale information that aids in the image-to-image translation task.

Building from the pix generative framework described above, the ASPP module is implemented in a similar U-Net architecture as the pix architecture to create G in this aspect. The schematic diagram in FIGS. 2 and 20 illustrate the aspp network's structure. Similar notation to the notation used to characterize the pix structure as described above is used to characterize the aspp architecture, with addition of the annotation AC to denote atrous convolution. Using this notation, in one aspect, the encoder of the aspp network is characterized by C64-C128-C256-C512, the ASPP module is characterized by (C512, AC512 rate 3, AC512 rate 6, AC512 rate 9, average pool-C512)-C512, and the decoder is characterized by C512-C512-C256-C128.

In an aspect, all convolutions are 4×4 spatial filters with stride 2 (same as pix architecture) except for convolutions within the ASPP module. The four encoder layers that precede the ASPP module have an output stride of 16 compared to in the case of the 8 encoder layers in the pix framework. The ASPP module in this aspect consists of 5 convolution operations performed in parallel, all with stride 1: 1) 1×1 convolution; 2) 4×4 atrous convolution with rate 3; 3) 4×4 atrous convolution with rate 6; 4) 4×4 atrous convolution with rate 9; and 5) 1×1 convolution following an average pooling operation. In one aspect, the feature maps resulting from each of these convolution operations is concatenated before another set of 1×1 convolutional filters is applied. The successive decoder layers upsample the resulting feature maps to recover spatial information and construct the sCT output. As in the conventional pix framework, skip connections between corresponding encoder/decoder layers allow for the transfer of underlying structural features shared by the input and output images in this aspect.

In contrast to the pix framework described above, the elimination of 8 filter-dense layers from the interior of the network in favor of the ASPP module results in a significant reduction in the total number of trainable parameters from 54,408,832 for the pix architecture to 15,080,733 for the aspp architecture. In this aspect, the trainable parameters are updated during training by the Adam optimizer as described above.

iii) Discriminator

Figure 4:
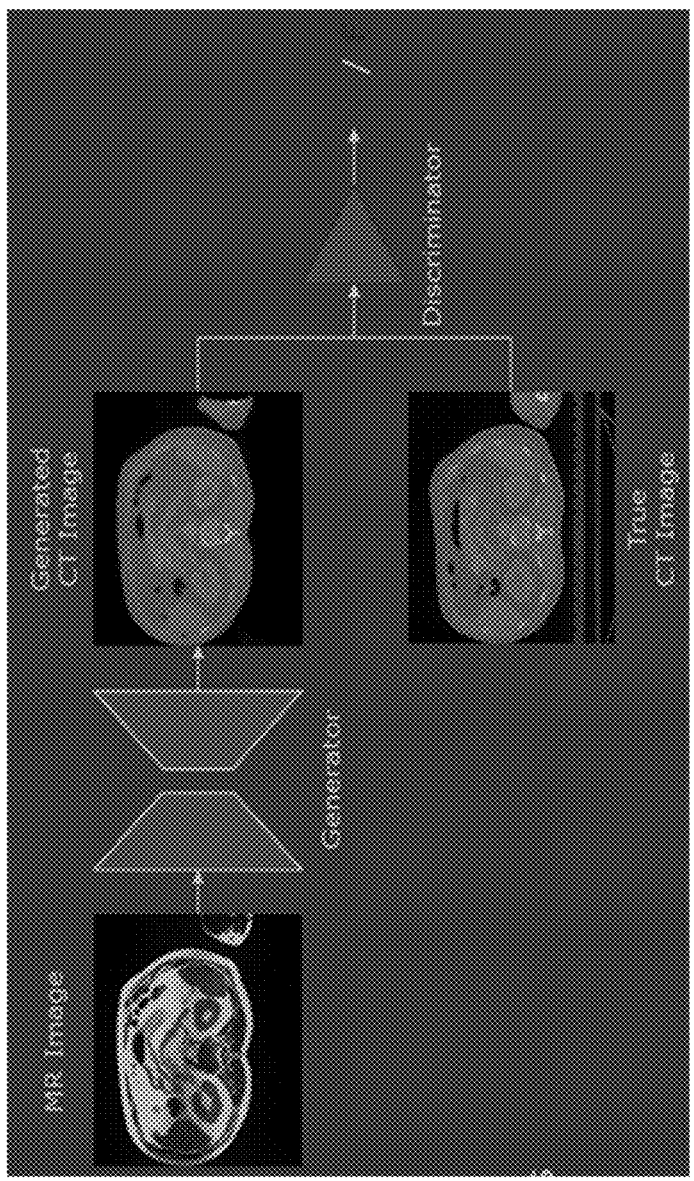
FIG. 4 is a diagram showing that the GAN can be trained to register MR scans from different sequences and generate alternate images using a single set of images.
Figure 21:
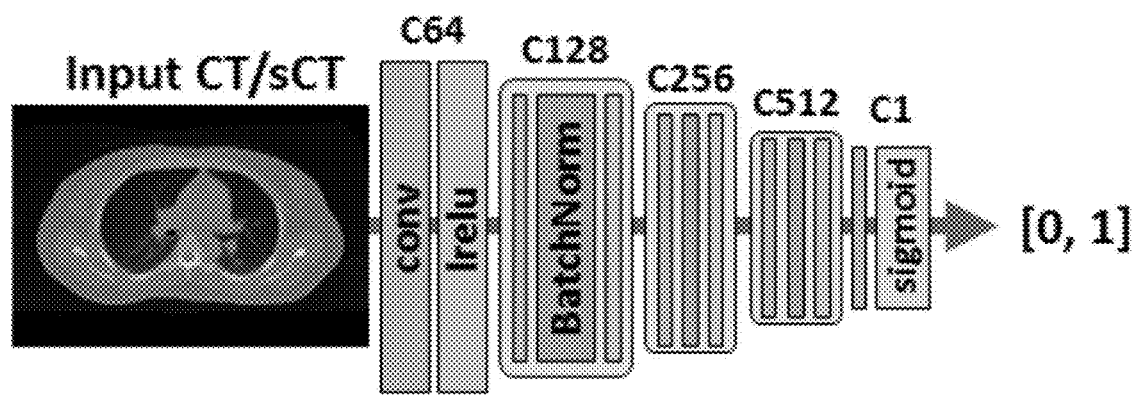
FIG. 21 is a schematic diagram illustrating the discriminator (D) architecture shared in each GAN framework. An input CT or sCT is encoded as a set of feature maps before being mapped to one channel by the last convolution operation. The sigmoid function is applied to yield values between zero and one that denote the probability that the input image is a true CT image.

In various aspects, the GAN network structure include one of the generator architectures described above (pic or asp) as well as a discriminator architecture (see FIG. 4). In various aspects, a single discriminator architecture is compatible or use in a GAN implementation that includes either the pic or the aspp generator architecture. The architecture of the discriminator D in one aspect is shown illustrated in FIG. 21. Using the same notation as described above in characterizing the generator architectures, the structure of the discriminator D in this aspect is characterized as C64-C128-C256-C512 with the exception of the first layer, where no batch normalization is performed. Also in this aspect, leaky ReLUs are utilized with slope 0.2. As illustrated in FIG. 21, following the last layer, a final convolution is applied to map to one channel before applying a sigmoid function. In various aspects, the range of values produced by the discriminator D range from zero to one. In various aspects, the value of the discriminator output denotes the probability that the input image (a CT image produced by the generator G) is a true CT image The result is values between zero and one that denote the probability that the input image is a true CT image. Thus, a discriminator output value of zero denotes that the input image is likely a sCT image produced by the generator and a discriminator output value of one denotes that the input image is a true sCT image drawn from a pool of sCT images. In the discriminator D architecture described above and illustrated in FIG. 21, the total number of trainable parameters is 2,763,520.

III. MRI-Guided Radiation Treatment Systems, Devices, and Methods

In various aspects, the MRI SR networks and methods are combined with the ASPP+UNet GAN-based networks and methods are combined and integrated with radiation treatment planning system to produce an MR-guided radiation planning system used to plan and administer radiation therapy to a patient. As described above, the MRI SR networks and methods enable the production of high resolution MR images based on low resolution MR images obtained from the clinical scanner at relatively fast scanning rates. As also described above, the ASPP+UNet GAN-based networks and methods transform MR images into sCT images that are essentially indistinguishable from clinical CT images obtained by clinical CT scanners. A complete workflow based solely on MRI can eliminate image registration uncertainties for combining MRI with CT and thereby reduce clinical workload. With our technique, CT can be derived from the corresponding MRI for dose calculation and DRR-based patient positioning and hence could potentially eliminate the use of CT during radiation therapy planning workflow. This would also eliminate patient exposure to radiation during the treatment planning process.

In MRI-guided-daily-adaptive radiation therapy (MRgART), CT images acquired during the simulation stage is repeatedly used for electron density mapping on daily scanned MRI which does not account for daily changes in anatomy. With our technique, CT images can be derived from daily scanned MRI images and hence, provide electron density information with increased accuracy for daily adaptive planning process during MRgART.

In diagnostic radiology, CT delivers geometrically accurate three-dimensional visualization of anatomy. However, soft tissue contrast and tumor delineation capabilities are poorer than with MRI. With our technique, MRI can be estimated from the corresponding CT images. Hence, it is possible to provide the needed information without use of MRI. Also, the disclosed technique on estimating CT from MRI can be used for attenuation correction and to enhance bony anatomy information on the newly developing PET-MRI hybrid system.

In various aspects, a MR image guided radiation treatment system includes a computing device that includes a processor and a memory. The memory contains a plurality of modules, and each module contains at least one instruction executable on the processor. In various aspects, the plurality of modules includes a MRI SR network module that includes instructions that, when executed by the processor, implement the MRI SR methods described above.

In brief, the MRI SR network module receives low resolution MR data, denoises the low resolution MR data using a de-noising autoencoder (DAE) model to produce de-noised low resolution MR data as described above. The MRI-SR module further transforms the low resolution MR data to at least one high resolution MR image using a super-resolution generative model (SRG).

In various other aspects, the plurality of modules further include an aspp generative network module that transforms a high resolution MR image produced by the SRG model, into a pseudo-CT (sCT) image as described above. Because the sCT image is derived directly from the MR image, sCT and MR images are intrinsically registered, thereby reducing the uncertainties associated with MR/CT image registration associated with existing MR-guided radiation treatment systems.

In various additional aspects, the plurality of modules further include an imaging device control module configured to operate the MR scanner to obtain the low resolution MR images described above. In various other additional aspects, the plurality of modules further include a radiation treatment planning module and/or a radiation treatment control module. The radiation treatment planning module is configured to produce a radiation treatment plan based on the sCT and high resolution MR images received from the aspp generative network module and MRI SR network modules, respectively and using any suitable radiation treatment planning method known in the art without limitation. The radiation treatment control module is configured to operate a radiation treatment device to administer a radiation treatment according to a radiation treatment plan produced by the radiation treatment planning module and using any suitable radiation treatment control or administration method known in the art without limitation.

Computing Systems

Figure 29:
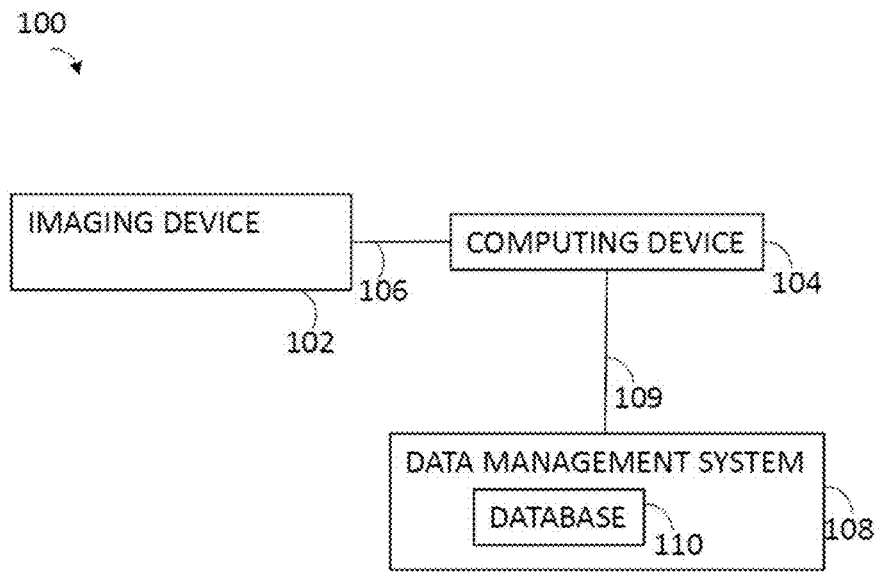
FIG. 29 is a block diagram showing an imaging system in accordance with an aspect of the disclosure.
Figure 30:
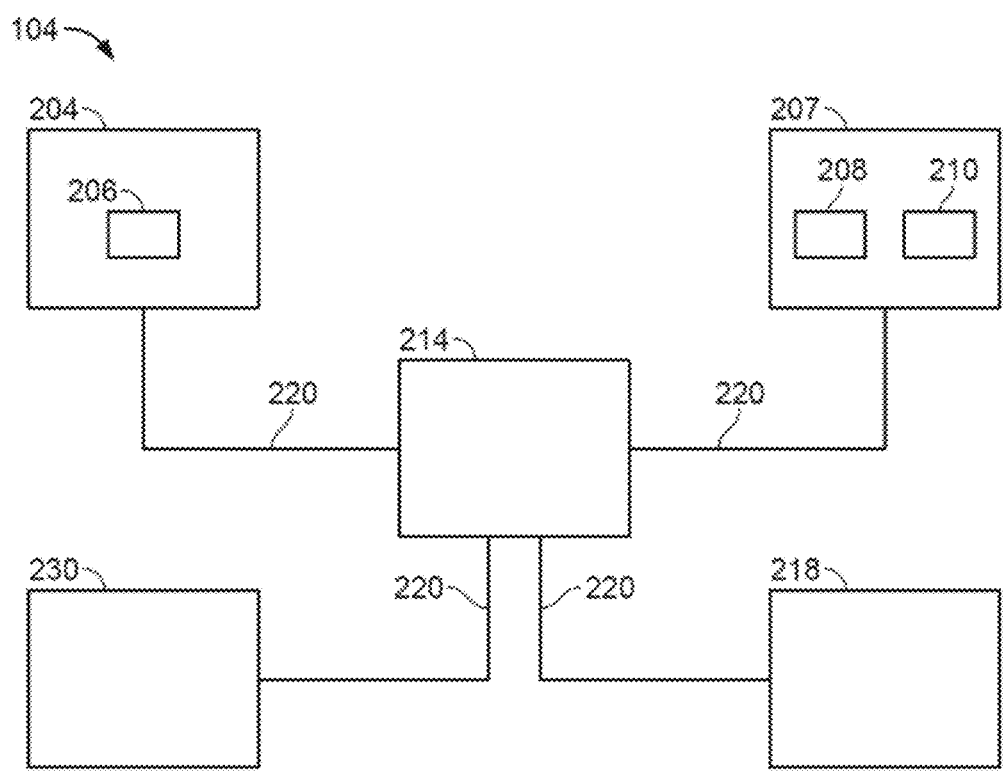
FIG. 30 is a block diagram illustrating a computing device in accordance with an aspect of the disclosure.

In various aspects, the disclosed methods may be implemented using a computing device as part of an imaging system. As seen in FIG. 29, system 100 includes an imaging device 102 that is configured to acquire imaging data of target region positioned within a body region of a subject. A subject as used herein is a human (live or deceased), an animal (live or deceased), an organ or part of an organ of a human or an animal, or part of a human or an animal. For example, a subject may be a breast, a part of a human that includes an ovary or a cervix, or part of a human that includes a lesion or part of a lesion. The imaging device may be a PET, PET/CT, or PET/MRI scanner.

Although, in some of the examples provided below, the systems and methods disclosed herein are used on certain part of the body or certain types of lesions, the systems and methods are not limited to that part of human or animal body or that type of lesions.

Referring again to FIG. 29, system 100 also includes a computing device 104 coupled to imaging device 102 via a data conduit 106. It should be noted that, as used herein, the term "couple" is not limited to a direct mechanical, electrical, and/or communication connection between components, but may also include an indirect mechanical, electrical, and/or communication connection between multiple components. Imaging device 102 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, New York. WIMAX is a registered trademark of WiMax Forum, of Beaverton, Oregon. BLUETOOTH is a registered trademark of Bluetooth SIG, Inc. of Kirkland, Washington.

Referring again to FIG. 29, computing device 104 is configured to receive imaging data from the imaging device 102. The computing device 104 may be configured to control the imaging device 102. The computing device may include a number of components which perform specific tasks including, but not limited to, a processor, a data storage device and/or a communication component. In one aspect, the data storage device is configured to store data received or generated by computing device, such as any of the data stored in a database or any outputs of processes implemented by any component of the computing device. In another aspect, the communication component is configured to enable communications between the computing device and other devices over a network or a plurality of network connections using predefined network protocols such as TCP/IP (Transmission Control Protocol/Internet Protocol).

In other aspects, the processor is configured to execute instructions received from a storage device. In some aspects, executable instructions may be stored in the storage device. The processor may include one or more processing units (e.g., in a multi-core configuration). The storage device may be any device allowing information such as executable instructions and/or other data to be stored and retrieved. In one aspect, the computer readable instructions, when executed on a processor, may provide a user interface to the user via the media output component. The user interface may further receive and process input from the input device. The user interface may include, but is not limited to, a web browser and an application. The storage device may include one or more computer-readable media.

In some aspects, the processor may be operatively coupled to a storage device via a storage interface. The storage interface may be any component capable of providing the processor with access to storage device. Non-limiting examples of suitable storage interfaces include an Advanced Technology Attachment (ATA) adapter, a Serial ATA (SATA) adapter, a Small Computer System Interface (SCSI) adapter, a RAID controller, a SAN adapter, a network adapter, and/or any component providing the processor with access to the storage device.

Non-limiting examples of storage devices include random access memory (RAM) such as dynamic RAM (DRAM) or static RAM (SRAM), read-only memory (ROM), erasable programmable read-only memory (EPROM), electrically erasable programmable read-only memory (EEPROM), and nonvolatile RAM (NVRAM).

The computing device may also include at least one media output component for presenting information to a user. The media output component may be any component capable of conveying information to the user. In some aspects, the media output component may include an output adapter, such as a video adapter and/or an audio adapter. The output adapter may be operatively coupled to the processor and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, the media output component may be configured to present an interactive user interface (e.g., a web browser or client application) to the user.

In some aspects, the computing device may include an input device for receiving input from the user. The input device may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of the media output component and the input device.

The computing device may also include a communication interface, which may be communicatively coupleable to a remote device. The communication interface may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

System 100 further includes a data management system 108 that is coupled to computing device 104 via a network 109. In some embodiment, the computing device 104 includes a data management system 108. Data management system 108 may be any device capable of accessing network 109 including, without limitation, a desktop computer, a laptop computer, or other web-based connectable equipment. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of lesion region of other subjects. Database 110 can also include any additional information of each of the subjects that enables system 100 to function as described herein.

In various embodiments, data management system 108 communicates with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

Embodiments of the disclosure may be described in the general context of computer-executable instructions, such as program modules, executed by one or more computers or other devices. The computer executable instructions may be organized into one or more computer executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer executable instructions or components having more or less functionality than illustrated and described herein. Aspects of the disclosure may also be practiced in distributed computing environments where tasks are performed by remote processing devices that are linked through a communications network. In a distributed computing environment, program modules may be located in both local and remote computer storage media including memory storage devices.

The computer systems, computing devices, and computer implemented methods discussed herein may include additional, less, or alternate actions and/or functionalities, including those discussed elsewhere herein. The computer systems may include or be implemented via computer executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above. For example, a ML module may receive training data comprising customer identification and geographic information and an associated customer category, generate a model which maps customer categories to customer identification and geographic information, and generate a ML output comprising a customer category for subsequently received data inputs including customer identification and geographic information.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In one aspect, a ML module receives unlabeled data comprising customer purchase information, customer mobile device information, and customer geolocation information, and the ML module employs an unsupervised learning method such as "clustering" to identify patterns and organize the unlabeled data into meaningful groups. The newly organized data may be used, for example, to extract further information about a customer's spending habits.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Deep Learning-Based Non-Iterative Low-Dose CBCT Reconstruction for Image Guided Radiation Therapy In image guided radiation therapy (IGRT) settings, cone-beam computed tomography (CBCT) system using kilovoltage (kV) x-ray source is the most widely-used imaging devices.

CBCT uses ionizing x-ray for imaging therefore, there is a legitimate concern about hazardous radiation exposure to the patient.

Hence minimizing the imaging dose is desirable based on ALARA principle.

The most common way in low-dose CBCT application is the 'model-based image reconstruction technique' which is computationally heavy and time consuming due to its iterative nature.

In this study, we disclose a deep learning-based low-dose CBCT reconstruction technique that utilizes standard analytical reconstruction technique (i.e. FDK).

Instead of constructing the model within the reconstruction domain, we formulated this problem as restoring high quality high-dose projection (100 kVp, 1.6 mAs) from corresponding noisy low-dose projection(100 kVp, 0.1 mAs) via trained neural network.

Methods
CBCT: Experiment 4 sets of fully paired (High-dose & Low-dose) CBCT projections of Rando H&N phantom were acquired (i.e. Center-aligned, 2 cm shifted in lateral (right), anterior and inferior directions.).

2 sets for training, 1 set for validation and 1 set for testing

Figure 5:
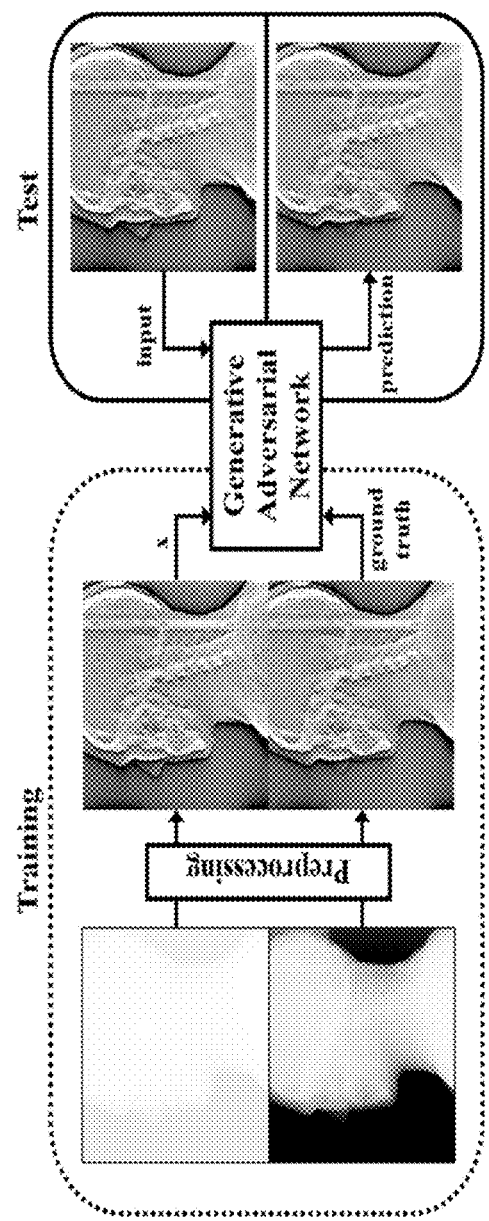
FIG. 5 is a diagram of GAN framework during training. Paired low and high dose projection data is fed into the generator, which estimated high dose projection outputs. Generated and real high dose projections are then fed into the discriminator.

Prior to the training, all of images were filtered to eliminate low-frequency information which is not necessary for analytical reconstruction (FIG. 5).

Deep Learning: Network Architecture

The restoration of CBCT projection was performed using generative adversarial network (GAN) which is a convolutional neural net framework that consists of two models (FIG. 5):

Generator: produces high-dose projection outputs based on pairs of low and high dose image inputs.

U-net architecture: The 8 encoder and decoder layers are connected at each level by skip connections that allow for the transfer of high resolution features, aiding image reconstruction.

Discriminator: determines if a given high-dose image is drawn from the true distribution of high-dose images or generated by the other network.

Consists of 5 convolutional layers.

For evaluation, the trained model was applied to unseen phantom data that was placed randomly on the couch.

The restored high-dose projection was reconstructed using simple back-projection method.

Results

Training on 700 image-pairs took approximately 16 hours to complete using Nvidia GTX 1080.

PseudoCTs are produced by the trained model with a throughput time of approximately 80 projections/second.

Figure 6:
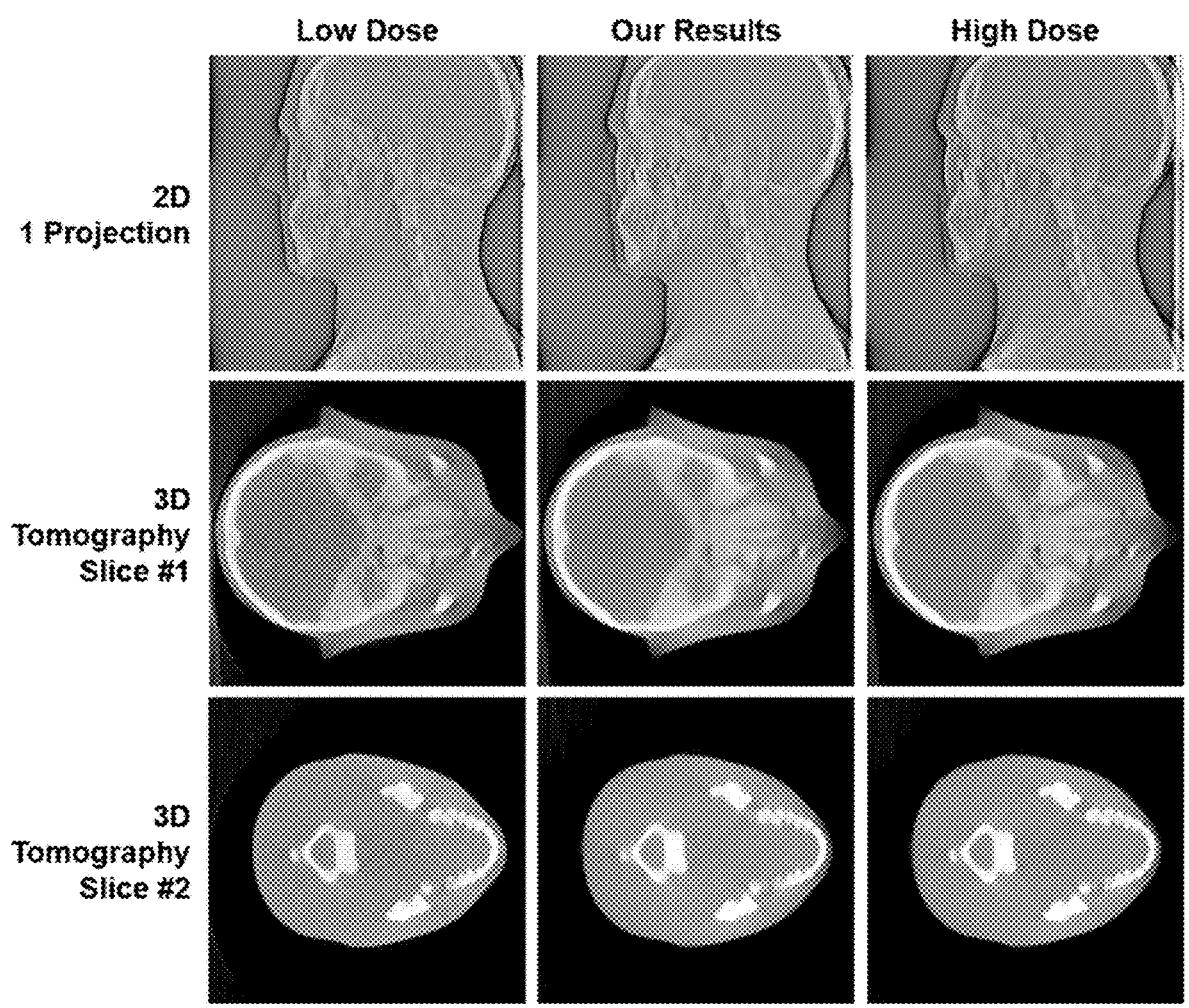
FIG. 6 contains a series of images illustrating the result of reconstruction using a head phantom.

Significant noise reduction was achieved compared to original input while maintaining the quality comparable to the CBCT of high-dose projections (FIG. 6).

TABLE 1

| Experimental Environment | |
| --- | --- |
| CBCT System | Elekta XVI 5.0 |
| Phantom | Rando H&N |
| High-dose Projection | 100 kVp, 1.6 mAs |
| Low-dose Projection | 100 kVp, 0.1 mAs |

Conclusion

The disclosed deep learning-based method for CBCT reconstruction offers the ability to reduce the imaging dose without addition of reconstruction time.

This makes our approach potentially useful in an on-line image-guided radiation therapy.

Example 2: Validation of De-Noising Auto-Encoder (DAE) for MRI SR Network

To validate the accuracy of the DAE described above, the following experiments were conducted.

A DAE network similar to the DAE network illustrated in FIG. 31 was trained using 480 LR breath-hold images. All data used in this study were acquired from a commercially available MR-IGRT system (ViewRay Inc., Oakwood Village, Ohio) that integrated a split-bore 0.35 T whole body MRI system with a three head Co-60 radiation therapy delivery system. MRIs of the patients and volunteers were acquired using torso phased array receiver coils. Both breath-hold 3D and free breathing 3D cine (or 4D) volumetric images in three orientations (transverse, sagittal, and coronal) were acquired using the 3D true fast imaging with steady-state precession (TrueFISP) sequence. The generalized auto calibrating partially parallel acquisition (GRAPPA) technique was used to accelerate image acquisition.

An NLM filter was utilized to obtain the noise-free LR images noted by $\mu$ in Eq. (3) described above. Instead of directly training the DAE network based on the noisy observations and the corresponding denoised LR images that were less robust due to the insufficient amount of data, training samples were generated through adding noise to the preprocessed images. Without being limited to any particular theory, noise in an MRI is typically governed by a Rician distribution, and is nearly Gaussian if the SNR>2. In one aspect, Rician noise was utilized to generate the noisy MR images in one aspect.

Parameter optimization during training was performed using the stochastic gradient descent method (Adam Optimizer) embedded in TensorFlow with a leaning rate starting at 0.0002. The training is performed over 200 epochs using a GeForce GTX 1080 Ti GPU (NVIDIA, Santa Clara, CA). 5-fold cross-validation was performed to test and demonstrate the robustness of the DAE.

Figure 34:
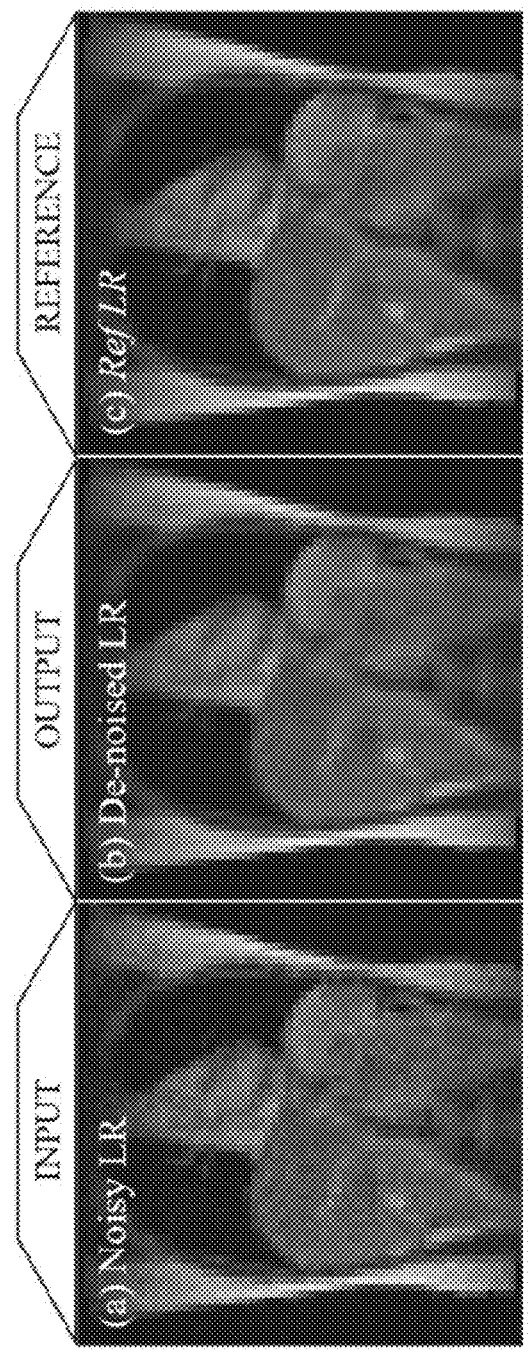
FIG. 34 contains a series of images comparing a noisy low-resolution image, a low-resolution MR image de-noised using a DAE network, and a reference noise-free low resolution image.

FIG. 34 displays the reference de-noised LR MRI (right image), the de-noised output of the DAE (center image), and the noisy input (left image). As can be seen in FIG. 34, DAE reproduced image quality that was comparable to the reference de-noised image without major structural loss.

To evaluate the performance of the DAE more comprehensively, the peak signal-to-noise ratio (PSNR), structural similarity index (SSIM), and normalized root mean square error (RMSE) indexes were used as quantitative measures. Values of the PSNR, SSIM, and normalized RMSE calculated for the DAE outputs and noisy inputs over 5 validation folds are summarized in Table 2 below. Manually denoised images (de-noised with the NLM filter) were used as the reference for each of the 480 image pairs. For the noisy input, the measured values were 33.4 dB (PSNR), 0.90 (SSIM), and 0.022 (RMSE), whereas for the DAE outputs the results were consistently improved by 8.4%, 6.5% and 31.8%, measuring 36.5, 0.96 and 0.015 respectively.

TABLE 2

Statistics for values of PSNR, SSIM, and RMSE computed over 5 validation folds for 480 noisy and DAE-generated de-noised data.

|  | Noisy | | | De-noised | | |
|---|---|---|---|---|---|---|
|  | PNSR | SSIM | RMSE | PSNR | SSIM | RMSE |
| Mean | 33.4 | 0.900 | 0.022 | 36.5 | 0.963 | 0.015 |
| Std | 0.3 | 0.037 | 0.001 | 1.2 | 0.010 | 0.002 |
| Min | 32.9 | 0.770 | 0.019 | 34.3 | 0.918 | 0.009 |
| Median | 33.3 | 0.910 | 0.022 | 36.3 | 0.965 | 0.015 |
| Max | 34.6 | 0.950 | 0.023 | 41.1 | 0.979 | 0.019 |

Example 3: Validation of Down-Sampling Network for MRI SR Network

To demonstrate and validate the robustness of the DSN, the following experiments were conducted.

Training data for the DSN were collected from serial LR and HR scans of a phantom and volunteers acquired in a single breath-hold, resulting in 480 data pairs. Since the performance of the SRG model is highly dependent on the robustness of the DSN, the data pairs to be used were manually selected by rejecting or repetitively scanning the volunteers until the HR and LR scans were perfectly paired. The HR training data sets were cropped to a size of 192×192 pixels (1.5 mm×1.5 mm per pixel) with the corresponding output LR size of 48×48 pixels (6.0 mm×6.0 mm). Uncropped HR MRIs of 256×256 pixels (1.5×1.5 mm) and the corresponding LR images of 64×64 pixels (6.0×6.0 mm) were used in the testing and inferencing steps.

The optimization of parameters during training was performed using the gradient descent method as described above with the learning rate starting at 0.0002. The MAE L1 loss function defined in Eq. (4) was selected as the energy function to minimize at each epoch. The model was trained over 200 epochs using the GPU and 5-fold cross-validation was performed to test and demonstrate the robustness of the DSN.

FIGS. 35A, 35B, 35C, 35E, 35F, 35G, 35H, and 35I illustrate the down-sampled result of the DSN described above (FIG. 35B and FIG. 35G) compared with the manual down-sampling methods: k-space down-sampling (FIG. 35C and FIG. 35H), bicubic interpolation (FIG. 35D and FIG. 35I), and nearest neighborhood sampling (FIG. 35E and FIG. 35J)) used to generate LR and HR image pairs for training the SRG model described above. LR images from MRI pairs were physically scanned during a single breath-hold and used as the ground truth reference (FIG. 35A). Referring to FIG. 35G, the difference between the proposed DSN-generated LR and the ground truth reference LR images (FIG. 35G) was much less than the difference observed for the manual down-sampling methods (FIGS. 35H, 35I, and 35J).

Figure 36:
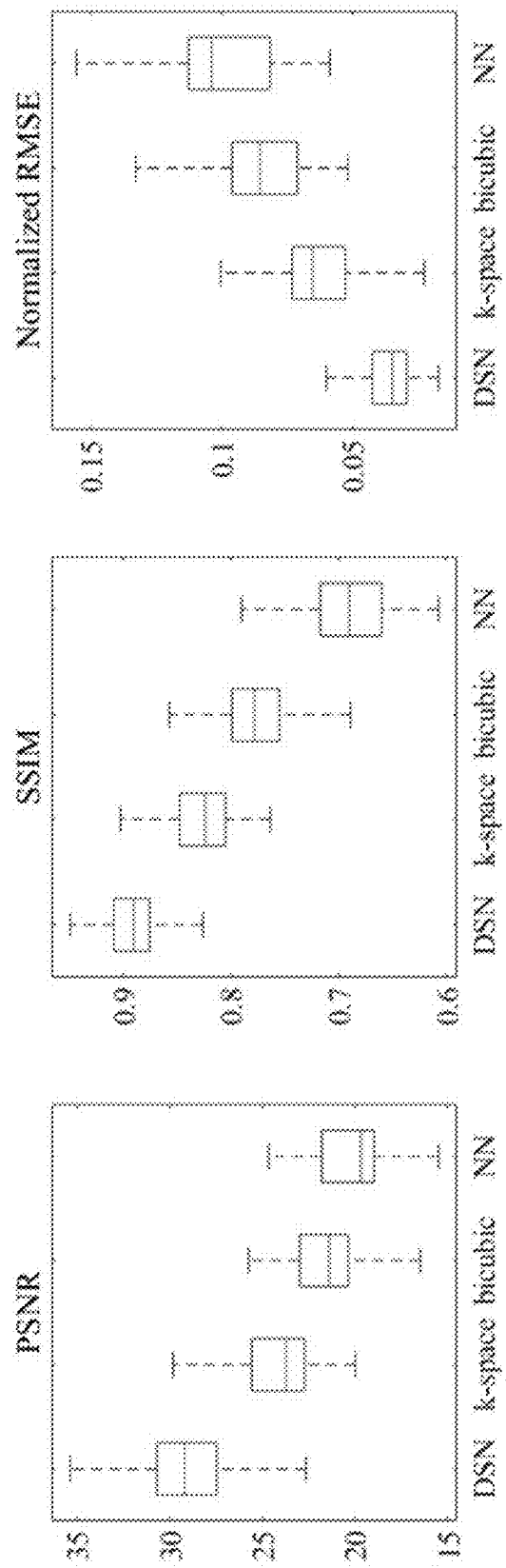
FIG. 36 is a box plot summarizing 7 5-fold cross-validation results of PSNR, SSIM, and normalized RMSE for the 480 outputs of four down-sampling approaches: DSN, k-space down-sampling, bicubic down-sampling, and nearest neighbor (NN) down-sampling. LR images acquired from physical scans served used as the reference.

Box plots displayed in FIG. 36 summarize the statistics over 5-fold cross-validation for the calculated values of PSNR, SSIM, and normalized RMSE for the DSN-generated LR images compared to the manually down-sampled LR images, with LR MRIs acquired from physical scans were used as the reference. These statistics are also presented in Table 3 below. The values of 24.4 dB (PSNR), 0.826 (SSIM), and 0.062 (RMSE) were observed for k-space down-sampling—the most accurate method amongst the conventional down-sampling methods. For the DSN, the results were consistently improved by 19.7%, 7.8%, and 74.7%, measuring 29.2, 0.891, and 0.036 respectively.

TABLE 3

Statistics of computed values of PSNR, SSIM, and RMSE for 480 outputs of the proposed DSN, k-space down-sampling, bicubic down-sampling, and nearest neighbor down-sampling.

|  | DSN | | | k-space | | | Bicubic | | | Nearest Neighbor | | |
|---|---|---|---|---|---|---|---|---|---|---|---|---|
|  | PSNR | SSIM | RMSE | PSNR | SSIM | RMSE | PSNR | SSIM | RMSE | PSNR | SSIM | RMSE |
| Mean | 29.2 | 0.891 | 0.036 | 24.4 | 0.826 | 0.062 | 21.6 | 0.777 | 0.086 | 20.2 | 0.691 | 0.100 |
| Std | 2.2 | 0.027 | 0.009 | 2.5 | 0.029 | 0.015 | 2.1 | 0.036 | 0.021 | 1.9 | 0.038 | 0.021 |
| Min | 22.3 | 0.795 | 0.017 | 20.0 | 0.763 | 0.019 | 15.6 | 0.665 | 0.052 | 15.5 | 0.607 | 0.059 |
| Median | 29.2 | 0.890 | 0.035 | 23.7 | 0.824 | 0.065 | 21.4 | 0.778 | 0.085 | 19.7 | 0.690 | 0.104 |
| Max | 35.4 | 0.919 | 0.077 | 34.4 | 0.902 | 0.100 | 25.7 | 0.857 | 0.166 | 24.7 | 0.790 | 0.168 |

Example 4: Validation of Super-Resolution Generative Model (SRG) for MRI SR Network on 3D Low Resolution Breath-Hold MRI Scans To validate the accuracy of the SRG of the MRI SR network described above, the following experiments were conducted.

Figures 37A, 37B:
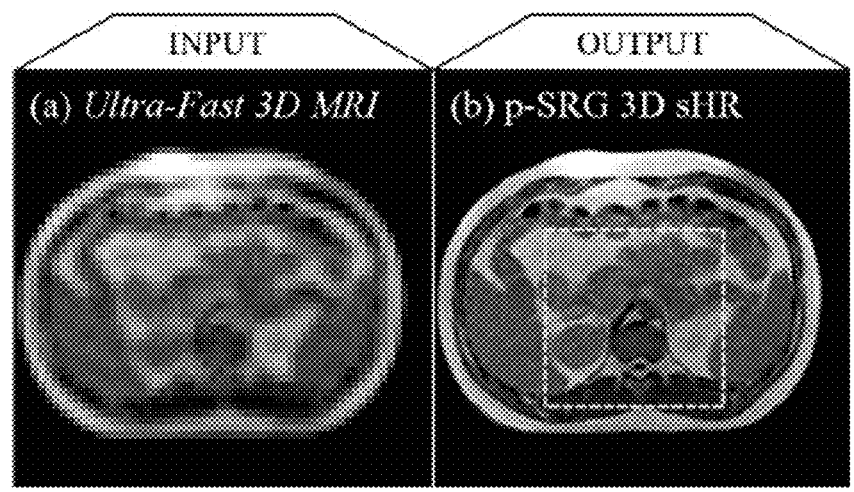
FIG. 37A is a low resolution (LR) axial 3D breath-hold MRI image obtained from a physical scan (3 sec/vol, 64×64 pixels, 6.0 mm×6.0 mm per pixel) used as input for an SR reconstruction in accordance with one aspect of the disclosure.
FIG. 37B is an image output (256×256 pixels, 1.5 mm×1.5 mm per pixel) from an SRG process in accordance with an aspect of the disclosure.
Figures 37C, 37D:
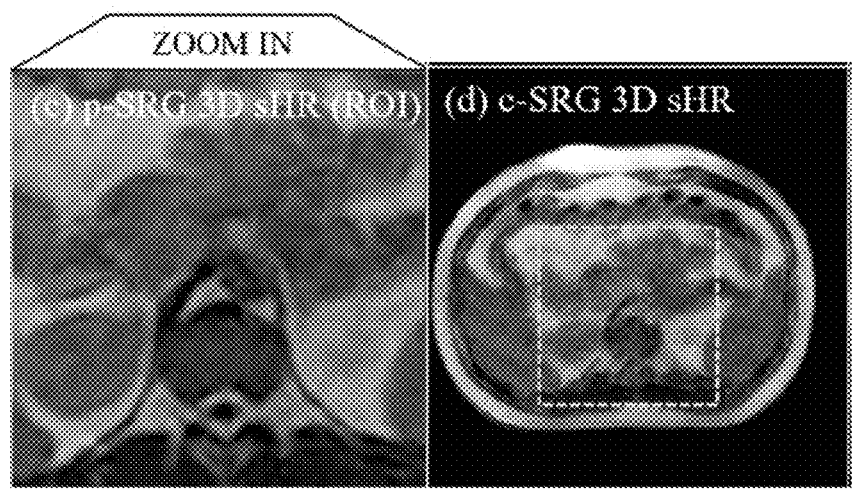
FIG. 37C is an enlarged image of the area bounded by a superimposed rectangle within the image of FIG. 37B.
FIG. 37D is an image output (256×256 pixels, 1.5 mm×1.5 mm per pixel) from a conventional SRG process
Figure 37E:
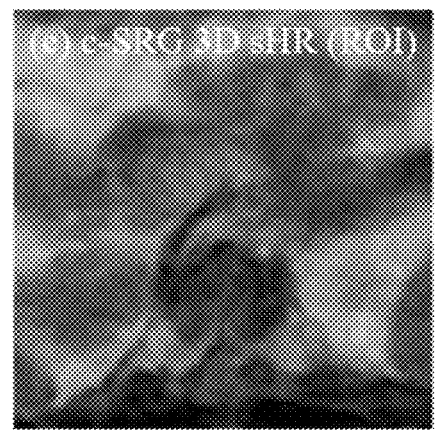
FIG. 37E is an enlarged image of the area bounded by a superimposed rectangle within the image of FIG. 37D.

High resolution MR images based on 3D LR breath-hold MRI scans were obtained using a conventional SRG model and using the MRI SR framework as described above, including the SRG described above. Results for the SR reconstruction of 3D LR breath-hold MRI scans (FIG. 37A) are shown for the MRI SR framework described above (FIGS. 37B and 37C) as well as a conventional SRG model (FIGS. 37D and 37E). Visually improved image quality was observable for the output of the SRG model from the MRI SR framework described above (FIGS. 37B and 37C) compared to that of the conventional SRG model (FIGS. 37D and 37E). Upon closer inspection, it is also observed that the boundaries of the vertebral body and the right kidney structure in the MRI SR's SRG output (FIG. 37C)) are clearly distinctive, while both structures are blurred in the convention SRG output (FIG. 37E).

Figure 38:
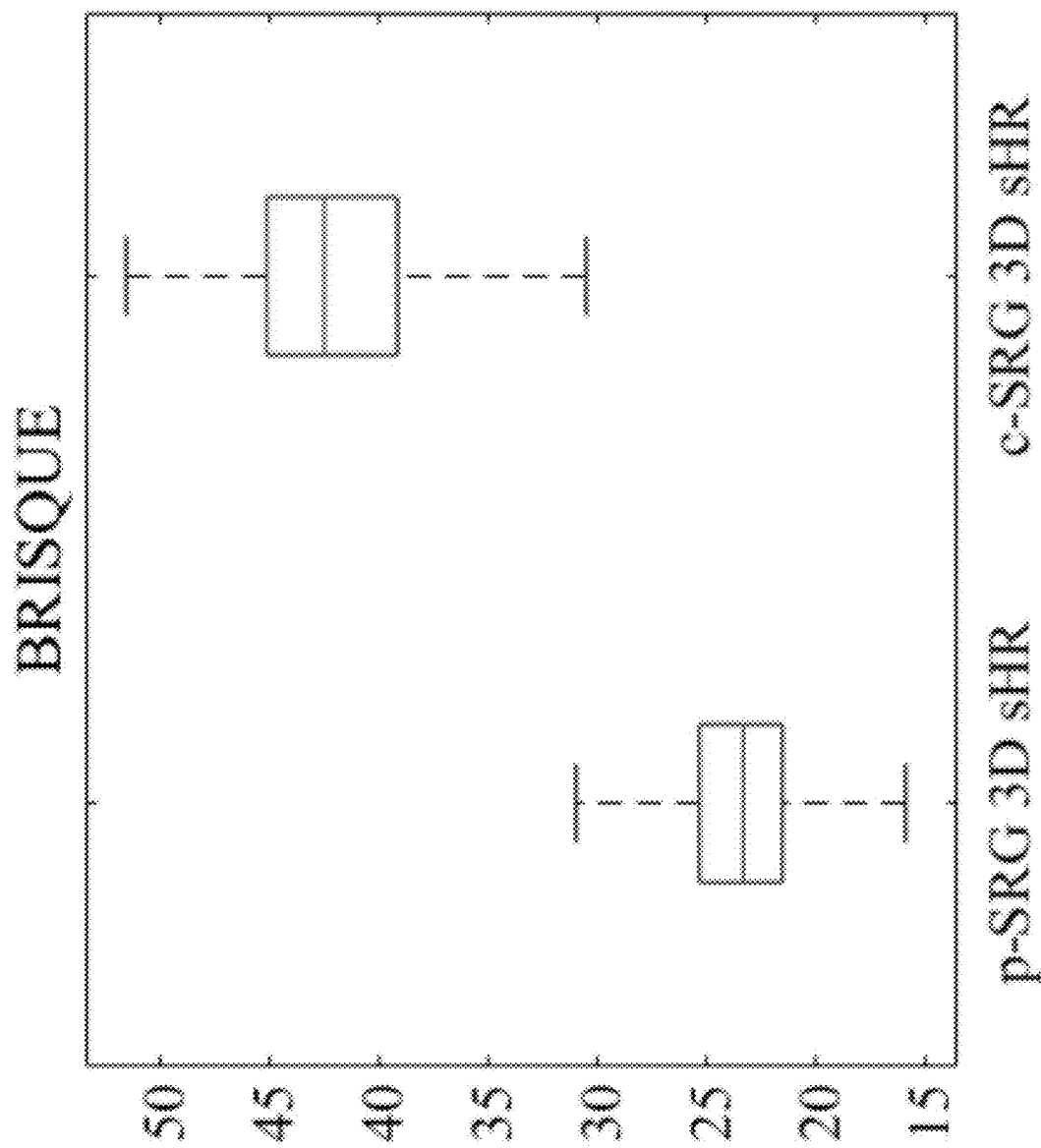
FIG. 38 is a graph summarizing a BRISQUE index calculated for 632 SR outputs of an SRG method in accordance with an aspect of the disclosure and a conventional SRG method tested on 3D LR breath-hold MRIs.

To evaluate the performance of the MRI SR SRG model described above and the conventional SRG model in the absence of ground truth reference HR images, the Blind/Referenceless Image Spatial Quality Evaluator (BRISQUE) metric was computed (FIG. 38). The BRISQUE index used scene statistics of locally normalized luminance coefficients to quantify possible losses of "naturalness" in the image due to the presence of distortions, thereby leading to a holistic measure of quality. A smaller score indicated better perceptual quality. The conventional SRG output scored 42.0±4.6, while the score for the MRI SR SRG model improved by 42.6%, measuring 24.1±3.8. The statistics of the computed values of the BRISQUE index are presented in Table 4 below.

TABLE 4

Statistics of the computed BRISQUE scores for SRG of MRI SR framework and conventional SRG outputs for 632 3D LR breath-hold MRIs.

| | BRISQUE | |
| --- | --- | --- |
| | p-SRG 3D sHR | c-SRG 3D sHR |
| Mean | 24.1 | 42.0 |
| Std | 3.8 | 4.6 |
| Min | 15.4 | 28.9 |
| Median | 23.4 | 42.5 |
| Max | 35.7 | 51.6 |

Figure 39:
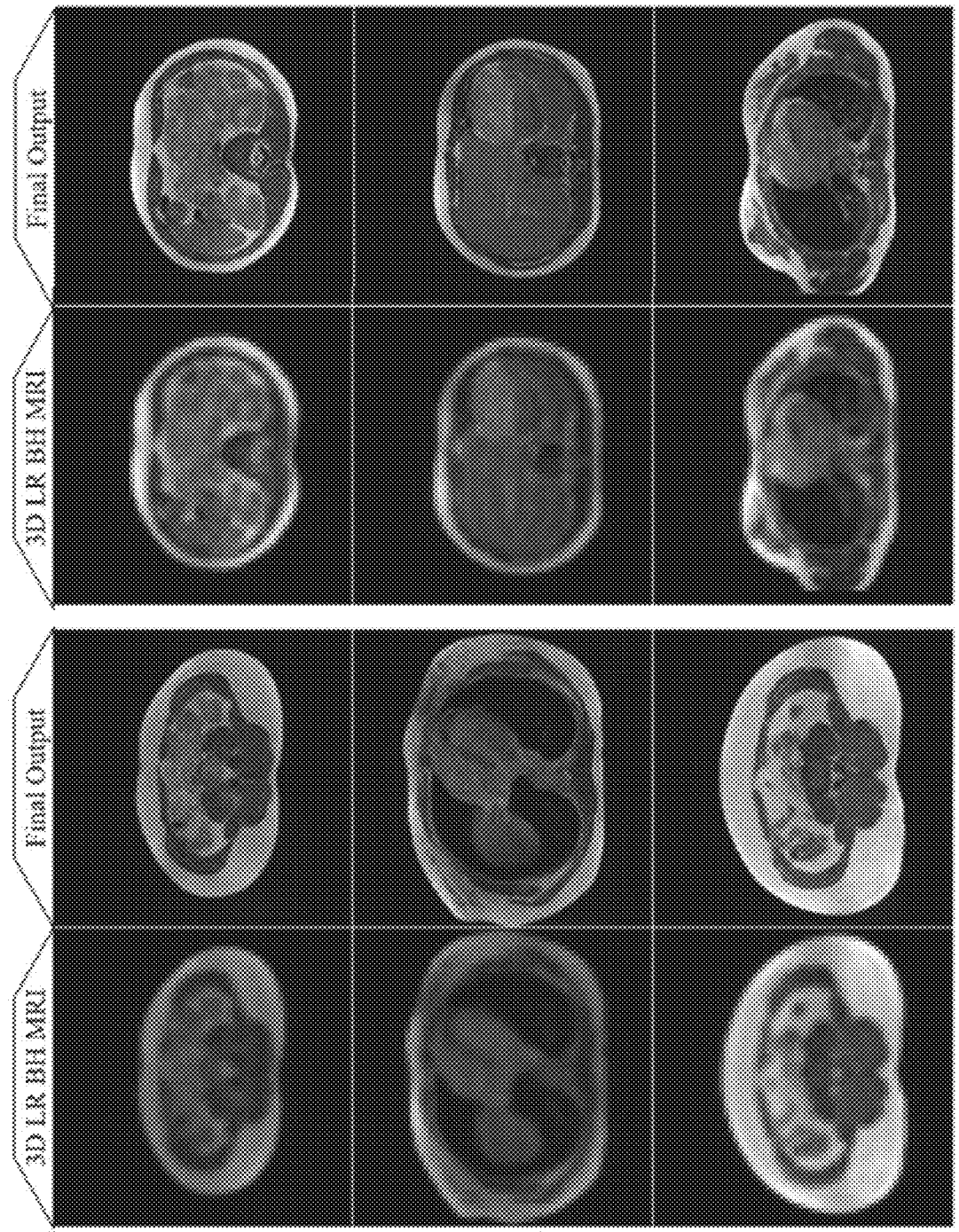
FIG. 39 contains a series of images including input (left column; 2.5 sec/vol, 64×64 pixels, 6.0 mm×6.0 mm per pixel) and output (right column; 0.022 sec/vol processing time, 256×256 pixels, 1.5 mm×1.5 mm per pixel) for 3D LR breath-hold (BH) scans using the cascaded deep learning framework in accordance with an aspect of the disclosure.

FIG. 39 contains a series of axial slices of the 3D LR breath-hold MRI acquisitions (left) and the corresponding SR 3D MRIs (right) generated using the full cascaded DL framework including the SRG of the MRI SR framework. The overall qualities of the cascaded DL results were equivalent to the physically scanned HR breath-hold MRIs.

Example 5: Validation of Super-Resolution Generative Model (SRG) for MRI SR Network on 4D Low Resolution Free-Breathing MRI Scans To validate the accuracy of the SRG of the MRI SR network described above, the following experiments were conducted.

High resolution MR images based on 4D LR free breathing MRI scans were obtained using a conventional SRG model and using the MRI SR framework as described above, including the SRG described above. Results for the SR reconstruction of 4D LR free breathing MRI scans (FIG. 40A) are shown for the MRI SR framework described above (FIGS. 40B and 40C) as well as a conventional SRG model (FIGS. 40D and 40E). Based on the results of the axial cases, the SRG model of the MRI SR framework described above outperformed the conventional SRG model. In a magnified view of the marked region of interest (ROI), the boundaries of diaphragm positions in the images produced using the SRG model of the MRI SR framework (FIG. 40C) are clearly distinctive compared to the conventional SRG outputs (FIG. 40E).

Figure 41:
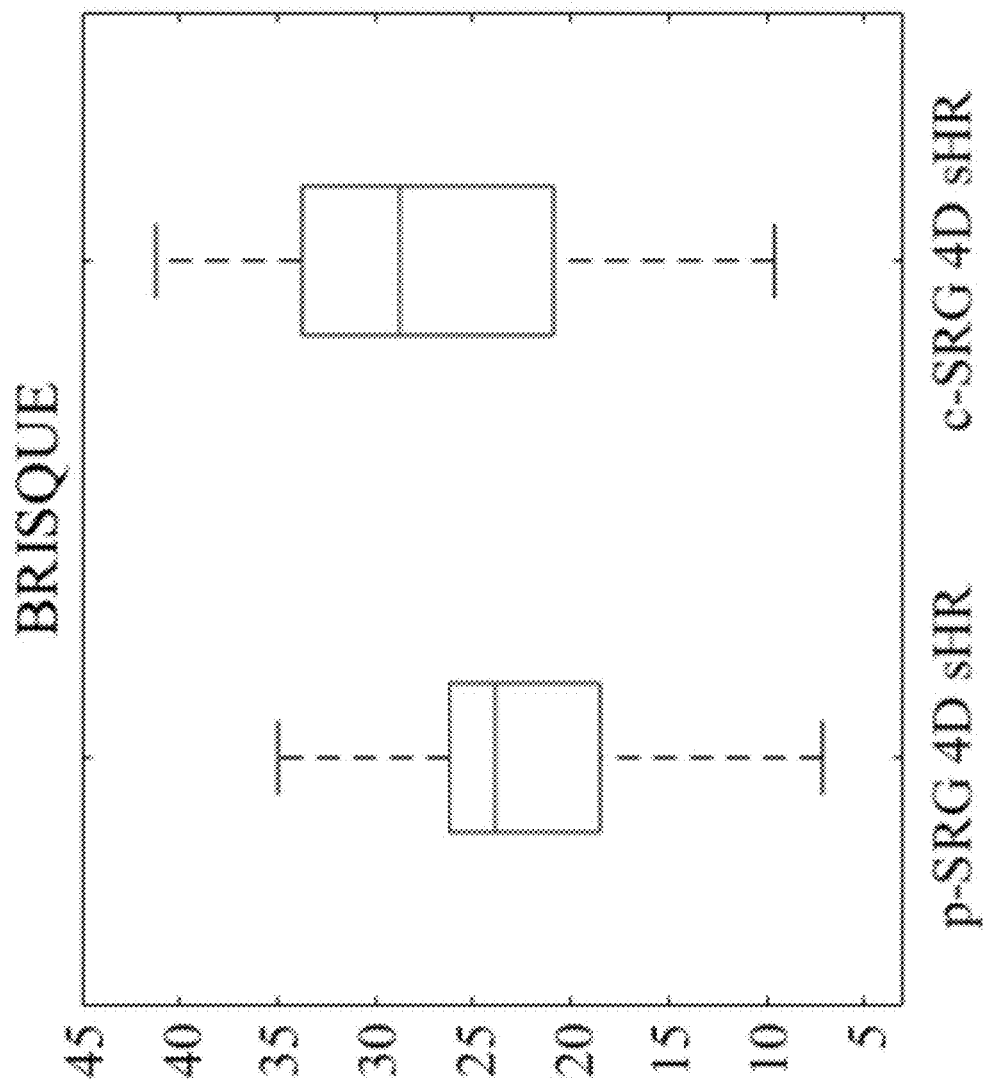
FIG. 41 is a graph summarizing BRISQUE index calculated for 800 SR outputs of SRG in accordance with an aspect of the disclosure and a conventional SRG method on LR free breathing 4D-MRI scans.

FIG. 41 displays the results of the BRISQUE index computed for SR 4D-MRI data generated by the SRG model of the MRI SR framework and the conventional SRG model. In the case of the conventional SRG, the images were scored 27.6±8.1, while for the SRG model off the MRI SR network, the results were consistently improved by 19.5%, measuring 22.2±5.7.

The associated statistics are presented in Table 5.

TABLE 5

Statistics of the computed BRISQUE scores for 800 p-SRG and c-SRG outputs for LR free breathing 4D-MRI scans.

| | BRISQUE | |
| --- | --- | --- |
| | p-SRG 4D sHR | c-SRG 4D sHR |
| Mean | 22.2 | 27.6 |
| Std | 5.7 | 8.1 |
| Min | 1.1 | 9.6 |
| Median | 23.9 | 28.8 |
| Max | 35.0 | 41.2 |

Reconstruction results for a LR 4D-MRI scan with and without the DAE described above are displayed in FIGS. 42A, 42B, 42C, 42D, 42E, and 42F. Without the use of DAE (FIGS. 42B and 42C), the noise was amplified in the generated SR images since the SRG network cannot distinguish the noise features from the input LR data. The difference was prominent in the magnified view of the vertebral and intervertebral structures (FIGS. 42C and 42F), where the boundary became unclear due to the degradation in image quality. By contrast, no severe degradation was present with the use of DAE (FIGS. 42E and 42F). This result confirmed that the DAE served an important role in preserving anatomical detail during the SR reconstruction process.

Figure 43:
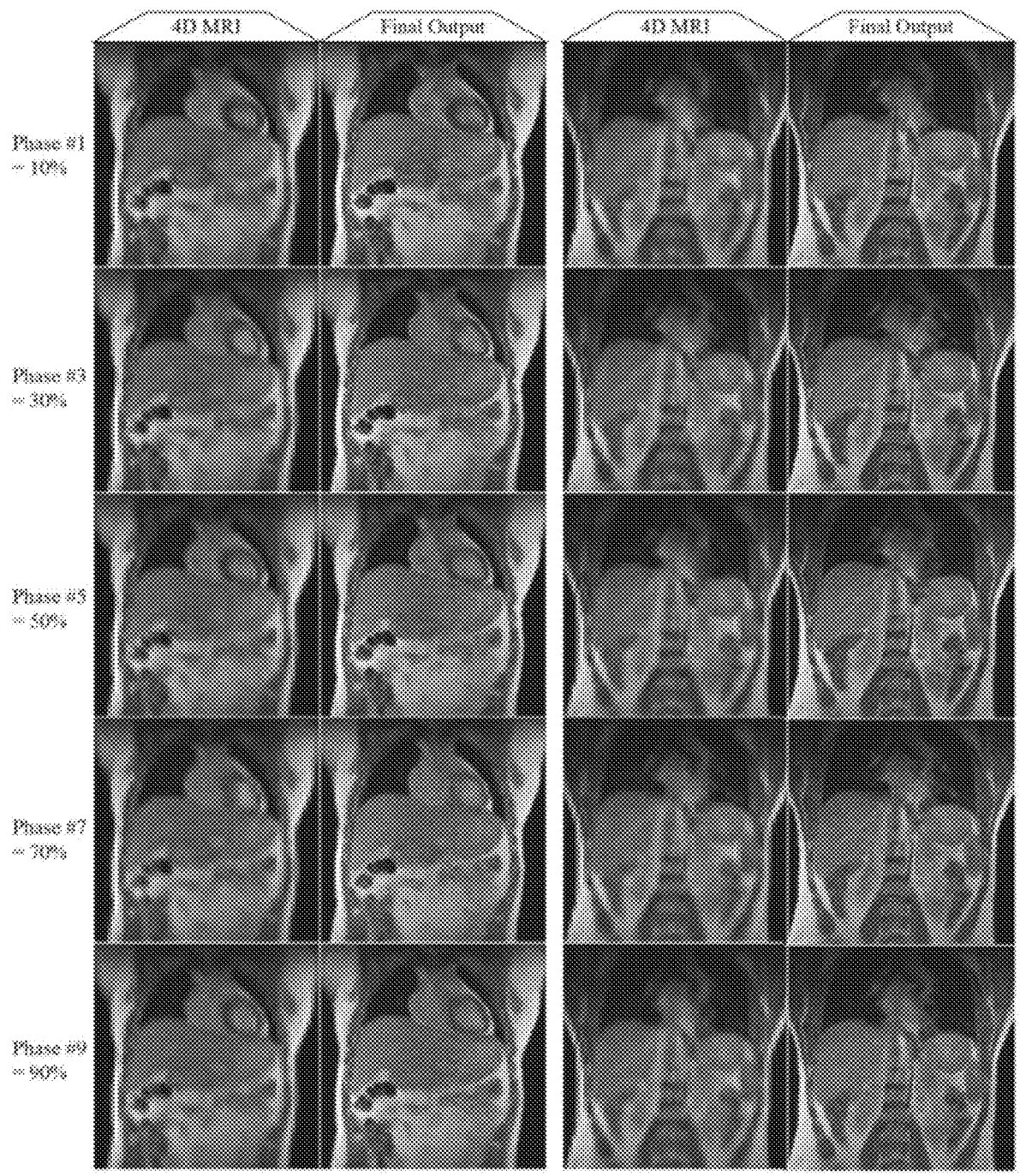
FIG. 43 contains a series of images representing 4D MRI input (left; 2.5 sec/vol, 64×64 pixels, 6.0 mm×6.0 mm per pixel) and MRI SR output (right; 0.022 sec/vol processing time, 256×256 pixels, 1.5 mm×1.5 mm per pixel) of coronal 4D-MRI acquisition at five breathing phases using a cascaded deep learning framework in accordance with an aspect of the disclosure.

FIG. 43 contains a series of coronal slices of a LR 4D-MRI scan along with the corresponding SR reconstruction results using the full cascaded DL (MRI SR) framework at 10%, 30% 50%, 70%, and 90% breathing phases. The overall quality of the cascaded DL results was equivalent to the physically scanned HR MRIs at each phase.

Example 6. Effect of Training Data Set on Generative Network Architecture

To determine the robustness of the generative (G) network architecture described above against the size of the training data set, the pix and the aspp implementations of the generative network described above were trained from scratch using image data from 10, 20, 30, 40, and 48 breast patients. The trained pix and aspp were each evaluated after each model completed training. 50 paired CT/MR images from each patient were selected for training, yielding training data sets of 500, 1000, 1500, 2000, and 2400 paired images in each of the breast patient groupings described above, respectively. 0.35T MR images were acquired using the first generation MRIdian system (ViewRay Inc., Oakwood Village, OH) with a T1w GR sequence. CT simulation scans (Brilliance CT, Philips Medical Systems, Andover, MA) were downsampled to match the resolution of the corresponding MRI scan (1.5×1.5×1.5 mm3) and deformably registered to the corresponding MRI scan using the ViewRay treatment planning system before being exported for training. Histogram matching was performed on both sets of images prior to thresholding the images of each modality at specified values and resealing the intensities to fill the entire unsigned 16-bit integer range to create a more uniform data set.

For every training set size and network architecture pairing, the framework was trained for 2500 epochs using TensorFlow50 v1.7.0 running on a 12 GB Titan Xp GPU (NVIDIA, Santa Clara, CA), and the time required for training was evaluated for each training data set.

The performance of both network architectures was evaluated using a number of metrics. A 10-fold cross validation was conducted for the aspp architecture to establish the performance of the network. Three quantitative metrics were utilized to evaluate image quality: root mean square error (RMSE) to capture voxel-wise agreement, structural similarity index (SSIM) to evaluate structural agreement, and peak signal-to-noise ratio (PSNR) to measure the quality of sCT reconstructions. Additionally, the time required to complete 2500 training epochs was recorded for both architectures and each training data set size. A comparison between the generated sCT images and true CT images for 12 test patients was performed using the RMSE, SSIM, and PSNR metrics described above.

The performance of the deep spatial pyramid convolutional framework was evaluated using 10-fold cross validation. At each iteration, 54 data sets were used to train the aspp architecture from scratch. The trained aspp model was then applied to 5 data sets—approximately 500 images per iteration—for evaluation. Over all 10 folds of the cross-fold evaluation, average values of 27.6±7.2 HU, 0.9985±308 0.0011, and 67.8±2.2 were observed for the RMSE, SSIM, and PSNR metrics, respectively.

Figure 22:
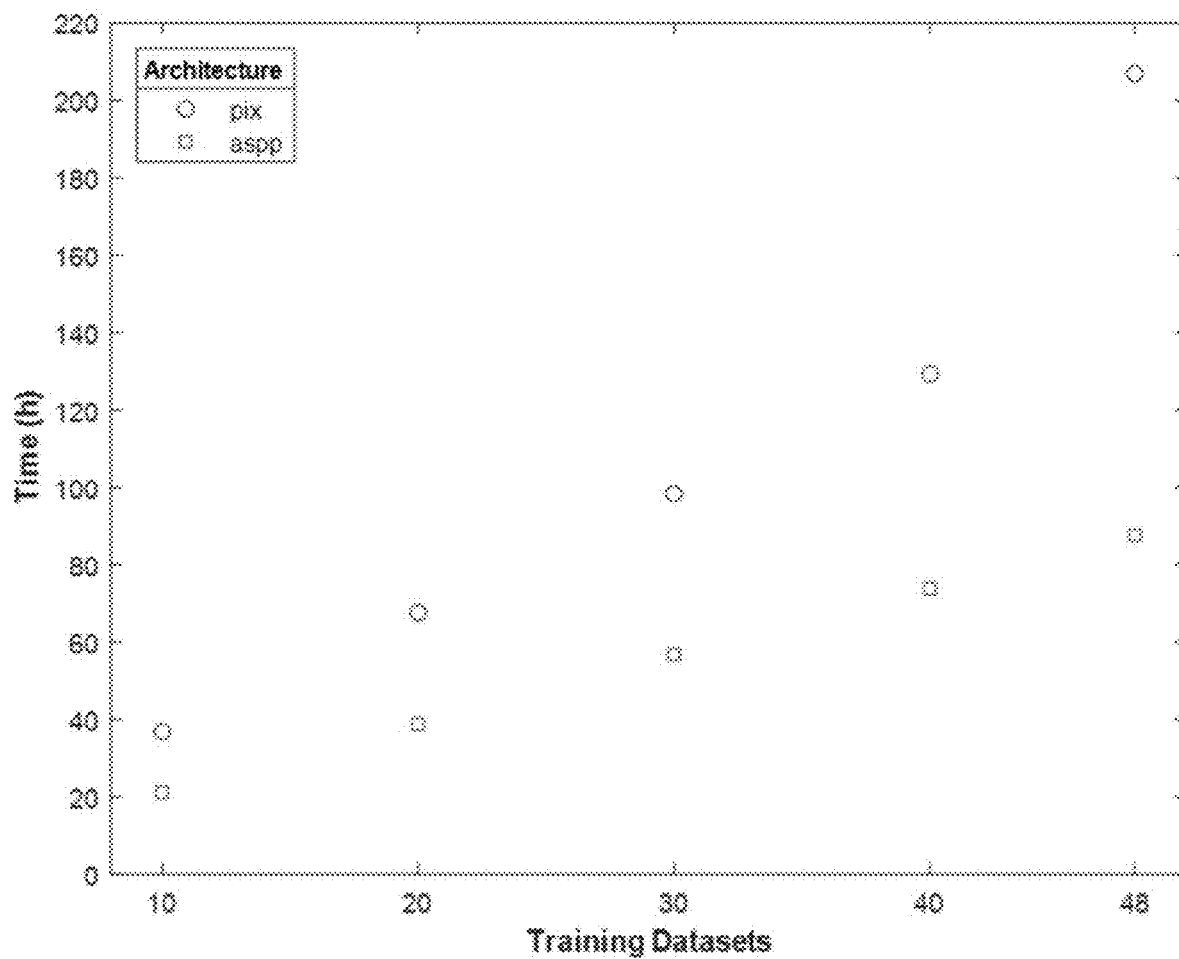
FIG. 22 is a graph summarizing times to complete 2500 training epochs for the pix (blue) and aspp (red) architectures plotted against the size of the training data set.

The time required to complete 2500 training epochs is plotted for each architecture and training data set size in FIG. 22. Shorter training times were observed for the aspp architecture compared to those of the pix architecture at every training set size, ranging from 21-87 and 37-207 hours, respectively, depending on the size of the data set.

1042 images from 12 test patients were generated using each architecture and training data set size as described above. Values of the RMSE calculated within the body contour for each architecture and training data set size are plotted in FIG. 23. The lowest mean value of 17.7±4.3 HU is observed for the aspp48 architecture trained with data from 48 patients. FIG. 24 summarizes the calculated values of the SSIM metric over this test set for each architecture and training data set size. The aspp48 model again demonstrated the best observed value of 0.9995±0.0003, although relatively stable performance was observed in this metric. Calculated results for the PSNR metric are presented in FIG. 25. The highest observed value of 71.7±2.3 was achieved by the aspp48 model. Additional statistics for each metric are presented in Tables 6, 7, and 8.

TABLE 6

Figure 23:
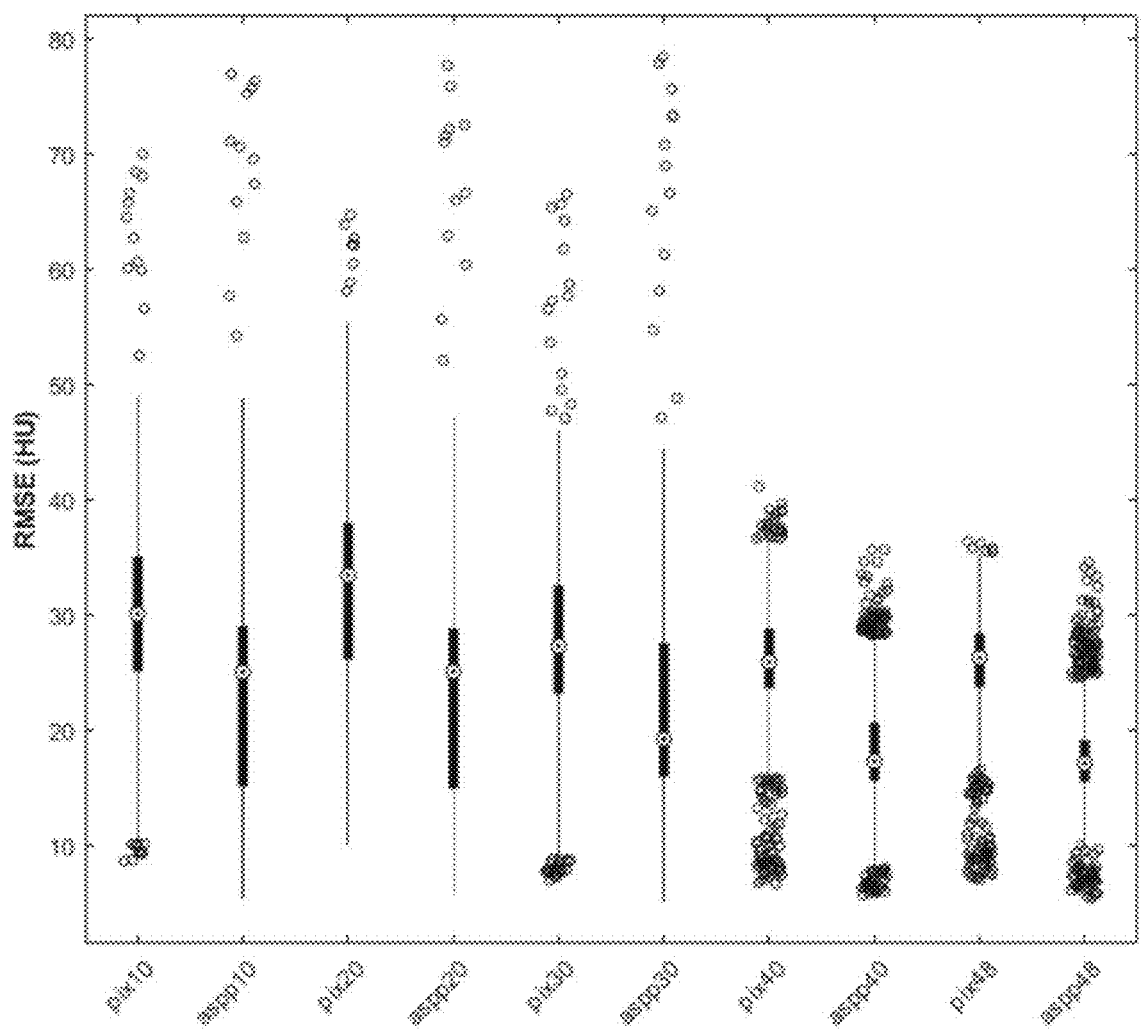
FIG. 23 is a graph summarizing RMSE values calculated over 1042 test images generated by the pix and aspp architectures for a range of training data set sizes. Statistical measures are included in Table 6 herein.
Figure 24:
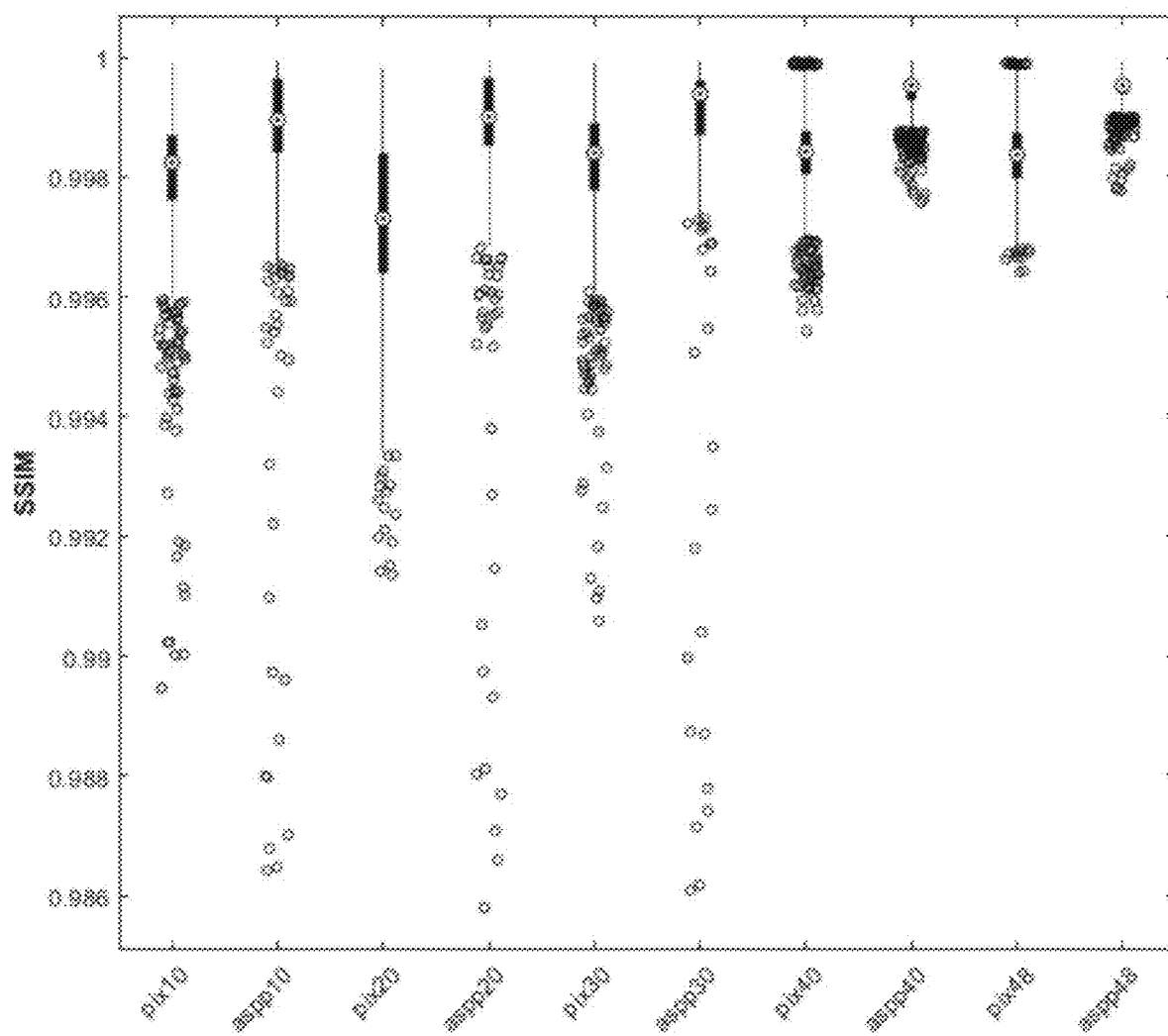
FIG. 24 is a graph summarizing values of the SSIM metric calculated over 1042 test images generated by each architecture and training data set size. Statistical measures are included in Table 7.

RMSE statistics accompanying FIG. 23. Reported measures are in units of HU.

|  | pix10 | aspp10 | pix20 | aspp20 | pix30 | aspp30 | pix40 | aspp40 | pix48 | aspp48 |
|---|---|---|---|---|---|---|---|---|---|---|
| Mean | 29.8 ± 8.6 | 23.9 ± 9.7 | 32.4 ± 8.5 | 23.8 ± 9.5 | 27.8 ± 8.1 | 22.0 ± 9.0 | 25.8 ± 5.8 | 18.0 ± 5.2 | 25.4 ± 5.2 | 17.7 ± 4.3 |
| Median | 30.1 | 25.1 | 33.5 | 25.1 | 27.3 | 19.2 | 25.9 | 17.3 | 26.3 | 17.1 |
| Min | 8.6 | 5.5 | 10.2 | 5.7 | 7.0 | 5.1 | 6.7 | 5.7 | 7.1 | 5.4 |
| Max | 70.0 | 77.0 | 64.7 | 77.7 | 66.5 | 78.4 | 41.2 | 35.7 | 36.4 | 34.6 |

TABLE 7

SSIM statistics accompanying FIG. 24.

|  | pix10 | aspp10 | pix20 | aspp20 | pix30 |
|---|---|---|---|---|---|
| Mean | 0.9986 ± 0.0013 | 0.9968 ± 0.0013 | 0.9072 ± 0.0013 | 0.9988 ± 0.0013 | 0.9982 ± 0.0012 |
| Median | 0.9982 | 0.9990 | 0.9073 | 0.9990 | 0.9084 |
| Min | 0.9995 | 0.9864 | 0.9914 | 0.9858 | 0.9906 |
| Max | 0.9999 | 1.0000 | 0.9998 | 1.0000 | 0.9999 |

|  | aspp30 | pix40 | aspp40 | pix48 | aspp48 |
|---|---|---|---|---|---|
| Mean | 0.9990 ± 0.0013 | 0.9981 ± 0.0008 | 0.9994 ± 0.0004 | 0.9984 ± 0.0007 | 0.9998 ± 0.0003 |
| Median | 0.9994 | 0.9984 | 0.9996 | 0.9984 | 0.9995 |
| Min | 0.9861 | 0.9954 | 0.9976 | 0.9964 | 0.9978 |
| Max | 1.0000 | 0.9999 | 1.0000 | 0.9999 | 1.0000 |

TABLE 8

Figure 25:
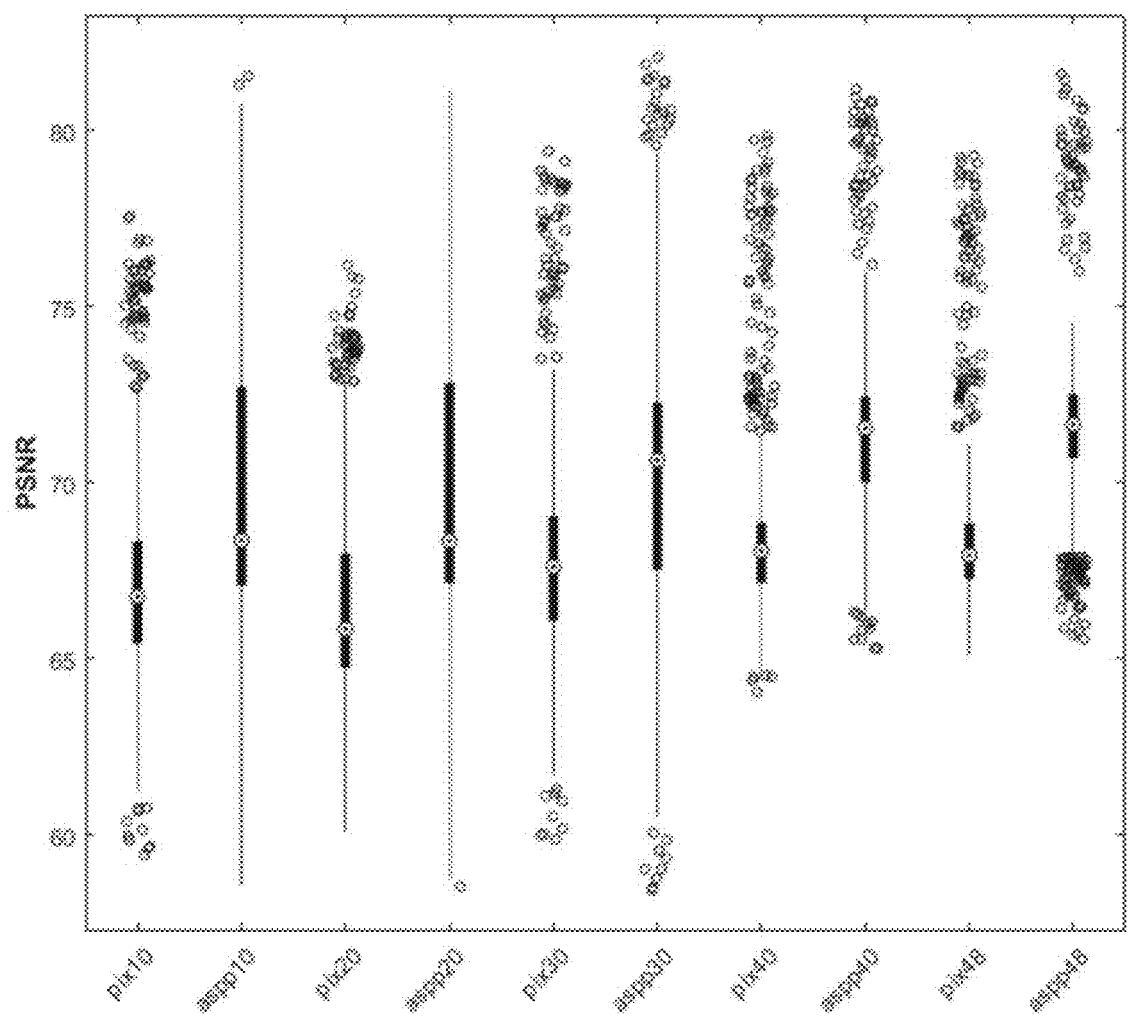
FIG. 25 is a graph summarizing PSNR values calculated over 1042 test images generated by each architecture and training data set size. Statistical measures are included in Table 8.

PSNR statistics accompanying FIG. 25.

|  | pix10 | aspp10 | pix20 | aspp20 | pix30 | aspp30 | pix40 | aspp40 | pix48 | aspp48 |
|---|---|---|---|---|---|---|---|---|---|---|
| Mean | 67.3 ± 2.8 | 60.5 ± 3.6 | 66.5 ± 2.6 | 60.5 ± 3.5 | 67.9 ± 2.0 | 70.1 ± 3.4 | 68.4 ± 2.5 | 71.3 ± 2.6 | 68.5 ± 2.4 | 71.7 ± 2.3 |
| Median | 66.8 | 68.3 | 65.8 | 68.3 | 67.6 | 70.6 | 68.1 | 71.6 | 67.9 | 71.7 |
| Min | 59.4 | 58.6 | 60.1 | 58.5 | 59.9 | 58.4 | 64.0 | 65.3 | 65.1 | 65.6 |
| Max | 77.6 | 81.6 | 76.2 | 81.1 | 70.4 | 82.1 | 70.9 | 81.2 | 70.3 | 81.6 |

Figure 26:
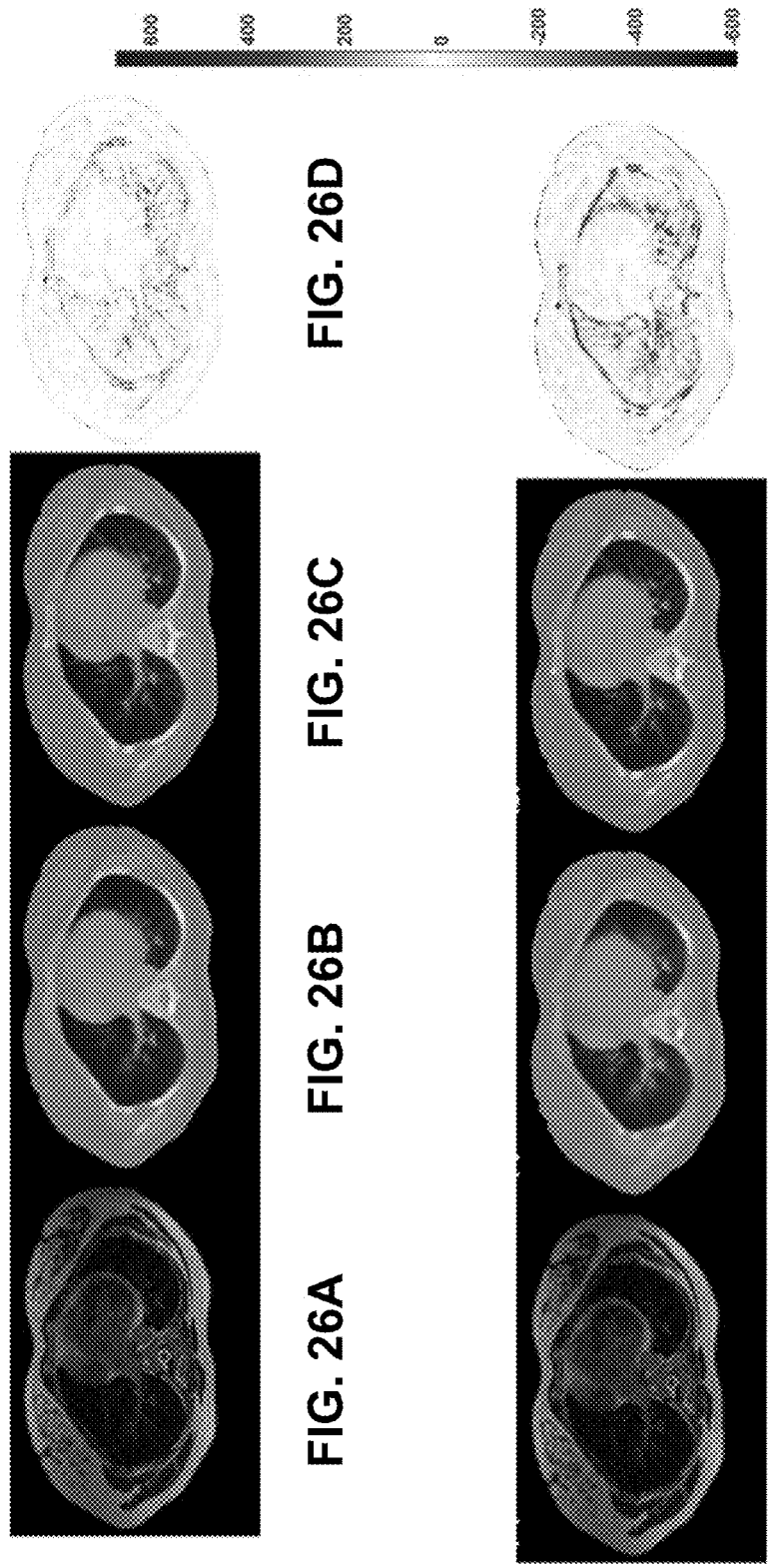
FIGS. 26A, 26B, 26C, 26D, 26E, 26F, 26G, and 26H contain a series of images associated with the transformation of an MR image to a sCT image using the pix and asps models descried herein.

Image comparisons for a representative axial slice are presented in FIGS. 26A, 26B, 26C, 26D, 26E, 26F, 26G, and 26H. RMSE values of 17.7 HU and 27.3 HU for the sCT reconstructions of the selected slice for the aspp48 and pix48 results, respectively, are comparable to the mean values presented in Table 6. The input MR image (FIG. 26A) is shown alongside the sCT reconstruction generated by the aspp48 (FIG. 26B) and pix48 (FIG. 26F) models as well as the corresponding ground truth CT image (FIGS. 26C and 26G, respectively). Difference maps illustrate the difference in HU values in the true CT image and the sCT image for each architecture (FIGS. 26D and 26H, respectively).

Figure 27:
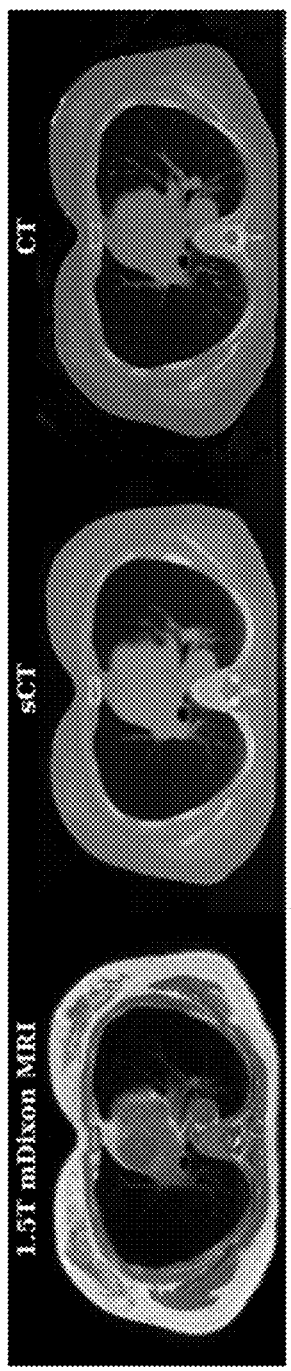
FIG. 27 contains a series of images, including an input MR image (left) acquired in a 1.5T MRI scanner with an mDixon sequence, an ASPP-based sCT image (center), and corresponding clinical CT image (right) for a breast case.

Evaluation of the deep spatial pyramid convolutional framework was extended to images of other MRI sequences and field strengths. FIG. 27 presents the sCT reconstruction for a selected slice from an ASPP-based model trained with 1.5T mDixon MR images (Ingenia MR, Philips Medical Systems, Andover, MA) and the corresponding CT images of the breast.

Example 7: Validation of Radiation Dose Distributions Generated Using sCT

To validate the accuracy of radiation dose distributions produced using sCT images obtained using the methods described above against corresponding radiation dose distributions produced using clinical CT images, the following experiments were conducted.

Dose distributions calculated based on the electron density information derived from sCT images generated with the deep spatial convolutional framework described above were compared to those based on true CT images for 4 test patients using the 3D gamma index with 2%/2 mm criterion.

Figure 28:
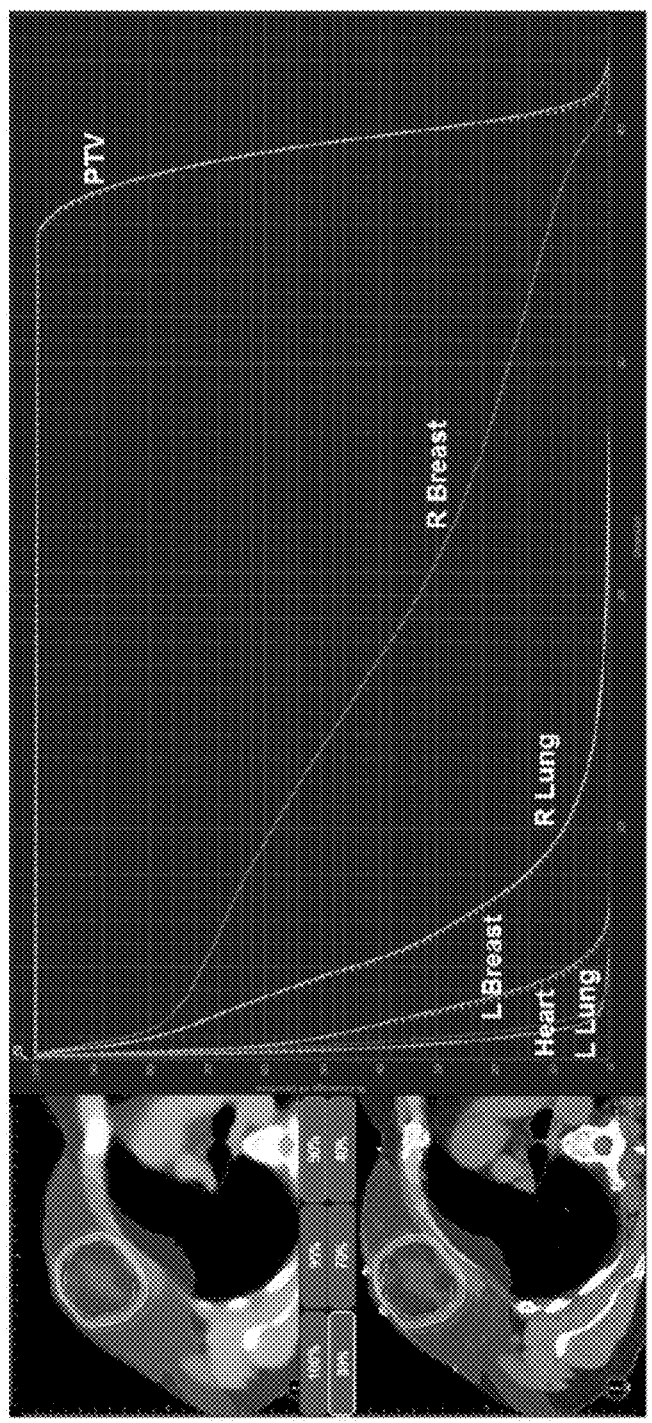
FIG. 28 is a graph summarizing dose distributions for the sCT-based (top left) and clinical (bottom left) plans alongside the plan DVHs for the proposed (solid lines) and clinical (dashed lines) plans.

Dose calculations were performed for 4 test patients using optimization parameters selected in clinical simulation plans and electron density information derived from aspp-generated sCT images. Dose distributions from the clinical and proposed plans are presented in FIG. 28 for comparison along with the corresponding dose-volume histograms (DVHs). Calculated dose metrics including the percentage of the PTV covered by 95% of the prescribed dose (D95), PTV max and mean dose, left and right lung max and mean dose, percent volume of the heart receiving 2 Gy or more (V2), and heart max and mean dose for the clinical and proposed plans are presented in Table 9.

$D_{95}$ for the PTV calculated in the proposed plan varied by less than 1% from that calculated in the clinical plan in each test case. Similar agreement was observed in the other calculated metrics. Disagreements of greater than 1% arose from dose differences of less than 1 Gy, where discrepancies were largely inconsequential. The 3D gamma index comparing the clinical and proposed dose distributions yielded passing rates equal to or greater than 98% for all patients using a 2%/2 mm criterion.

TABLE 9

Selected dose metrics compared between simulation plans based on clinical CT scans and plans calculated based on aspp-generated sCTs for four test patients. Max and mean doses are reported in units of Gy.

| Pt. |  | PTV | | | Left Lung | | Right Lung | | | Heart | |
|---|---|---|---|---|---|---|---|---|---|---|---|
|  |  | $D_{95}$ (%) | Max | Mean | Max | Mean | Max | Mean | $V_2$ (%) | Max | Mean |
| 1 | c. | 56.18 | 22 | 19.28 | 1.09 | 0.23 | 6.88 | 0.9 | 0 | 1.35 | 0.21 |
|  | p. | 56.12 | 22 | 19.26 | 1.14 | 0.24 | 6.87 | 0.89 | 0 | 1.37 | 0.2 |
| 2 | c. | 97.88 | 42.12 | 39.27 | 4.15 | 0.83 | 21.8 | 3.85 | 5 | 4.32 | 0.69 |
|  | p. | 98.66 | 42.59 | 39.51 | 4.22 | 0.85 | 21.97 | 3.9 | 5.09 | 4.32 | 0.68 |
| 3 | c. | 95.14 | 42.89 | 39.2 | 4.72 | 0.6 | 26.97 | 4.29 | 4.36 | 3.87 | 0.8 |
|  | p. | 96.05 | 43.12 | 39.26 | 4.86 | 0.61 | 27.15 | 4.35 | 4.46 | 4.03 | 0.8 |
| 4 | c. | 97.27 | 43.33 | 39.46 | 3.1 | 0.228 | 29.36 | 4.16 | 4.25 | 4.52 | 0.9 |
|  | p. | 97.45 | 43.2 | 39.48 | 3.31 | 0.29 | 29.45 | 4.21 | 4.48 | 4.54 | 0.91 |

What is claimed is:

1. A computer-implemented method of transforming a low-resolution MR image into a super-resolution MR image using an MRI SR deep CNN system comprising a deep CNN-based de-noising auto-encoder (DAE) network and a deep CNN-based super-resolution generative network (SRG), the method comprising:

receiving, using a computing device, a low-resolution MR image;

transforming, using the computing device, the low-resolution MR image into a de-noised MR image using the DAE network, the DAE network comprising six convolutional encoder layers with 4×4 filters and six de-convolutional decoder layers with 4×4 filters, wherein each convolutional encoder layer comprises a single convolutional filter with stride 2, each de-convolution decoder layer comprises a single deconvolutional filter with stride 2, and each convolutional encoder layer and each de-convolution decoder layer ends with a leaky and standard rectified linear unit (ReLU); and, transforming, using the computing device, the de-noised MR image into the super-resolution MR image using the SRG network.

2. The computer-implemented method of claim 1, wherein the SRG network comprises:
   two up-sampling layers,
   eight residual blocks, each residual block comprising two 3×3 convolutional filters separated by a ReLU activation with an elementwise sum operator attached at the end of the layer; and
   two output layers, each output layer comprising a 3×3 convolutional filter, ReLU activation, and a subpixel operator up-sampling layer.

3. The computer-implemented method of claim 2, further comprising training the DAE network by:
   receiving, using the computing device, a set of noisy low resolution MR images;
   transforming, using the computing device, each noisy MR image into a de-noised MR image using a noise filter, wherein each noisy MR image and corresponding de-noised MR image together form a noisy/de-noised MR image pair; and
   training, using the computing device, the DAE network to minimize a reconstruction error given by $\|g_{\theta_g}(f_{\theta_f}(\tilde{x}))-x\|$ for each matched noisy/de-noised low resolution image pair, where x denotes each de-noised MR image, $\tilde{x}$ denotes each noisy MR image, and $f_{\theta_f}$ and $g_{\theta_g}$ denote the encoding and decoding network parameterized by $\theta_f$ and $\theta_g$, respectively.

4. The computer-implemented method of claim 3, wherein the noise filter comprises a non-local means filter.

5. The computer-implemented method of claim 2, further comprising training the SRG network by:
   receiving, using the computing device, a set of matched low resolution/high resolution MR image pairs;
   forming, using the computing device, a generative adversarial network (GAN) including a generative model G parametrized by $\theta_G$ and comprising the SRG network and a discriminative model D parametrized by $\theta_D$, the discriminative model D configured to determine a probability that a high resolution MR image is a high resolution image or an SRG-transformed low resolution MR image from a matched low resolution/high resolution MR image pair; and
   training, using the computing device, the GAN to solve the optimization problem given by $$\min_{\theta_G} \max_{\theta_D} \{\mathbb{E}_{x \sim P_{data}} \log D_{\theta_D}(x) + \mathbb{E}_{z \sim p_z} \log(1 - D_{\theta_D}(G_{\theta_G}(z)))\}$$

by updating D and G in alternating steps while fixing the other parameter, wherein the GAN is trained if D is unable to determine whether each high resolution MR image is the selected high resolution MR image or the transformed low resolution MR image from each matched low resolution/high resolution MR image pair.

6. The computer-implemented method of claim 5, wherein the set of matched low resolution/high resolution MR image pairs is produced by:
   transforming, using the computing device, a high resolution MR image to a low resolution MR image training using a deep CNN-based down-sampling network (DSN), the DSN comprising:
      two down-sampling layers, each down-sampling layer comprising a 3×3 convolutional filter of stride 2 followed by a ReLU activation;
      two residual blocks, each residual block comprising two 3×3 convolutional filters separated by a ReLU activation and followed by an elementwise sum operator; and
      an output layer.

\* \* \* \* \*